(12) United States Patent
Yu et al.

(10) Patent No.: US 8,697,743 B2
(45) Date of Patent: Apr. 15, 2014

(54) ANTIOXIDANT CAMPTOTHECIN DERIVATIVES AND ANTIOXIDANT ANTINEOPLASTIC NANOSPHERES THEREOF

(75) Inventors: John S. Yu, Los Angeles, CA (US); Bong Seop Lee, Torrance, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 13/114,539

(22) Filed: May 24, 2011

(65) Prior Publication Data

US 2011/0300187 A1    Dec. 8, 2011

Related U.S. Application Data

(63) Continuation-in-part of application No. PCT/US2009/065776, filed on Nov. 24, 2009.

(60) Provisional application No. 61/117,299, filed on Nov. 24, 2008.

(51) Int. Cl.
*A61K 38/00* (2006.01)
*A61K 31/44* (2006.01)
*A61K 31/385* (2006.01)
*A61K 31/38* (2006.01)
*A61K 31/27* (2006.01)
*A61P 35/00* (2006.01)
*A01N 43/42* (2006.01)
*A01N 43/40* (2006.01)
*A01N 43/26* (2006.01)
*A01N 43/06* (2006.01)
*A01N 47/10* (2006.01)

(52) U.S. Cl.
USPC .......... 514/440; 514/19.3; 514/280; 514/338; 514/444; 514/480; 514/483

(58) Field of Classification Search
None
See application file for complete search history.

(56) References Cited

U.S. PATENT DOCUMENTS

| | | | |
|---|---|---|---|
| 3,963,771 A | 6/1976 | Robson et al. | |
| 5,122,526 A | 6/1992 | Wall et al. | |
| 5,543,158 A | 8/1996 | Gref et al. | |
| 5,962,520 A | 10/1999 | Smith et al. | |
| 6,013,663 A | 1/2000 | Fujita et al. | |
| 6,090,842 A | 7/2000 | Packer et al. | |
| 6,117,899 A | 9/2000 | Wessel et al. | |
| 6,127,394 A | 10/2000 | Pershadsingh et al. | |
| 6,150,358 A | 11/2000 | Goldstein et al. | |
| 6,204,288 B1 | 3/2001 | Pershadsingh et al. | |
| 6,235,772 B1 | 5/2001 | Packer et al. | |
| 6,288,106 B1 | 9/2001 | Pearson et al. | |
| 6,353,011 B1 | 3/2002 | Pershadsingh et al. | |
| 6,369,098 B1 | 4/2002 | Pershadsingh et al. | |
| 6,380,405 B1 | 4/2002 | Ekwuribe et al. | |
| 6,387,945 B2 | 5/2002 | Packer et al. | |
| 6,572,888 B2 | 6/2003 | Byrd | |
| 6,605,637 B1 | 8/2003 | Harnett et al. | |
| 6,629,995 B1 | 10/2003 | Wrenn et al. | |
| 6,664,287 B2 | 12/2003 | Avery et al. | |
| 6,821,529 B2 | 11/2004 | Nelson | |
| 6,878,374 B2 | 4/2005 | Yu et al. | |
| 6,887,891 B2 | 5/2005 | Harnett et al. | |
| 6,900,337 B2 | 5/2005 | Manzer et al. | |
| 6,900,338 B1 | 5/2005 | Haj-Yehia | |
| 6,936,715 B2 | 8/2005 | Harnett et al. | |
| 6,998,115 B2 | 2/2006 | Langer et al. | |
| 7,048,925 B2 | 5/2006 | Van et al. | |
| 7,056,901 B2 | 6/2006 | Frechet et al. | |
| 7,157,444 B2 | 1/2007 | Nelson | |
| 7,220,414 B2 | 5/2007 | Brocchini et al. | |
| 8,318,795 B2 | 11/2012 | Yu et al. | |
| 2004/0053989 A1 | 3/2004 | Prendergast et al. | |
| 2005/0043493 A1 | 2/2005 | Smith et al. | |
| 2005/0065194 A1 | 3/2005 | Shankar et al. | |
| 2006/0013882 A1 | 1/2006 | Kohn et al. | |
| 2007/0208134 A1 | 9/2007 | Hunter et al. | |

(Continued)

FOREIGN PATENT DOCUMENTS

EP    2125775    12/2009
JP    2010-520333    6/2010

(Continued)

OTHER PUBLICATIONS

Moon et al., "Antibody Conjugates of 7-Ethyl-10-hydroxycamptothecin (SN-38) for Targeted Cancer Chemotherapy", J.Med.Chem., published on web Oct. 22, 2008, vol. 51, pp. 6916-6926.*

(Continued)

*Primary Examiner* — James D Anderson
*Assistant Examiner* — Stephanie Springer
(74) *Attorney, Agent, or Firm* — Linda B. Huber; Nixon Peabody LLP

(57) ABSTRACT

The present invention is directed to antioxidant derivatives of camptothecin and antioxidant derivatives of camptothecin analogs and the preparation of nanometer-sized camptothecin prodrugs. Methods of synthesizing the antioxidant derivatives of camptothecin and antioxidant derivatives of camptothecin analogs, spontaneous emulsification or nanoprecipitation thereof to produce antioxidant camptothecin nanosphere prodrugs and their use in treating cancerous diseases are also provided. A further aspect of this invention is the use of these antioxidant camptothecin nanosphere prodrugs for the preparation of delivery devices of other pharmaceuticals and/or drugs. Additionally, methods of treating cancer with the camptothecin and antioxidant derivatives of camptothecin analogs, and nanometer-sized camptothecin prodrugs are also provided.

30 Claims, 19 Drawing Sheets
(14 of 19 Drawing Sheet(s) Filed in Color)

(56) References Cited

U.S. PATENT DOCUMENTS

| | | |
|---|---|---|
| 2007/0281047 A1 | 12/2007 | Henry et al. |
| 2010/0098653 A1 | 4/2010 | Yu |
| 2010/0291222 A1 | 11/2010 | Yu |
| 2011/0086073 A1 | 4/2011 | Yu |
| 2011/0300187 A1 | 12/2011 | Yu et al. |

FOREIGN PATENT DOCUMENTS

| | | |
|---|---|---|
| JP | 2012-509901 A | 4/2012 |
| WO | 9743274 A1 | 11/1997 |
| WO | 9801440 A2 | 1/1998 |
| WO | WO 99/38881 | 8/1999 |
| WO | WO 01/29221 | 4/2001 |
| WO | WO 01/53312 | 7/2001 |
| WO | WO 02/46465 A3 | 6/2002 |
| WO | WO 2004/050795 | 6/2004 |
| WO | WO 2008/012365 A2 | 1/2008 |
| WO | WO 2008/106640 A1 | 9/2008 |
| WO | WO 2009/086547 | 7/2009 |
| WO | WO 2009/148698 A1 | 12/2009 |
| WO | WO 2010/060098 A1 | 5/2010 |

OTHER PUBLICATIONS

European Application No. 08731097.5 Extended Search Report dated Jun. 15, 2011.
Casolaro et al. Redox-active Polymers: Sythesis and Exchange Reaction of Amino Compounds Containing a Cyclic Disulfide. Polymer (1994). 35(2): pp. 360-366.
Fujimoto et al. Synthesis of a Polymer Containing the Cyclic Disulfide (1, 2-Dithiolane) Structure. Die Makromolekulare Chemie (1974). 175: pp. 3597-3602.
Sieczkowska et al. Sythesis and Characterization of Photolabile Aminoterpolymers for Covalent Attachment onto Gold Substrates. Designed Monomers and Polymers (2005). 8(6): pp. 629-644.
Sun et al. Ultrathin Self-Assembled Polymeric Films on Solid Surfaces. I. Synthesis and Characterization of Acrylate Copolymers Containing Alkyl Disulfide Side Chains. Journal of Polymer Science: Part A: Polymer Chemistry. (1993). 31: pp. 1729-1740.
Sun et al. Ultrathin Self-Assembled Polymeric Films on Solid Surfaces. III. Influence of Acrylate Dithioalkyl Side Chain Length on Polymeric Monolayer Formation of Gold. J. Vac. Sci. Technol. A (1994). 12(4): pp. 2499-2506.
Japanese Application No. 2009-551871 Official Action dated Dec. 21, 2011.
Rice et al. Inhibition of multiple phases of human immunodeficiency virus type 1 replication by a dithiane compound that attacks the conserved zinc fingers of retroviral nucleocapsid proteins. Antimicrob Agents Chemother. (1997). 41 (2): pp. 419-426.
Kalyuzhny et al. Ligand effects on optical properties of CdSe nanocrystals. Journal of Physical Chemistry B. (2005). 109(15): pp. 7012-7021. ABSTRACT.
Kieller et al. The Five-membered Disulfide Ring System. III. Antineoplastic Potentialities. Acta Biochimica Polonica (1964). 11(2-3): pp. 279-291.
Lee et al. Nereistoxin and Cartap Neurotoxicity Attributable to Direct Block of the Insect Nicotinic Receptor/Channel. Journal of Agricultrual and Food Chemistry. (2003). 51(9): pp. 2646-2652. ABSTRACT.
Povalyaeva et al. Synthesis and Properties of N-substituted 4-amino-1,2, dithiolanes and Related Compounds. Zhurnal Organicheskoi Khimii. (2004). 20(4): pp. 849-860.
U.S. Appl. No. 12/528,067 Non-Final Office Action dated Jan. 4, 2012.
Hsu et al. Synthesis of functionalized 1,3-propanedithiols as derivatizing reagent for organoarsenic (III) compounds. Proceed. ERDEC Sci. Conf. Clin. Biol. Defense Res., Aberdeen Proving Ground. Nov. 17-20, 1998. ABSTRACT.

Schotte et al. Five-membered Disulfide Ring System. I. General Chemistry and Therapeutic Aspects. Biochemical Pharmacology. (1962). 11. ABSTRACT.
Thomas et al. Campthotecin: Current Perspectives. Bioorg Med Chem. (2004): 12: pp. 1585-1604. ABSTRACT.
U.S. Appl. No. 12/995,125 Restriction Requirement dated Jun. 7, 2012.
International PCT Search Report and Written Opinion dated Jul. 1, 2008 for PCT/US2008/055465.
International Preliminary Report on Patentability dated Sep. 1, 2009 for PCT/US2008/055465.
European publication No. 2125775 published Dec. 2, 2009, abstract corresponds to WO/2008/106640.
International PCT Search Report and Written Opinion dated Feb. 27, 2009 for PCT/US2008/088541.
International Preliminary Report on Patentability dated Jul. 6, 2010 for PCT/US2008/088541.
International PCT Search Report and Written Opinion dated Jun. 10, 2009 for PCT/US2009/039956.
International Preiminary Report on Patentability dated Dec. 6, 2010 for PCT/US2009/039956.
International PCT Search Report and Written Opinion dated Jan. 21, 2010 for PCT/US2009/065776.
International Preliminary Report on Patentability dated May 24, 2011 for PCT/US2009/065776.
Abaza et al., Effects of amino acid substitutions outside and antigenic site on protein binding to monoclonal antibodies of predetermined specificity obtained by peptide immunization: demonstration with region 94-100 (antigenic site 3) of myoglobin, Journal of Protein Chemistry, vol. 11, No. 5, 1992, pp. 433-444.
Colman, P.M. Effects of amino acid sequence changes on antibody-antigen interactions, Biomolecular Research Institute, 343 Royale Parade, Parkville, 3052 (Australia), Research in Immunology, No. 1, vol. 145, 1994, pp. 33-35.
Di Stefano, et al., Antiparkinson Prodrugs, Molecules, Jan. 16, 2008, vol. 13, pp. 46-68.
Lederman et al., A single amino acid substitution in a common african allele of the CD4 molecule ablates binding of the monoclonal antibody, OKT4, Molecur Immunology, vol. 28, No. 11, pp. 1171-1181, 1991.
Van Regenmortel, Marc H.V., Mapping epitope structure and activity: from one-dimensional prediction to four-dimensional description of antigenic specifity, Methods: A Companion to Methods in Enzymology 9, (1996), pp. 465-472.
Pham et al., Thermodynamic and structural characterization of 2-nitrogen-modified RNA duplexes, Nucleic Acids Research, 2004, vol. 32, No. 11, pp. 3446-3455.
Conklin, Cancer chemotherapy and antioxidants, J. Nutri., 2004, vol. 134, pp. 3201A-3204A.
U.S. Appl. No. 12/528,067 Notice of Allowance dated Jul. 16, 2012.
U.S. Appl. No. 12/811,197 Restriction Requirement dated Jul. 17, 2012.
U.S. Appl. No. 12/811,197 Non-Final Office Action dated Dec. 5, 2012.
U.S. Appl. No. 12/995,125 Non-Final Office Action dated Oct. 12, 2012.
EP Application No. 09828387.2 Supplemental Search Report dated Aug. 10, 2012.
Kunii et al. Preparation and antitumor characteristics of PLA/(PEG-PPG-PEG) nanoparticles loaded with camptothecin. European Journal of Pharmaceuticals and Biopharmaceuticals. (2007) 67(1):9-17.
U.S. Appl. No. 12/811,197 Non-Final Office Action dated Jul. 11, 2013.
U.S. Appl. No. 12/995,125 Final Office Action dated May 9, 2013.
Gruzman et al. Synthesis and characterization of new and potent a-lipoic acid derivatives. Bioorganic & Meidcal Chemistry (2004). 12:1183-1190.

* cited by examiner

ANTIOXIDANT CAMPTOTHECIN DERIVATIVES AND ANTIOXIDANT ANTINEOPLASTIC NANOSPHERES THEREOF

CROSS-REFERENCE TO RELATED APPLICATIONS

This application is a continuation-in-part of International Application PCT/US2009/65776, filed Nov. 24, 2009, which designated the United States and that International Application was published under PCT Article 21(2) in English. This application also includes a claim of priority under 35 U.S.C. §119(a) U.S. Provisional Application No. 61/117,299 filed Nov. 24, 2008.

FIELD OF INVENTION

This invention relates to antioxidant camptothecin derivatives and nanospheres thereof.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Antineoplastic Effect of Camptothecin

Camptothecin is a plant alkaloid first isolated from the wood and barks of Camptotheca acuminate (Nyssaceae), and exhibits its antineoplastic effect by the inhibition of DNA relaxation by DNA topoisomerase I. However, camptothecin is essentially insoluble in water, and therefore, numerous derivatives have been developed to increase the water solubility (Thomas et al., *Camptothecin: Current perspectives*. BIOORG. MED. CHEM., 12, 2004, 1585-1604: Pizzolato et al., *The Camptothecin*. THE LANCET, 361, 2003, 2235-2242).

Camptothecin consists of a pentacyclic structure having a lactone in the E-ring, which is essential for antitumor effects of the molecule. It has been demonstrated that the main transformation and elimination pathways of the drug comprise lactone hydrolysis and urinary excretion. In fact, the lactone form is 50% hydrolyzed to an open ring 30 minutes after administration. The sodium salt showed a lower activity than camptothecin, because at pH 7.4 the inactive form (open ring) predominates on the lactone active form (closed ring).

Antioxidant Effect of α-Lipoic Acid

Molecules containing a dithiolane moiety are widely investigated due to their antioxidant properties. α-Lipoic acid (thioctic acid, 1,2-dithiolane-3-pentanoic acid), which has dithiolane ring in its molecule, is a widely distributed natural substance which was originally discovered as a growth factor. Physiologically, it acts as a coenzyme of the oxidative decarboxylation of α-keto carboxylic acid (e.g., pyruvates) and as an antioxidant, and it is able to regenerate vitamin C, vitamin E, glutathione and coenzyme Q10. In pathological conditions, lipoic acid is applied in the treatment of diabetic polyneuropathy, liver cirrhosis and metal intoxications.

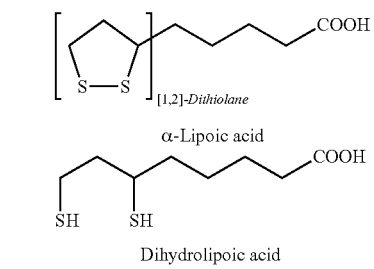

Lipoic acid and dihydrolipoic acid are capable of trapping a number of radicals both in a lipid and in an aqueous environment. Lipoic acid and dihydrolipoic acid act as antioxidants not only by direct radical trapping and/or metal chelation but also by recycling other antioxidants (e.g., vitamin C, vitamin E) and by reducing glutathione, which in turn recycles vitamin E. The two thiol groups present in [1,2]-dithiolane ring system confer it a unique antioxidant potential. The disulfides with a cyclic five-member ring such as lipoic acid have been found to be more effective in reductive and/or nucleophilic attack than open-chain derivatives such as cystine or glutathione.

The antioxidant potential of a compound may be evaluated based on the properties such as (1) specificity of free radical scavenging, (2) interaction with other antioxidants, (3) metal-chelating activity, (4) effects on gene expression, (5) absorption and bioavailability, (6) location (in aqueous or membrane domains, or both), and (7) ability to repair oxidative damage (Packer et al., FREE RADICAL BIOLOGY & MEDICINE. 19(2): 227-250, 1995). According to the above criteria, the [1,2]-dithiolane containing lipoic acid/dihydrolipoic acid redox system has been regarded as a universal antioxidant.

There have been many attempts to develop lipoic acid derivatives or complexes having antioxidant activity. U.S. Pat. Nos. 6,090,842; 6,013,663; 6,117,899; 6,127,394; 6,150,358; 6,204,288, 6,235,772; 6,288,106; 6,353,011; 6,369,098; 6,387,945; 6,605,637; 6,887,891; 6,900,338; and 6,936,715 are some examples.

In many other U.S. patents, the natural and synthetic lipoic acid derivatives and their metabolites are disclosed for use in preventing skin aging and in the treatment of free radical mediated diseases, including inflammatory, proliferative, neurodegenerative, metabolic and infectious diseases.

Inhibitory Activity on NO-Synthase and Trapping the Reactive Oxygen Species (ROS)

Various conditions or disease conditions have demonstrated a potential role of nitric oxide (NO) and the ROS's and the metabolism of glutathione in their physiopathology. Conditions or disease conditions where nitrogen monoxide and the metabolism of glutathione as well as the redox status of thiol groups are involved include but are not limited to: cardiovascular and cerebrovascular disorders (e.g., atherosclerosis, migraine, arterial hypertension, septic shock, ischemic or hemorrhagic cardiac or cerebral infarctions, ischemias and thromboses); disorders of the central or peripheral nervous system (e.g., neurodegenerative nervous system); neurodegenerative diseases including cerebral infarctions, sub-arachnoid hemorrhaging, ageing, senile dementias (e.g., Alzheimer's disease), Huntington's chorea, Parkinson's disease, prion disease (e.g., Creutzfeld Jacob disease), amyotrophic lateral sclerosis, pain, cerebral and spinal cord traumas; proliferative and inflammatory diseases (e.g., atherosclerosis), amyloidoses, and inflammations of the gastro-intestinal system; organ transplantation; diabetes and its complications (e.g., retinopathies, nephropathies and polyneuropathies, multiple sclerosis, myopathies); cancer; autosomal genetic diseases (e.g., Unverricht-Lundborg disease); neurological diseases associated with intoxications (e.g., cadmium poisoning, inhalation of n-hexane, pesticides, herbicides), associated with treatments (e.g., radiotherapy) or disorders of genetic origin (e.g., Wilson's disease); and impotence linked to diabetes.

These conditions and disease conditions are characterized by an excessive production or a dysfunction of nitrogen monoxide and/or the metabolism of glutathione and of the redox status of the thiol groups (Duncan and Heales, *Nitric Oxide and Neurological Disorders*, MOLECULAR ASPECTS OF MEDICINE. 26:67-96, 2005; Kerwin et al., *Nitric Oxide: A New Paradigm For Second Messengers*, J. MED. CHEM. 38:4343-4362, 1995; Packer et al., FREE RADICAL BIOLOGY & MEDICINE. 19:227-250, 1995). U.S. Pat. Nos. 6,605,637, 6,887,891, and 6,936,715 disclose that lipoic acid derivatives inhibit the activity of NO-synthase enzymes producing nitrogen monoxide NO and regenerate endogenous antioxidants which trap the ROS and which intervene in a more general fashion in the redox status of thiol groups. U.S. Pat. Nos. 5,693,664, 5,948,810, and 6,884,420 disclose the use of racemic α-lipoic acid or their metabolites, salts, amides or esters for the synthesis of drugs for the treatment of diabetes mellitus of types I and II. U.S. Pat. No. 5,925,668 discloses a method of treating free radical mediated diseases, and/or reducing the symptoms associated with such diseases whereby the compounds with antioxidant activity contain 1,2-dithiolane, reduced or oxidized forms. U.S. Pat. No. 6,251,935 discloses methods for the prevention or treatment of migraine comprising the administration of an active ingredient selected from the group consisting of racemic alpha-lipoic acid, enantiomers and pharmaceutically acceptable salts, amides, esters or thioesters thereof. U.S. Pat. Nos. 6,472,432 and 6,586,472 disclose the treatment of a chronic inflammatory disorder rosacea by application of a composition containing lipoic acid and/or lipoic acid derivatives. There is also strong evidence that the neuroprotective effects of lipoic acid and dihydrolipoic acid are mediated by antioxidant and free radical scavenging mechanisms (Packer et al., FREE RADICAL BIOLOGY & MEDICINE. 22:359-378, 1997).

SUMMARY OF THE INVENTION

The following embodiments and aspects thereof are described and illustrated in conjunction with compositions and methods which are meant to be exemplary and illustrative, not limiting in scope.

One embodiment of present invention provides for a compound comprising:

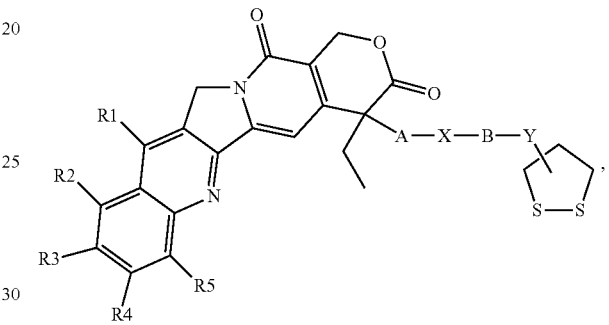

Formula II wherein A and B may be independently selected from the group consisting of —OC(O)—, —OC(O)O—, and —OC(O)N(R)—, wherein R may be a hydrogen atom, or a substituted, unsubstituted, branched or unbranched chain of carbon atoms; X and Y may be linkers, each independently comprising a substituted, unsubstituted, branched or unbranched chain of carbon atoms and may optionally contain a heteroatom; and $R_1$, $R_2$, $R_3$, $R_4$, and $R_5$ may each be independently selected from the group consisting of hydrogen, alkyl, aryl, cycloaliphatic, and aralkyl and may each optionally contain a hetero atom.

In one embodiment, the compound may be represented by

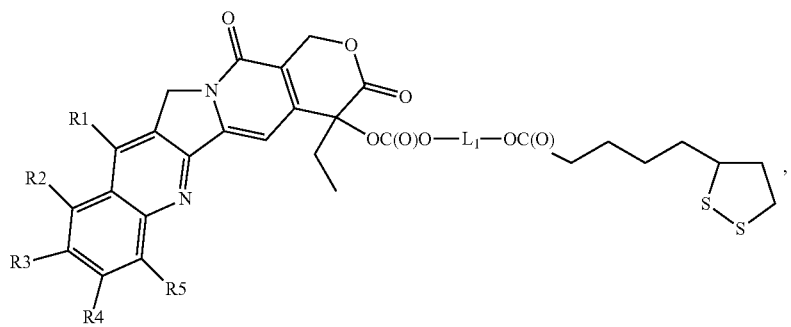

Formula IV wherein $L_1$ may be a moiety formed by esterification of two free esterifiable hydroxyl groups on a diol; and $R_1$, $R_2$, $R_3$, $R_4$, and $R_5$ may each be independently selected from the group consisting of hydrogen, alkyl, aryl, cycloaliphatic, and aralkyl group, and may optionally contain a hetero atom.

In various embodiments, the diol may be selected from the group consisting of: HO—W—OH wherein W is a hydrocarbon group,

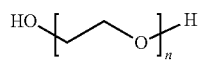

wherein n is an integer between 1 and 100,

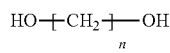

wherein n is an integer between 2 and 12,

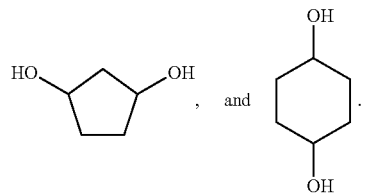

In various embodiments, the compound may be selected from the group consisting of:

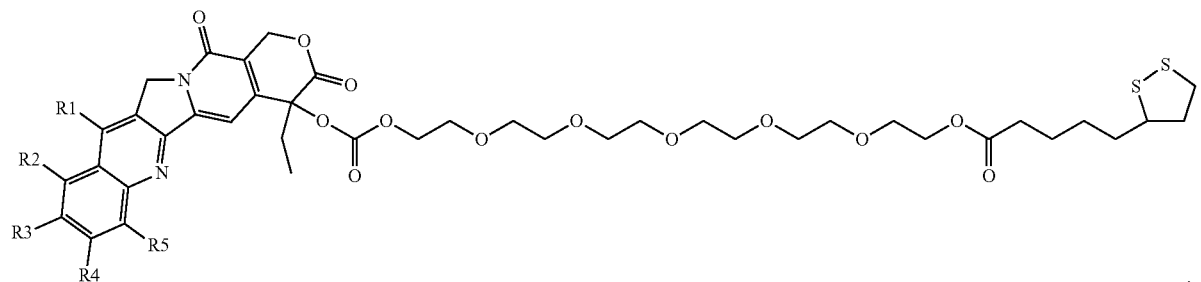

Formula V

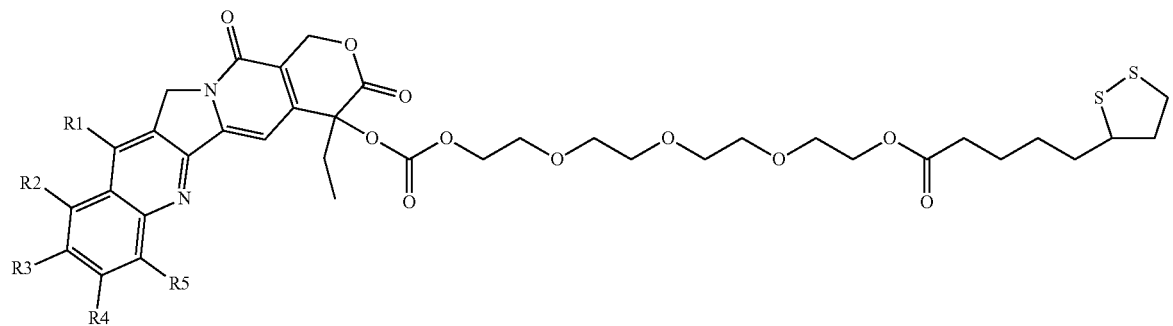

Formula VI

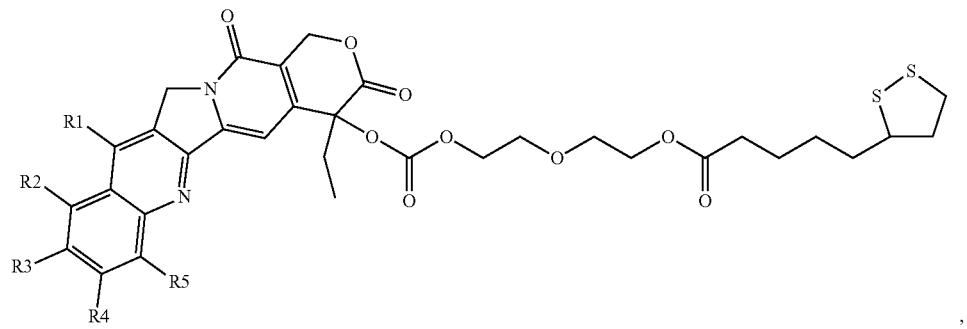

Formula VII

Formula VIII
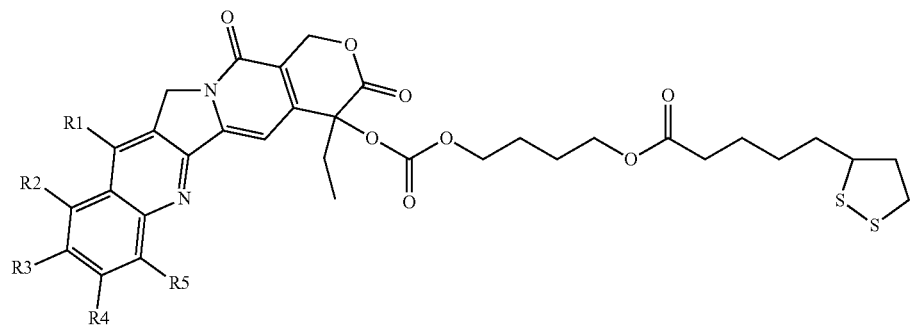
,
Formula IX
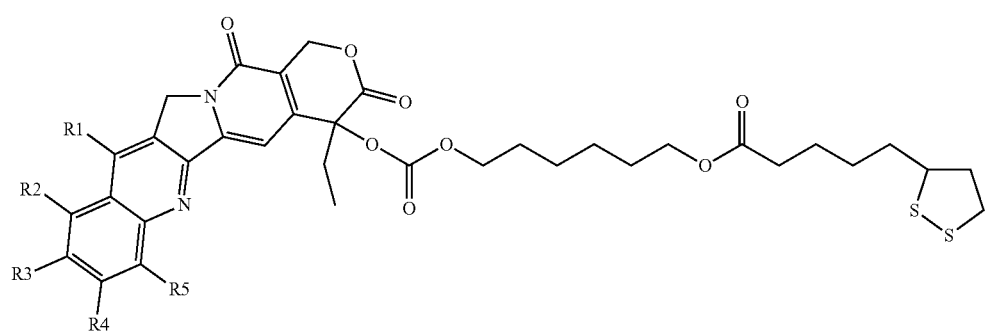
,
Formula X
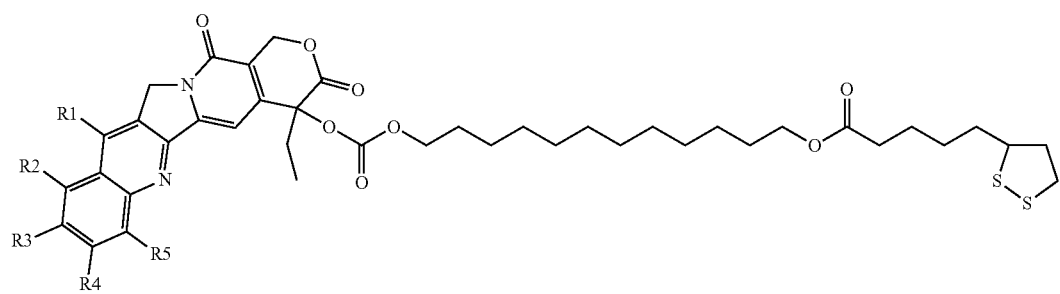
, and
Formula XLVI
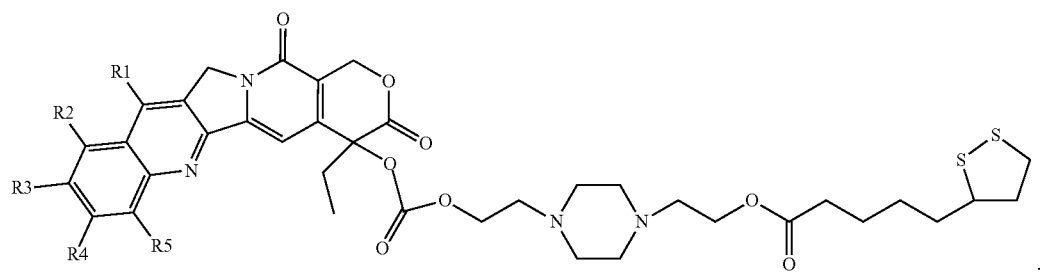
.

Another embodiment of the present invention also provides for a compound, comprising:

Formula III

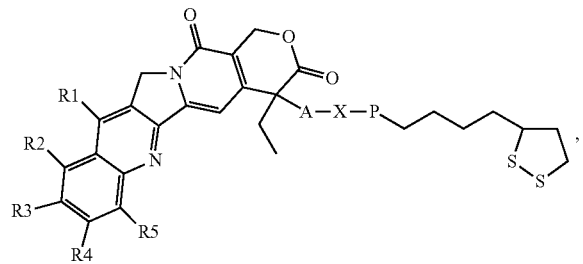

wherein A may be selected from the group consisting of —OC(O)—, —OC(O)O—, and —OC(O)N(R)—, wherein R may be a hydrogen atom, or a substituted, unsubstituted, branched or unbranched chain of carbon atoms; P may be selected from the group consisting of —OC(O)—, and —N(R)C(O)—, wherein R may be a hydrogen atom, or a substituted, unsubstituted, branched or unbranched chain of carbon atoms; X may be a linker comprising a substituted, unsubstituted, branched or unbranched chain of carbon atoms and may optionally contain a heteroatom; and $R_1$, $R_2$, $R_3$, $R_4$, and $R_5$ may each be independently selected from the group consisting of hydrogen, alkyl, aryl, cycloaliphatic, and aralkyl, and may each optionally contain a hetero atom.

In one embodiment, the compound may be

Formula XI

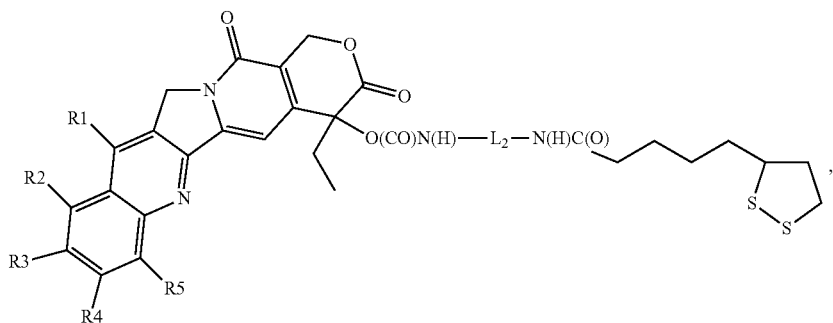

wherein $L_2$ may be a moiety formed by using a diamine as a linker in the process of producing the compound; and $R_1$, $R_2$, $R_3$, $R_4$, and $R_5$ may each be independently selected from the group consisting of hydrogen, alkyl, aryl, cycloaliphatic, and aralkyl group, and may optionally contain a hetero atom.

In various embodiments, the diamine may be selected from the group consisting of: $H_2N-X-NH_2$ wherein X is a hydrocarbon group,

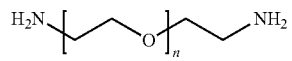

wherein n is an integer between 1 and 100, and

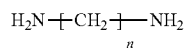

wherein n is an integer between 2 and 12.

In various embodiments, the compound may be selected from the group consisting of:

Formula XII

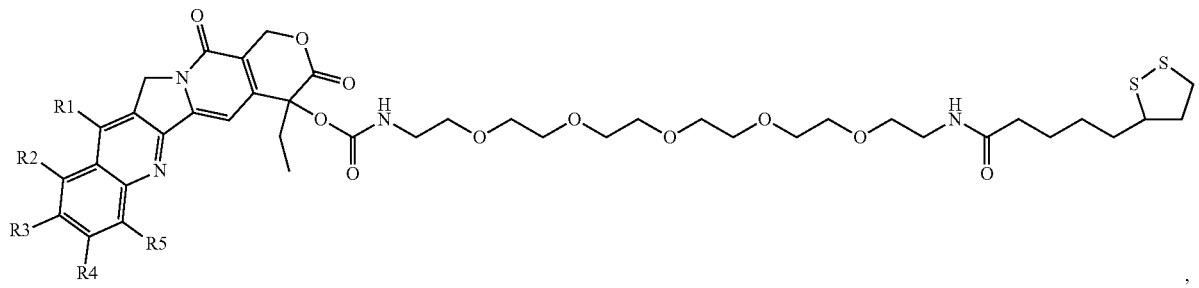

Formula XIII
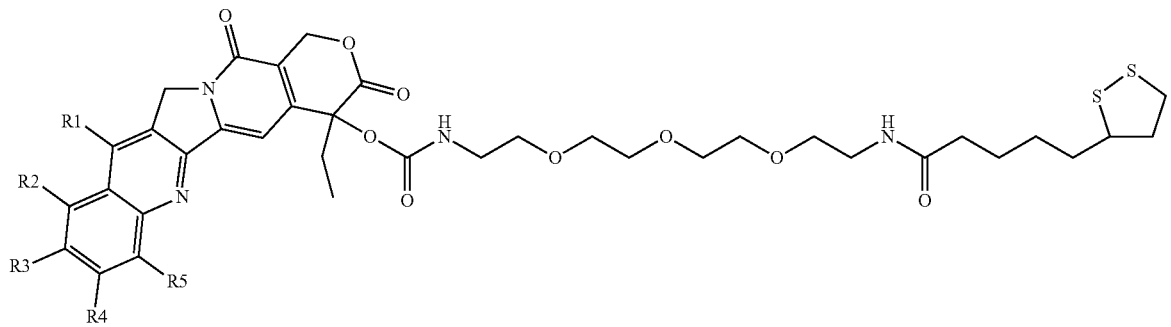
Formula XIV
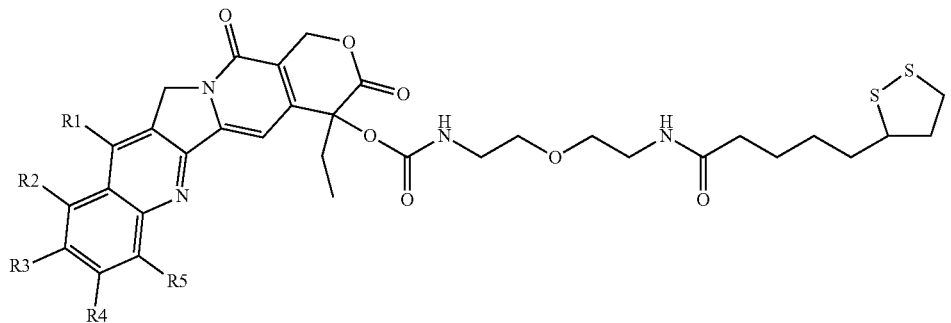
Formula XV
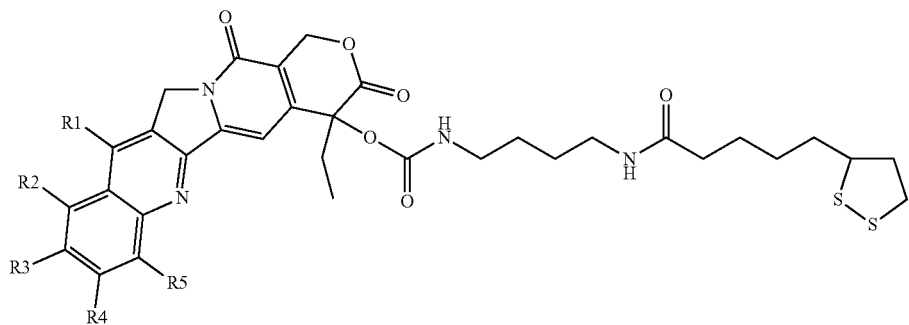
Formula XVI
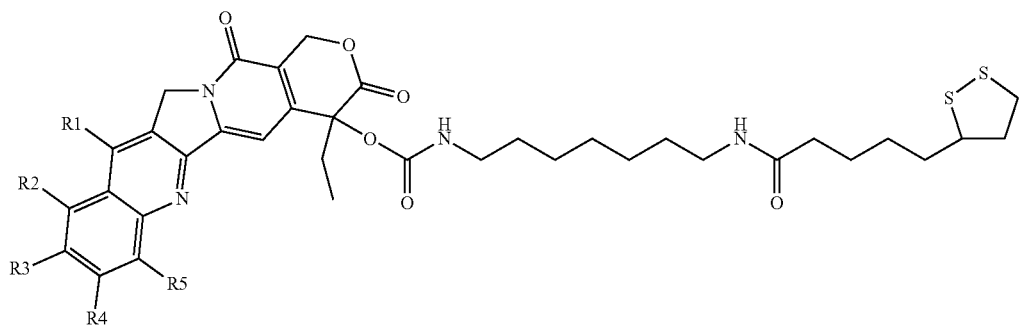

Formula XVII

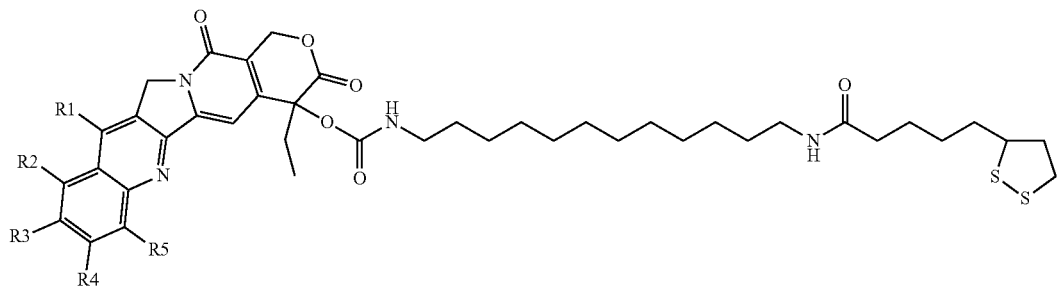

and

Formula XLVII

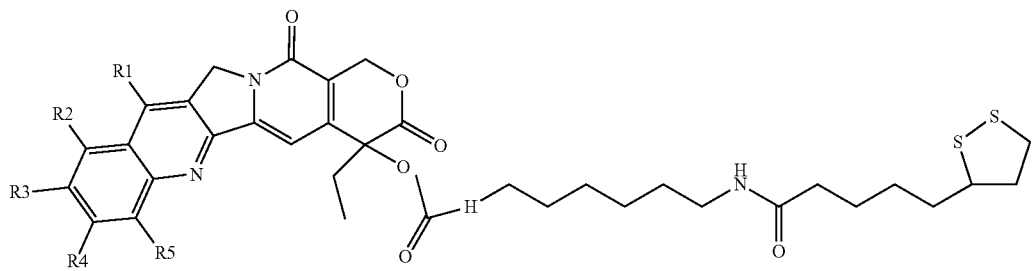

In various embodiments, the compound may be represented as follows:

Formula XVIII

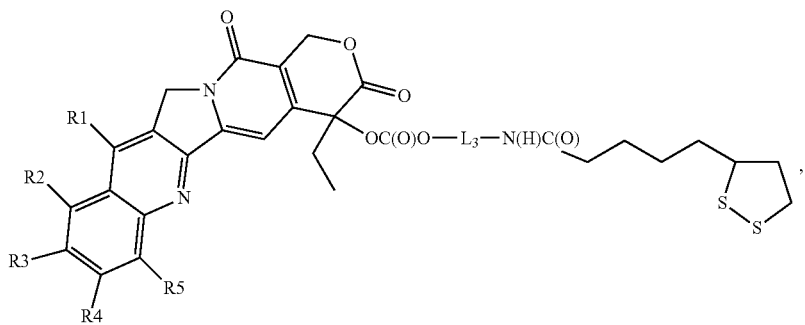

wherein $L_3$ may be a moiety formed by using an aminoalcohol as a linker in the process of producing the compound; and $R_1$, $R_2$, $R_3$, $R_4$, and $R_5$ are each independently selected from the group consisting of hydrogen, alkyl, aryl, cycloaliphatic, and aralkyl, and may each contain a hetero atom.

In various embodiments, the aminoalcohol may be selected from the group consisting of: $H_2N$—Y—OH wherein the Y is a hydrocarbon group, and may optionally contain a hetero atom,

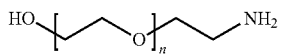

wherein n is an integer between 1 and 100, and

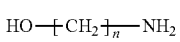

wherein n is an integer between 2 and 12.

In various embodiments, the compound may be selected from the group consisting of:

Formula XIX
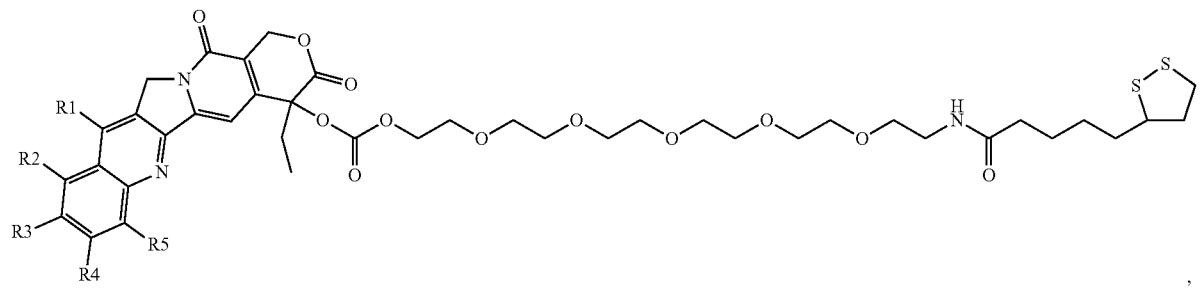
,
Formula XX
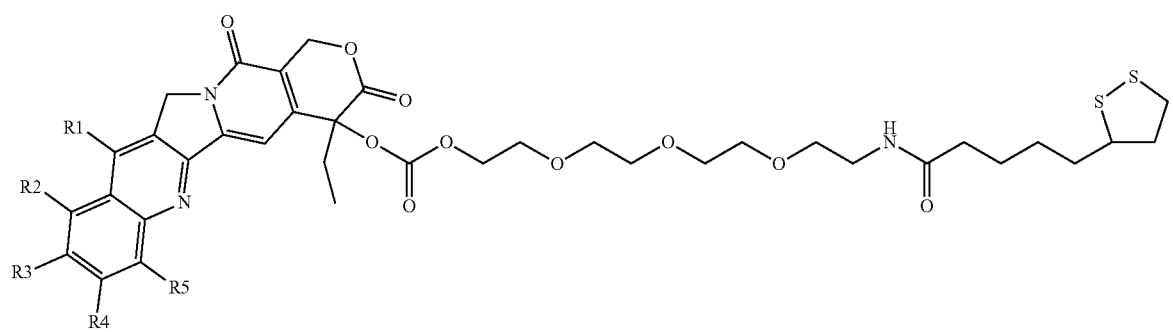
,
Formula XXI
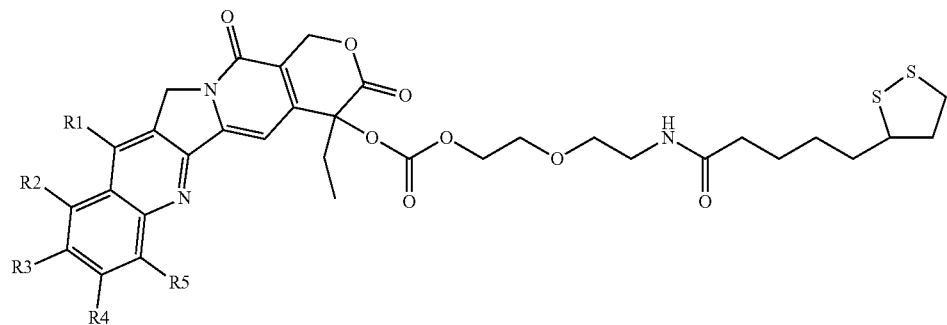
,
Formula XXII
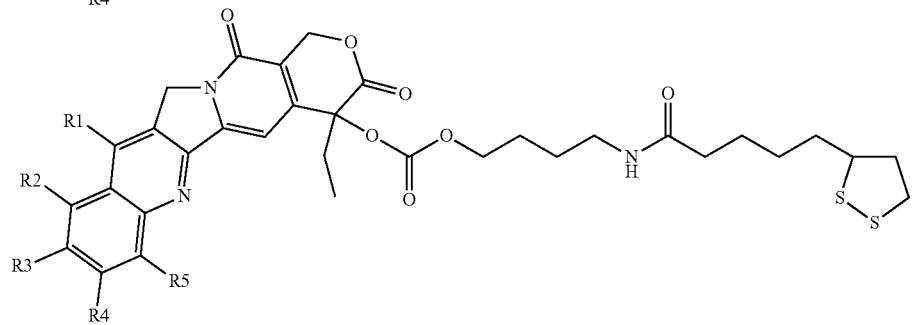
,
Formula XXIII
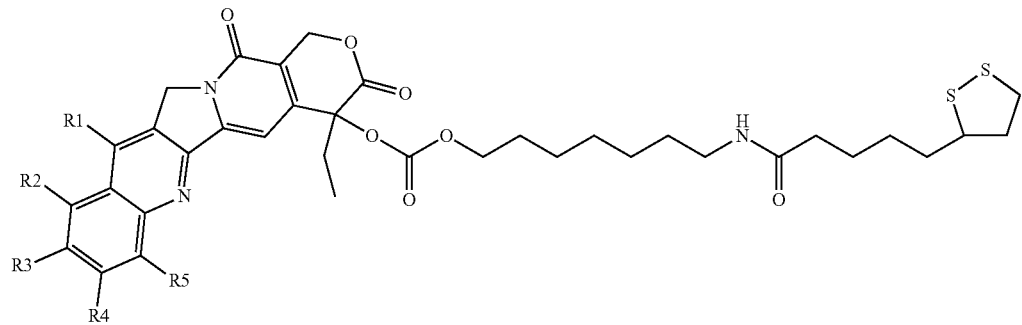
, -continued

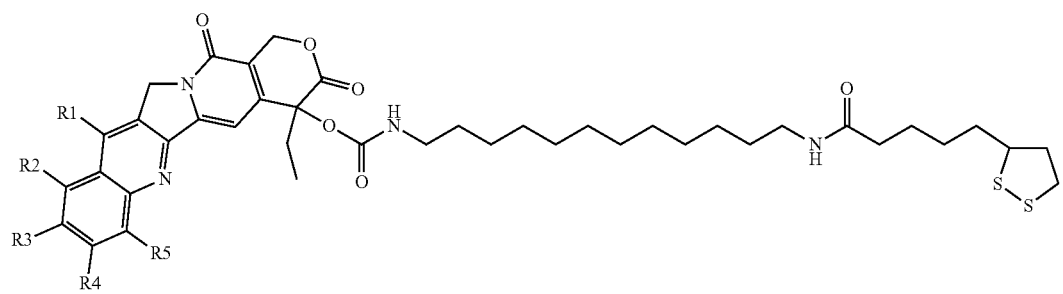

Formula XXIV

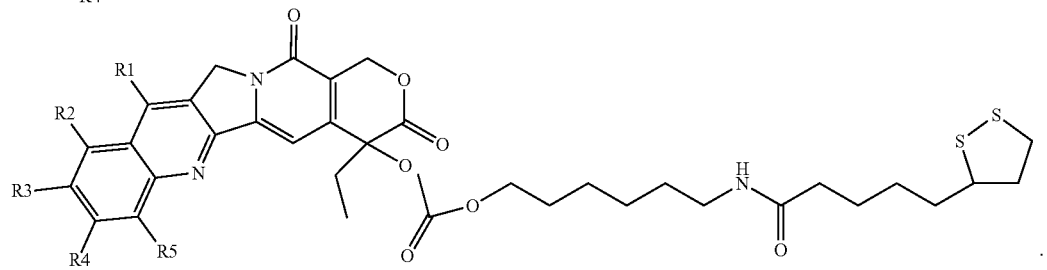

Formula XLVIII

Another embodiment of the present invention also provides for a compound produced by conjugation of an α-lipoic acid and camptothecin or a camptothecin analog modified by reacting with succinic anhydride or glutaric anhydride, wherein the camptothecin analog is represented by:

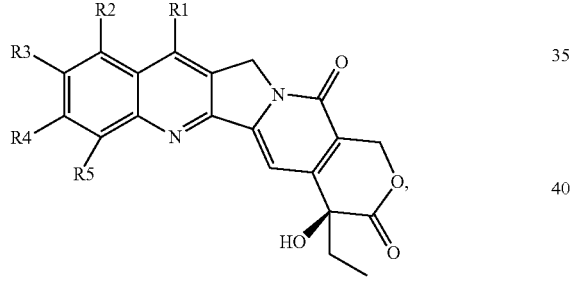

Formula I wherein $R_1$, $R_2$, $R_3$, $R_4$, and $R_5$ may each be independently selected from the group consisting of hydrogen, alkyl, aryl, cycloaliphatic, and aralkyl, and may optionally contain a hetero atom.

In various embodiments, the compound may be selected from the group consisting of:

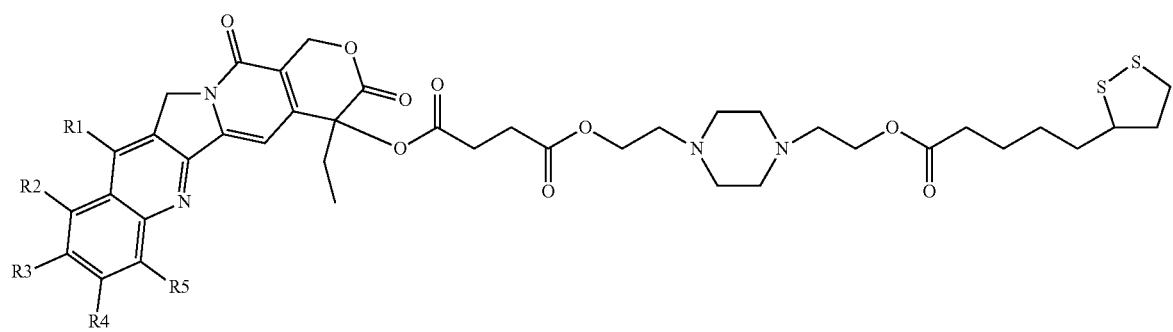

Formula XXV

-continued
Formula XXVI
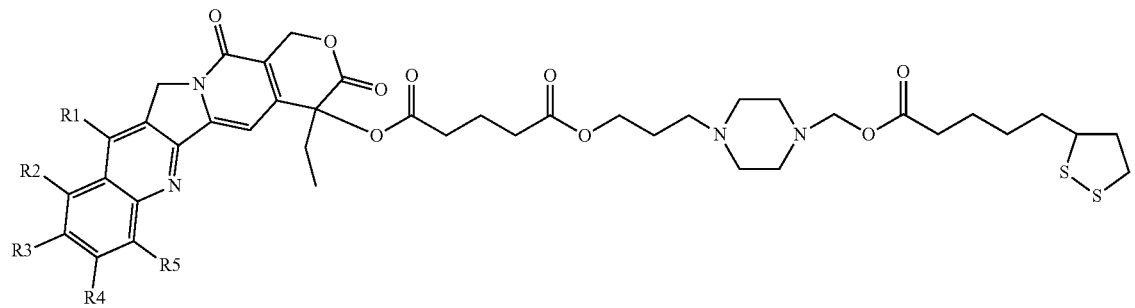
Formula XXVII
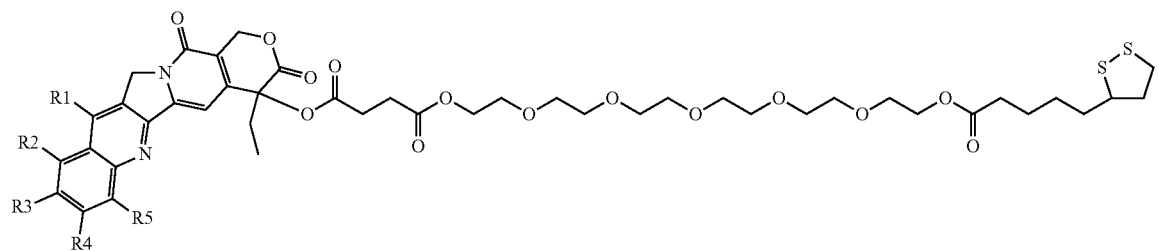
Formula XXVIII
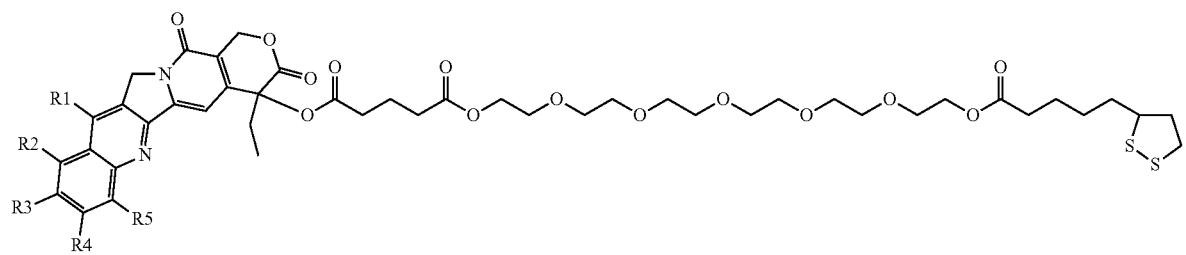
Formula XXIX
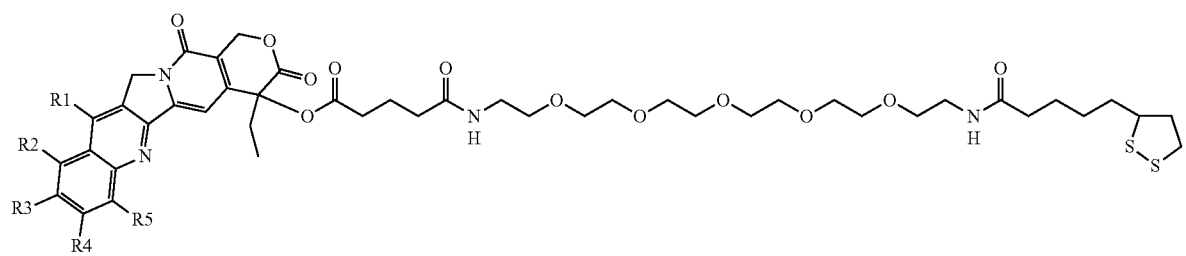
Formula XXX
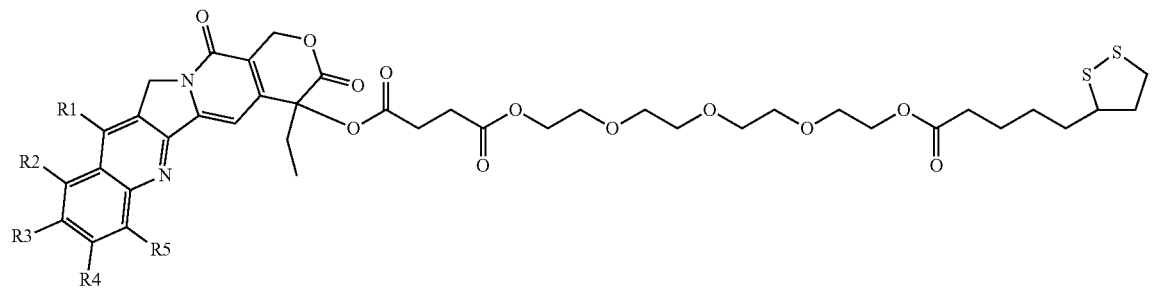

Formula XXXI
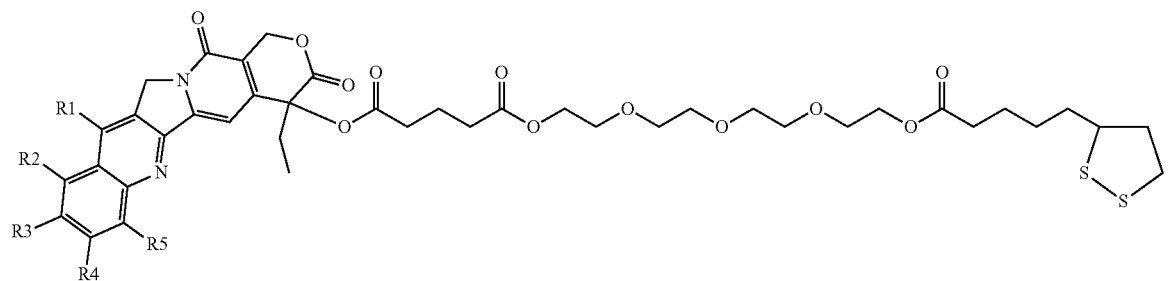
Formula XXXII
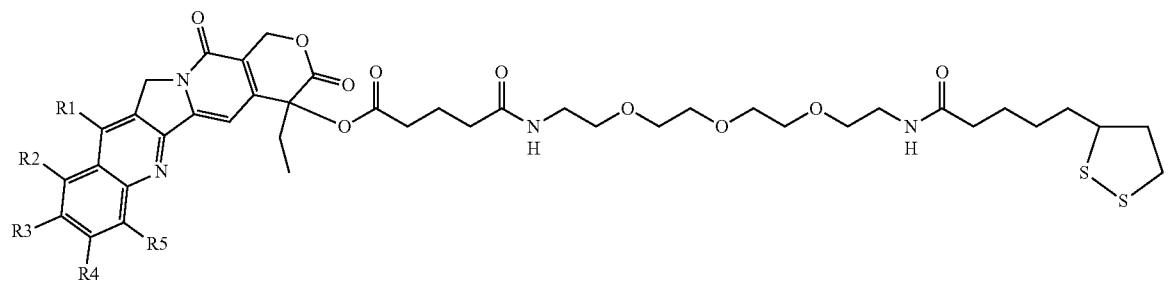
Formula XXXIII
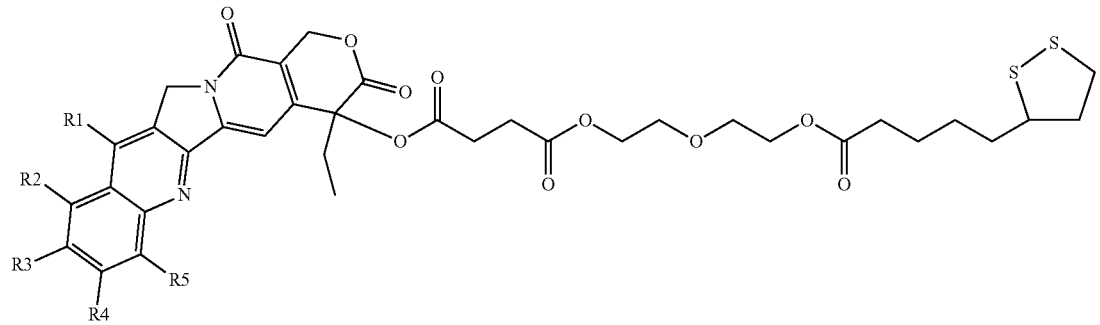
Formula XXXIV
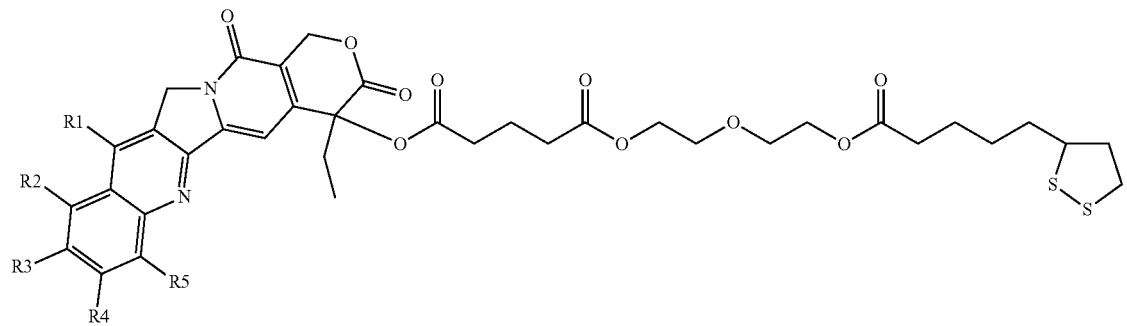

Formula XXXV
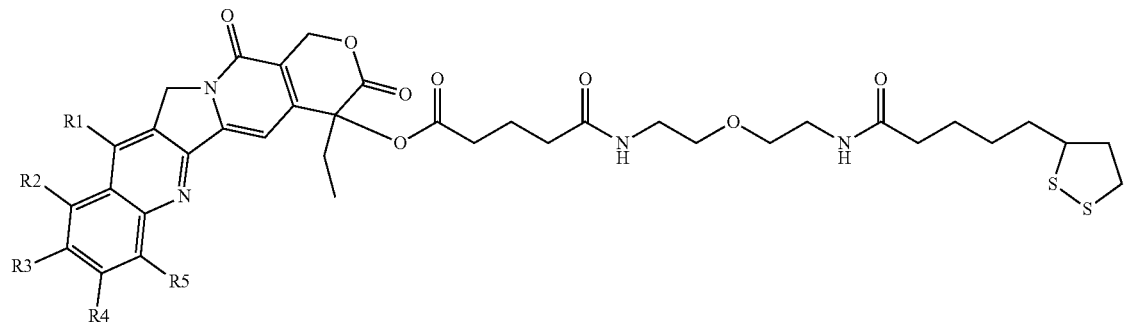
Formula XXVI
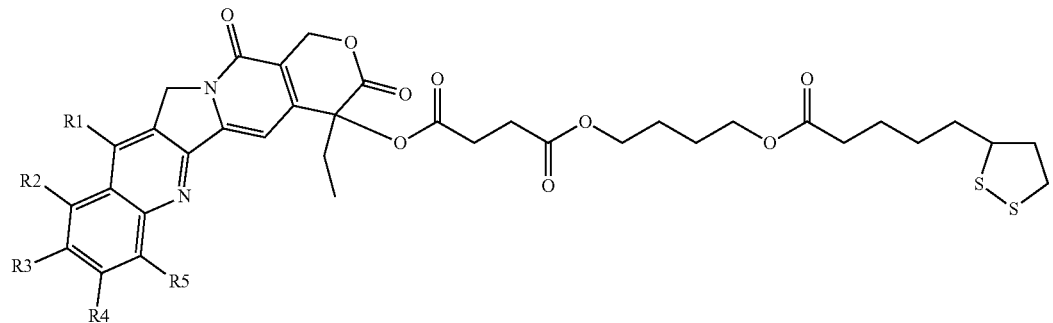
Formula XXXVII
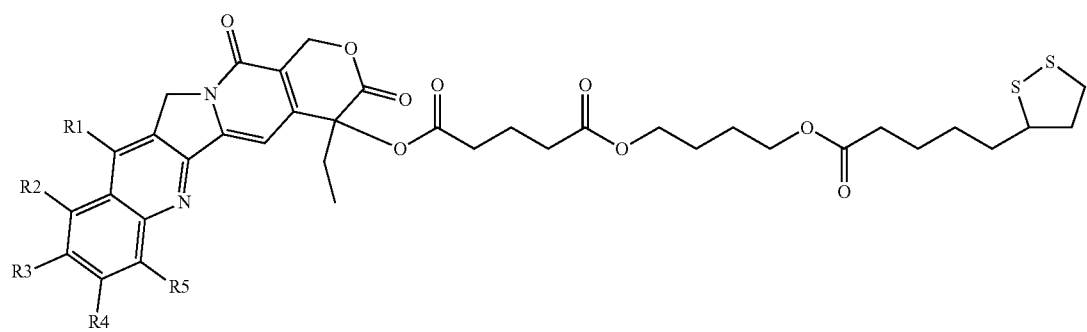
Formula XXXVIII
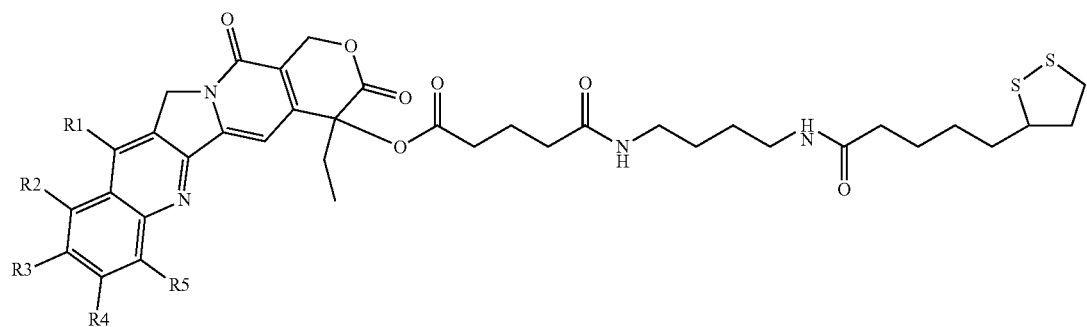

Formula XXXIX
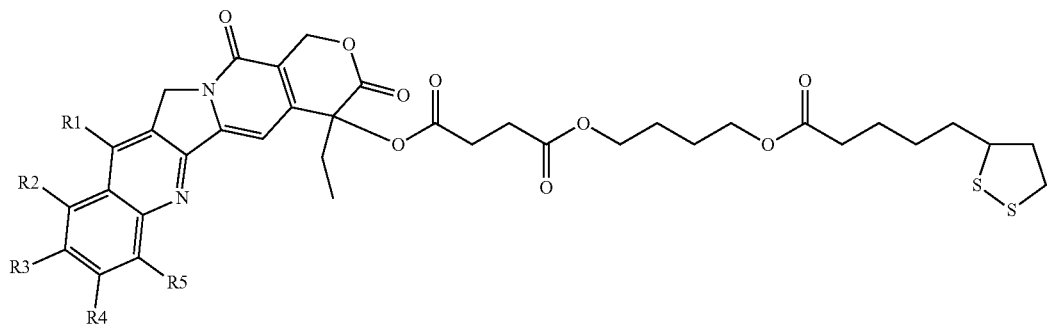
,
Formula XL
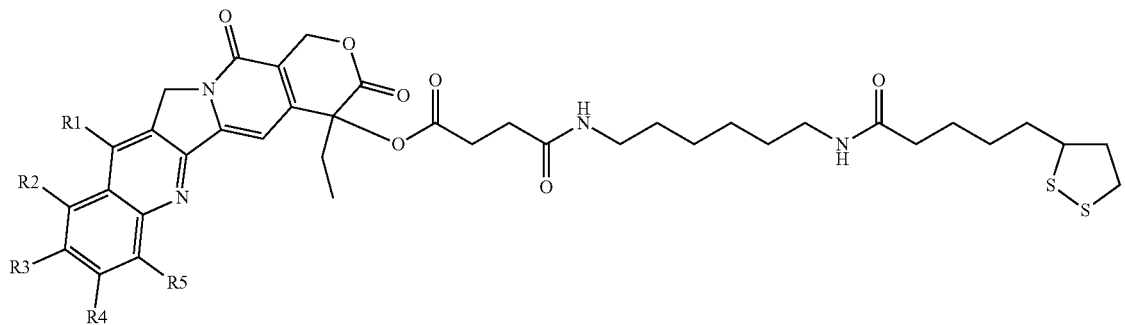
,
Formula XLI
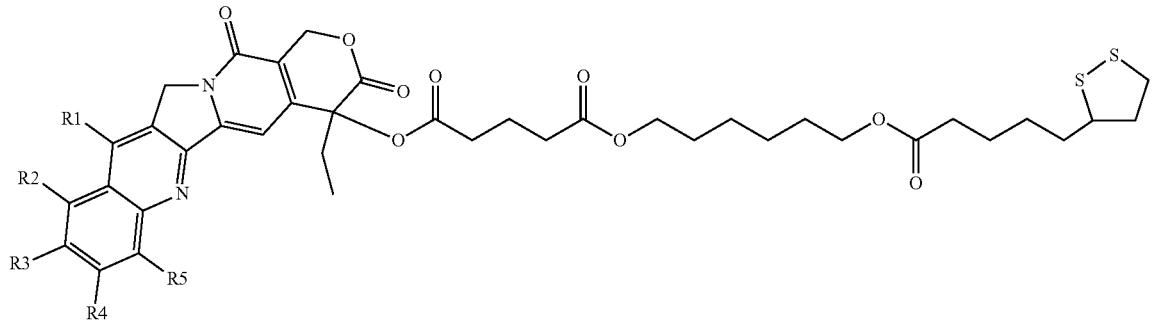
,
Formula XLII
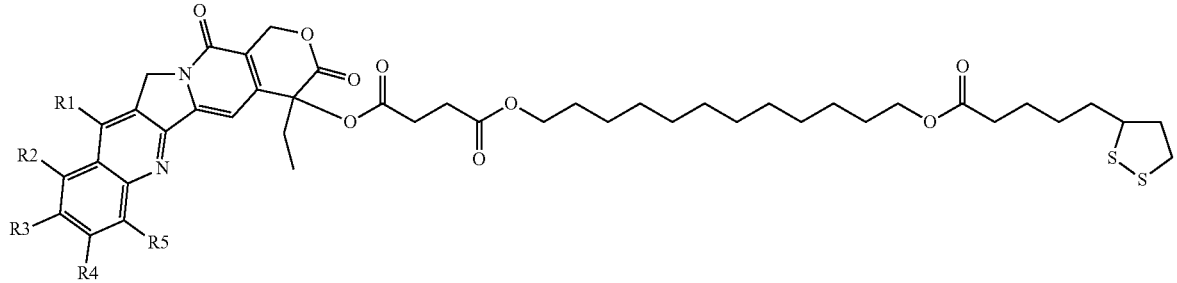
, Formula XLIII
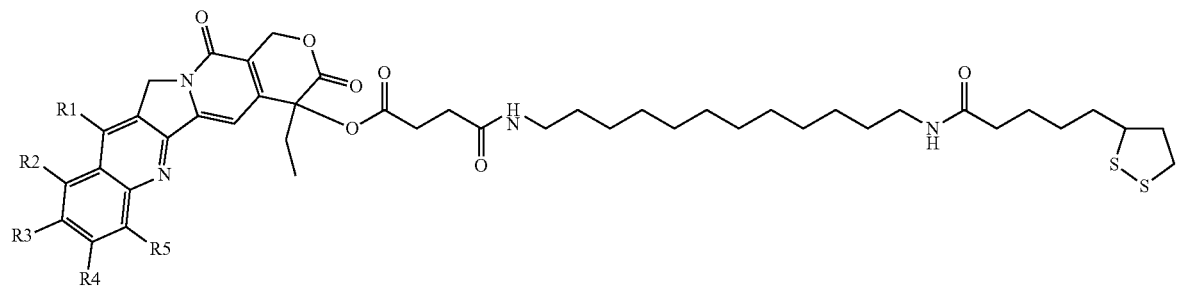
Formula XLIV
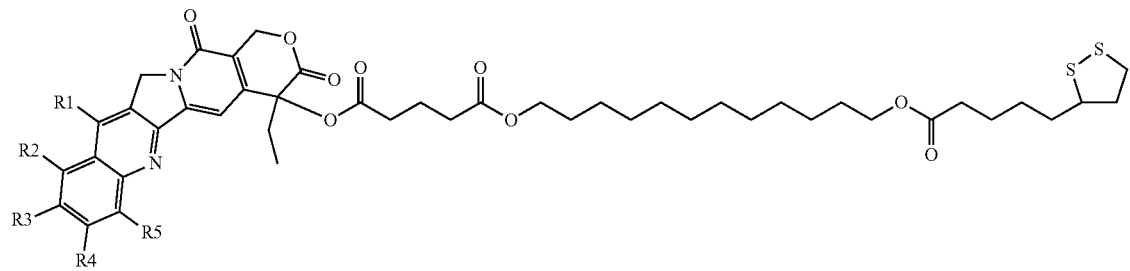
, and
Formula XLV
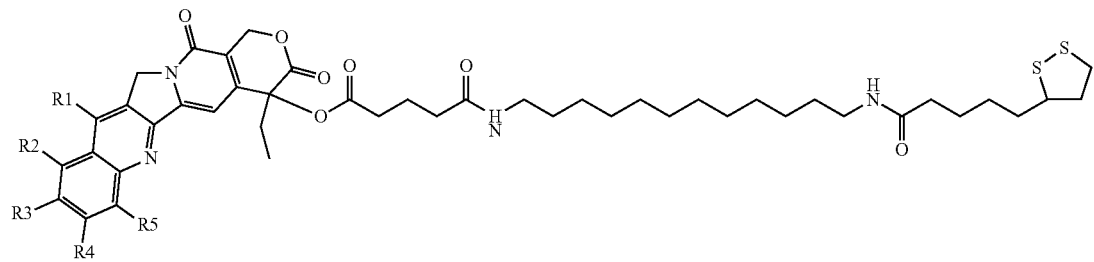
wherein $R_1$, $R_2$, $R_3$, $R_4$, and $R_5$ may each be independently selected from the group consisting of hydrogen, alkyl, aryl, cycloaliphatic, and aralkyl, and may optionally contain a hetero atom.
The present embodiments also provide for the following compounds:
Compound 23
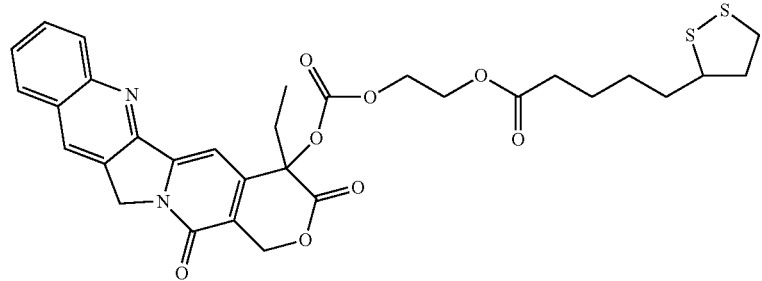

-continued
Compound 1
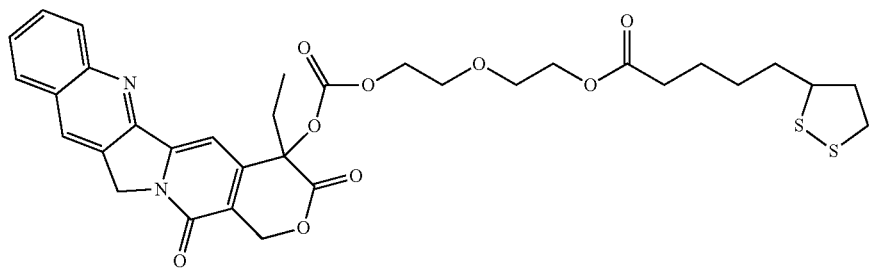
Compound 2
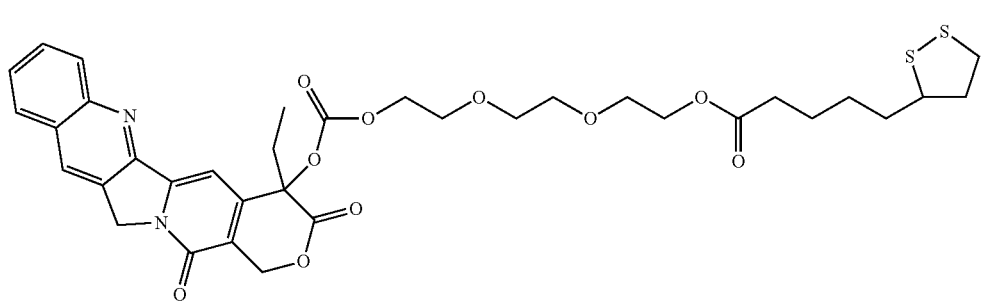
Compound 10
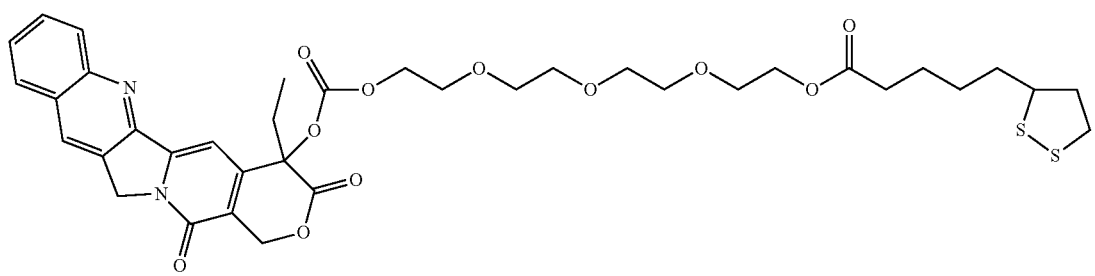
Compound 3
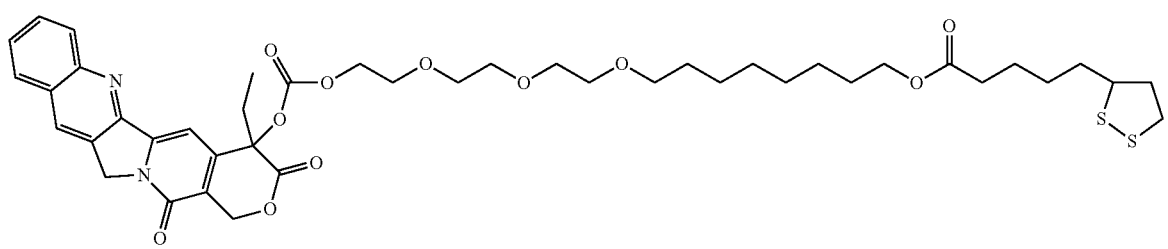
Compound 4
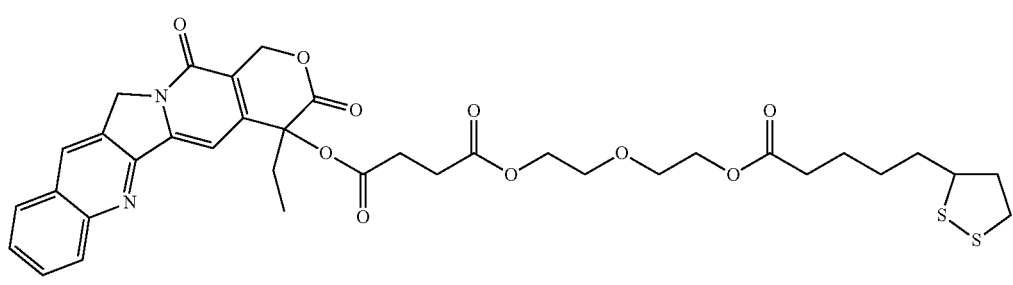

-continued
Compound 5
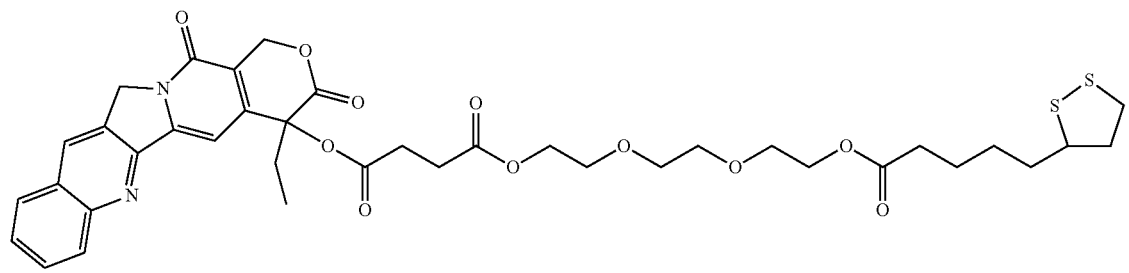,
Compound 11
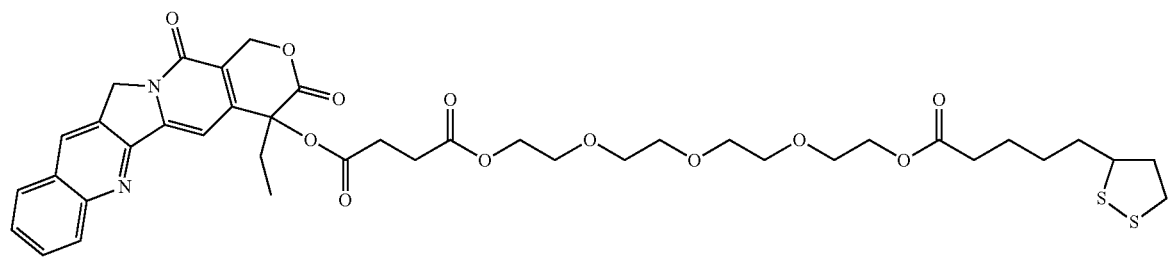,
Compound 6
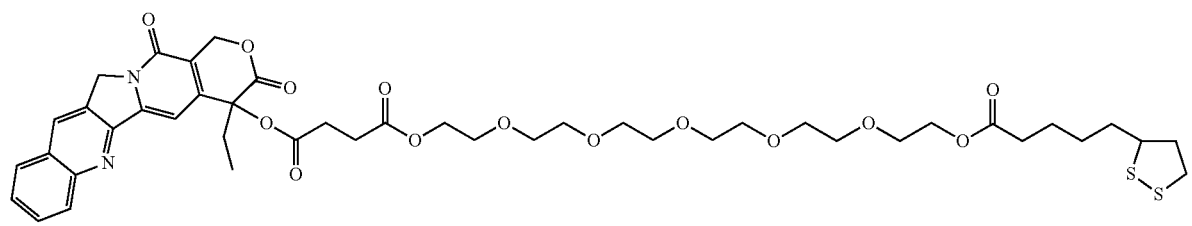,
Compound 7
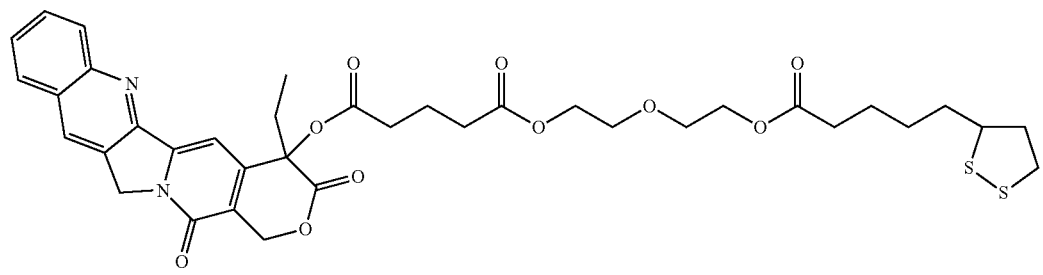,
Compound 8
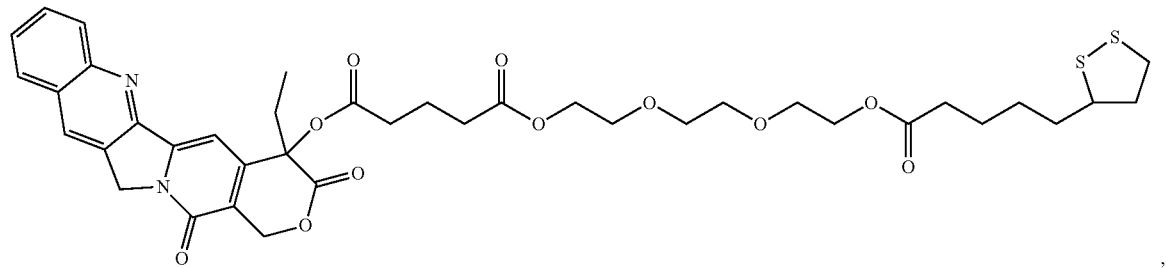, Compound 12
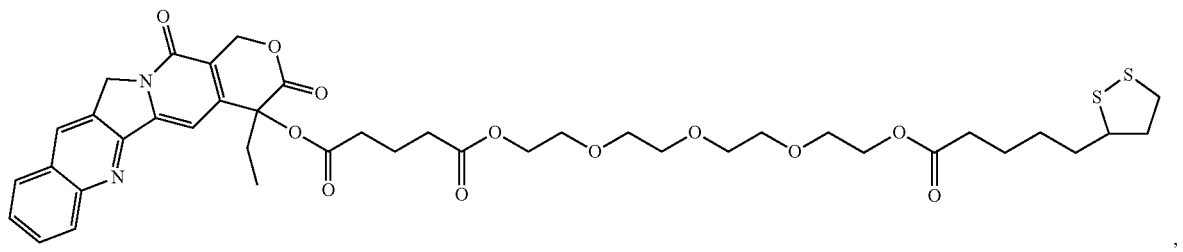
Compound 9
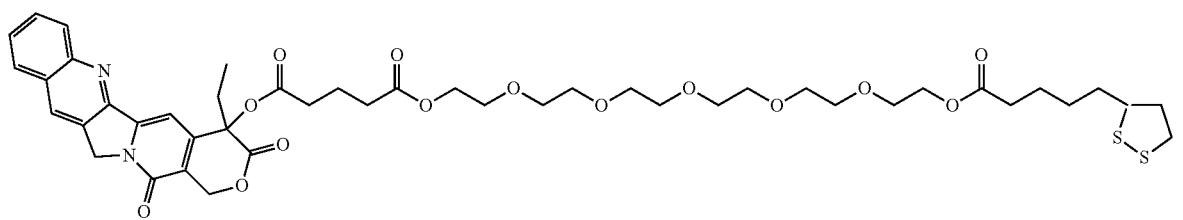
Compound 13
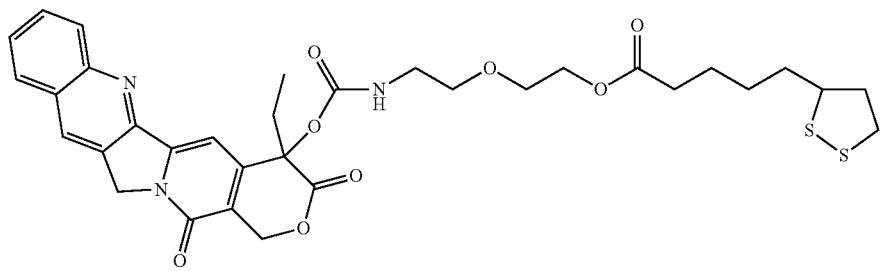
Compound 14
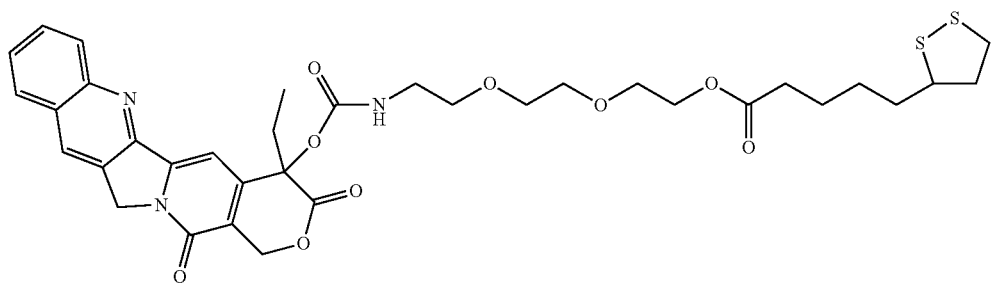
Compound 15
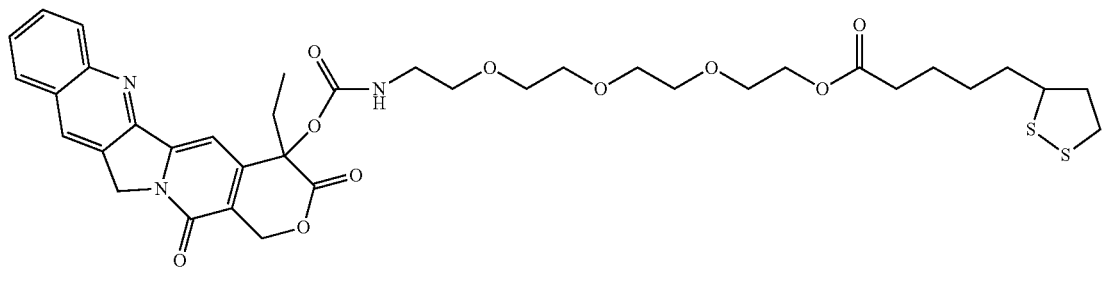

-continued
Compound 16
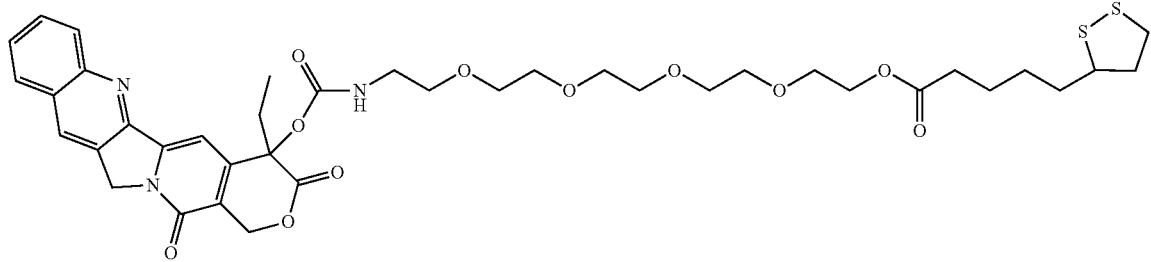
Compound 17
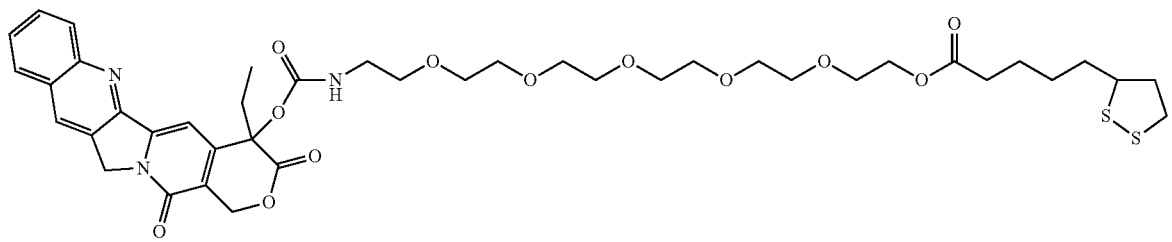
Compound 18
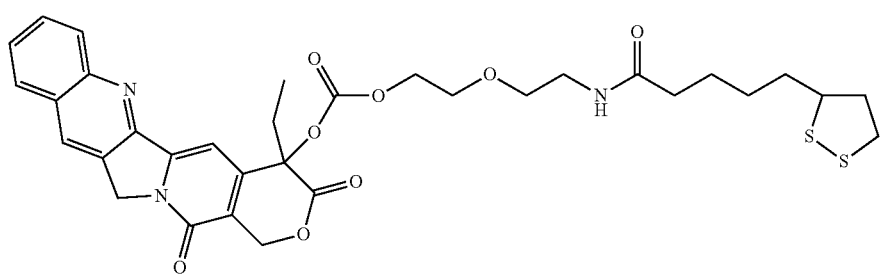
Compound 19
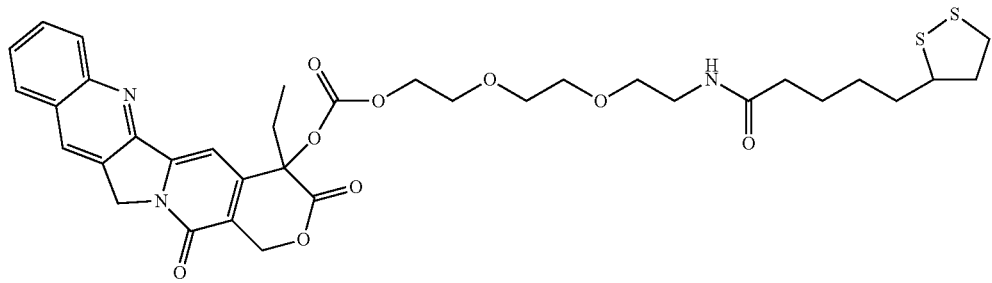
Compound 20
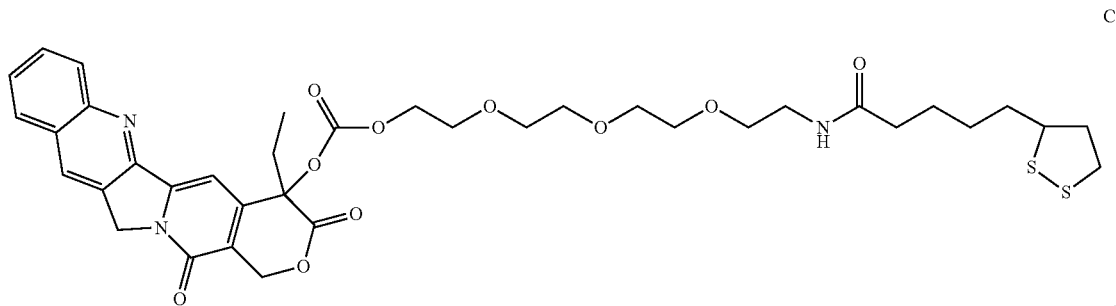

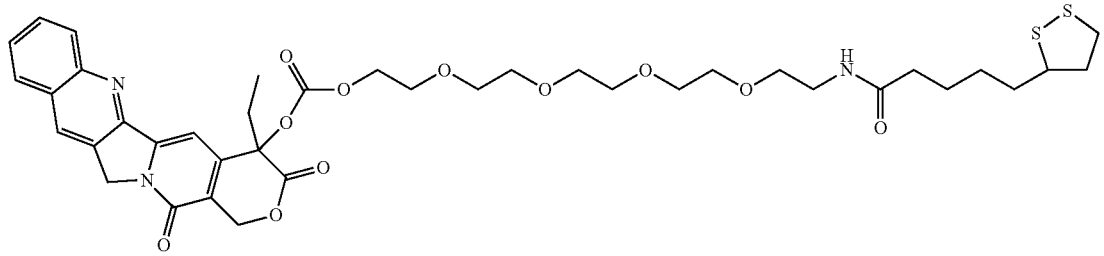

, Compound 21 and

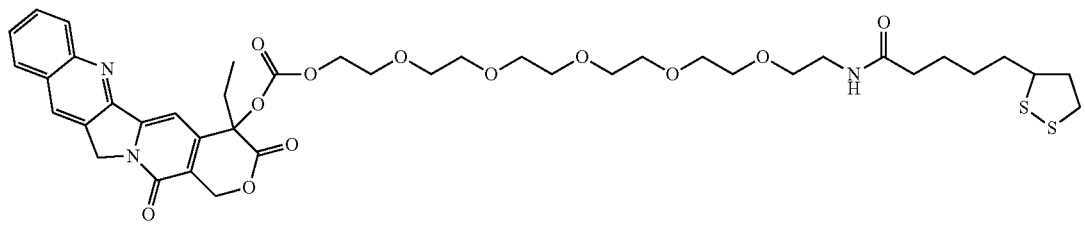

, Compound 22

The present invention also provides a nanosphere, comprising a compound of the present invention. In a further embodiment, the nanosphere may further comprise a compound selected from the group consisting of: a multiple α-lipoic acid-containing hydrophobic compound, α-tocopherol, a nonsteroidal anti-inflammatory drug (NSAID) derivative, and combinations thereof.

The present invention also provides for a method of treating cancer in a subject in need thereof, comprising: providing a composition comprising a compound of the present invention; and administering a therapeutically effective amount of the composition to the subject to treat the cancer.

The present invention also provides a method of treating cancer in a subject in need thereof, comprising: providing a nanosphere of the present invention; and administering a therapeutically effective amount of the nanosphere to the subject to treat the cancer.

The present invention also provides a pharmaceutical composition, comprising: a pharmaceutically acceptable carrier or excipient; and a compound of the present invention.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

Exemplary embodiments are illustrated in the referenced figures. It is intended that the embodiments and figures disclosed herein are to be considered illustrative rather than restrictive.

DESCRIPTION OF THE INVENTION

Figure 1:
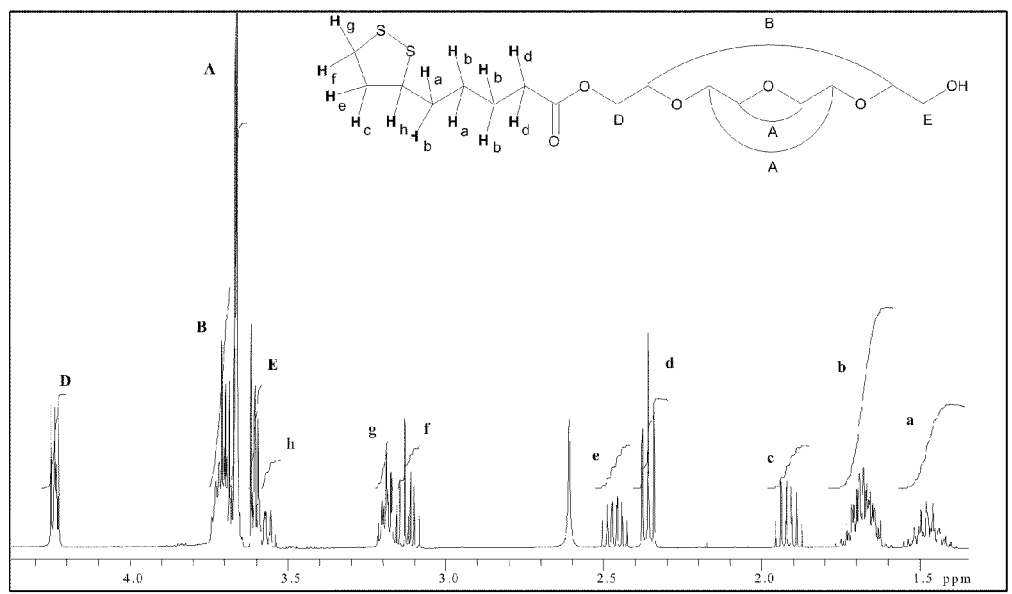
FIG. 1 depicts the $^1$H spectrum of the compound ALA-TEG-OH in accordance with an embodiment of the present invention.
Figure 2:
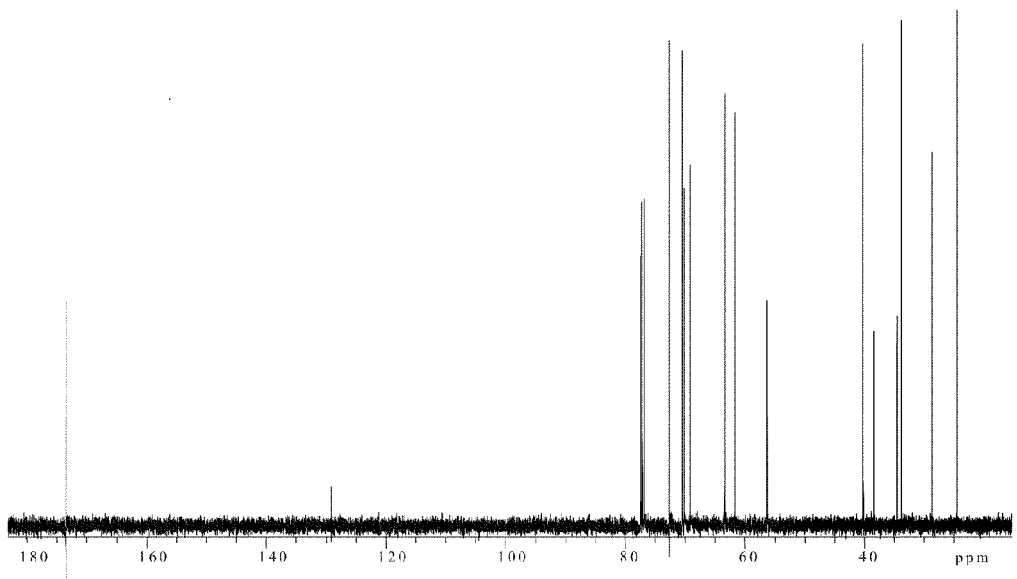
FIG. 2 depicts the $^{13}$C spectrum of the compound ALA-TEG-OH in accordance with an embodiment of the present invention.
Figure 3:
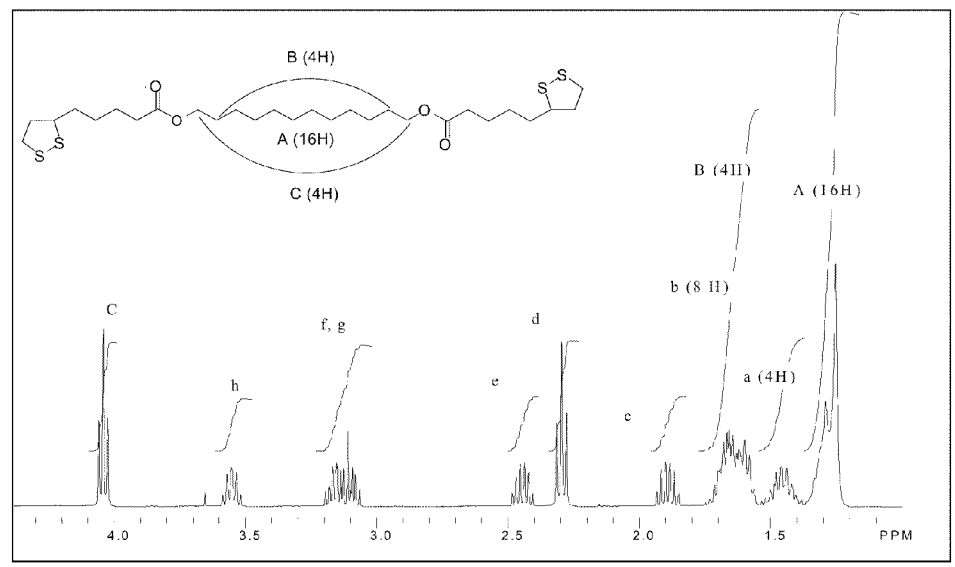
FIG. 3 depicts the $^1$H spectrum of the compound ALA$_2$(1, 12-dodecanediol) in accordance with an embodiment of the present invention.
Figure 4:
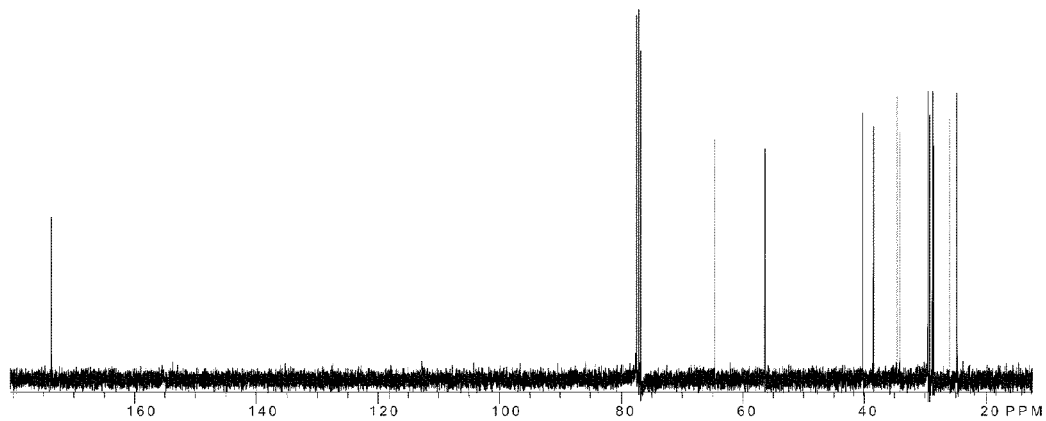
FIG. 4 depicts the $^{13}$C spectrum of the compound ALA$_2$(1, 12-dodecanediol) in accordance with an embodiment of the present invention.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3rd ed., J. Wiley & Sons (New York, N.Y. 2001); and March, *Advanced Organic Chemistry Reactions, Mechanisms and Structure* 5th ed., J. Wiley & Sons (New York, N.Y. 2001) provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The abbreviation "CPT" as used herein refers to camptothecin {(S)-4-ethyl-4-hydroxy-1H-pyrano-[3',4':6,7]indolizino[1,2-b]quinoline-3,14(4H,12H)-dione}, which is shown below. The compound is commercially available from numerous sources; e.g., from Sigma Chemical Co. (St. Louis, Mo.).

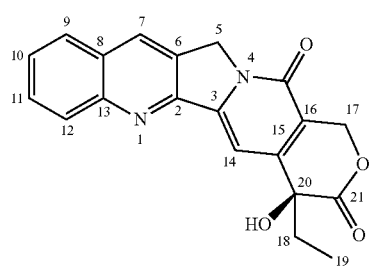

"Camptothecin analogs" as used herein refer to compounds of Formula I:

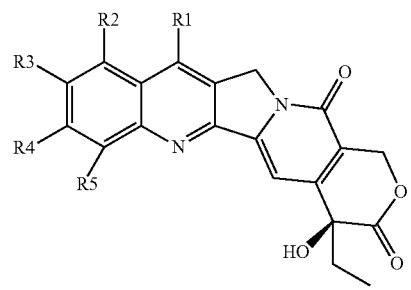

wherein $R_1$, $R_2$, $R_3$, $R_4$, and $R_5$ may each be independently selected from hydrogen or a substituent selected from an alkyl, aryl, cycloaliphatic, and aralkyl group, may be saturated or unsaturated, and may contain hetero atoms (e.g., nitrogen, oxygen, sulfur, halogens, etc).

"Antioxidant derivative of camptothecin" and "antioxidant camptothecin derivative," as used herein refer to a derivative of camptothecin that contains an antioxidant [1,2]-dithiolane ring.

"Antioxidant derivative of a camptothecin analog" and "antioxidant camptothecin analog derivative" as used herein refer to a derivative of a camptothecin analog that contains an antioxidant [1,2]-dithiolane ring.

"Camptothecin nanosphere" and "camptothecin nanosphere prodrug" as used herein refer to a nanosphere comprising an antioxidant derivative of camptothecin or an antioxidant derivative of a camptothecin analog. The nanosphere may further comprise a multiple α-lipoic acid-containing hydrophobic compound, α-tocopherol, a nonsteroidal anti-inflammatory drug (NSAID) derivative, or combinations thereof.

"Cancer" and "cancerous" refer to or describe the physiological condition in mammals that is typically characterized by unregulated cell growth. Examples of cancer include, but are not limited to, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer; including, but not limited to, gliomas, glioblastomas, glioblastoma multiforme (GBM), oligodendrogliomas, primitive neuroectodermal tumors, low, mid and high grade astrocytomas, ependymomas (e.g., myxopapillary ependymoma papillary ependymoma, subependymoma, anaplastic ependymoma), oligodendrogliomas, medulloblastomas, meningiomas, pituitary carcinomas, neuroblastomas, and craniopharyngiomas.

"Mammal" as used herein refers to any member of the class Mammalia, including, without limitation, humans and non-human primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"Nanosphere" as used herein refers to a particle with a size, in at least one dimension, between about 10 nm to about 1000 nm; and may also include a nanoemulsion.

"Nanoprodrug" is used interchangeably with "nanosphere" throughout the application.

"Non-steroidal" as used herein distinguishes the anti-inflammatory drugs from steroids, which have a similar anti-inflammatory action.

"NSAID derivative" as used herein refers to a compound in which as least one NSAID molecule is coupled to a polyol; for example, through esterification.

"Polyol" as used herein refers to a compound that contains at least two free esterifiable hydroxyl groups.

"Therapeutic agent" as used herein refers to any substance used internally or externally as a medicine for the treatment, cure, prevention, slowing down, or lessening of a disease or disorder, even if the treatment, cure, prevention, slowing down, or lessening of the disease or disorder is ultimately unsuccessful.

"Therapeutically effective amount" as used herein refers to an amount which is capable of achieving beneficial results in a patient with a condition or a disease condition in which treatment is sought. A therapeutically effective amount can be determined on an individual basis and will be based, at least in part, on consideration of the physiological characteristics of the mammal, the type of delivery system or therapeutic technique used and the time of administration relative to the progression of the disease.

"Treatment" and "treating," as used herein refer to both therapeutic treatment and prophylactic or preventative measures, wherein the object is to prevent, slow down and/or alleviate the disease or disease condition even if the treatment is ultimately unsuccessful.

The present invention provides for antioxidant derivatives of camptothecin and antioxidant derivatives of camptothecin analogs. These derivatives are useful for treating various types of cancer. In addition, the present invention provides antioxidant-antineoplastic nanospheres comprising the antioxidant derivatives of camptothecin or antioxidant derivatives of camptothecin analogs and methods of preparing the antioxidant-antineoplastic nanospheres. These nanospheres can operate as prodrugs.

In one embodiment, the camptothecin nanosphere prodrugs are capable of releasing camptothecin or a camptothecin analog for a prolonged period of time. In another embodiment, the camptothecin nanosphere prodrugs are capable of serving as a vehicle for the delivery of additional pharmaceuticals.

In one embodiment, an antioxidant derivative of camptothecin and/or an antioxidant derivative of a camptothecin analog may be represented by Formula II:

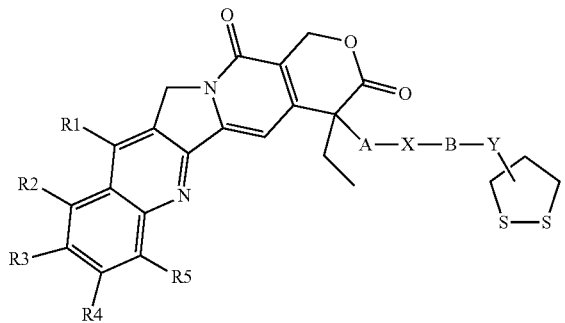

wherein A and B may be independently selected from the group consisting of —OC(O)—, —OC(O)O—, and —OC(O)N(R)—, wherein R may be a hydrogen atom, or a substituted, unsubstituted, branched or unbranched chain of carbon atoms and may contain heteroatoms (e.g., nitrogen, oxygen, sulfur, etc.); wherein X and Y may be each be a linker that may be a substituted, unsubstituted, branched or unbranched chain of carbon atoms and may contain heteroatoms (e.g., nitrogen, oxygen, sulfur, etc.); and wherein $R_1$, $R_2$, $R_3$, $R_4$, and $R_5$ may each be independently selected from hydrogen or a substituent selected from an alkyl, aryl, cycloaliphatic, and aralkyl group, may be saturated or unsaturated, and may contain hetero atoms (e.g., nitrogen, oxygen, sulfur, halogens, etc).

In one embodiment, an antioxidant derivative of camptothecin and/or antioxidant derivative of a camptothecin analog is prepared by the conjugation of a camptothecin or a camptothecin analog and an α-lipoic acid and is represented by Formula III:

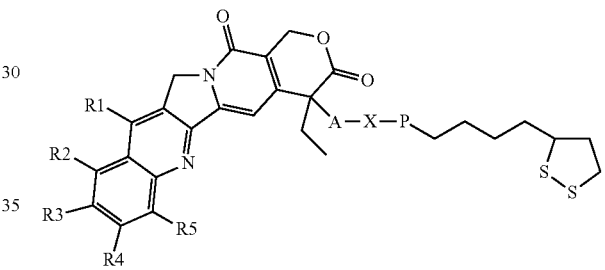

wherein A may be selected from the group consisting of —OC(O)—, —OC(O)O—, and —OC(O)N(R)—, wherein R may be a hydrogen atom, or a substituted, unsubstituted, branched or unbranched chain of carbon atoms and may contain heteroatoms (e.g., nitrogen, oxygen, sulfur, etc.); wherein P may be selected from the group consisting of —OC(O)—, and —N(R)C(O)—, wherein R may be a hydrogen atom, or a substituted, unsubstituted, branched or unbranched chain of carbon atoms and may contain heteroatoms (e.g., nitrogen, oxygen, sulfur, etc.); wherein X may be a linker that may be a substituted, unsubstituted, branched or unbranched chain of carbon atoms and may contain heteroatoms (e.g., nitrogen, oxygen, sulfur, etc.); and wherein $R_1$, $R_2$, $R_3$, $R_4$, and $R_5$ may each be independently selected from hydrogen or a substituent selected from an alkyl, aryl, cycloaliphatic, and aralkyl group, may be saturated or unsaturated, and may contain hetero atoms (e.g., nitrogen, oxygen, sulfur, halogens, etc).

In another embodiment, an antioxidant derivative of camptothecin and/or antioxidant derivative of a camptothecin analog is prepared by the conjugation of camptothecin or a camptothecin analog and α-lipoic acid via a diol and is represented Formula IV:

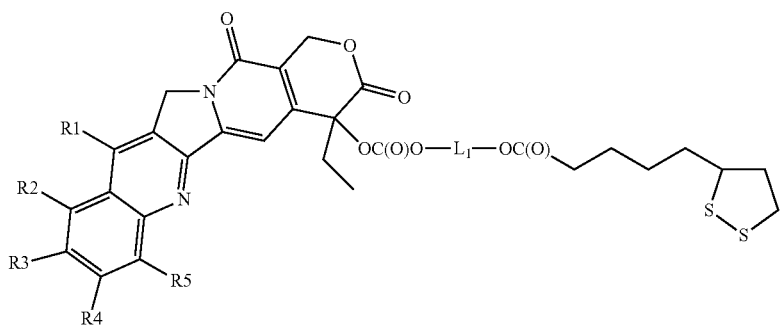

wherein $L_1$ may be a moiety formed by esterification of two free esterifiable hydroxyl groups on a diol; and wherein $R_1$, $R_2$, $R_3$, $R_4$, and $R_5$ may each be independently selected from hydrogen or a substituent selected from an alkyl, aryl, cycloaliphatic, and aralkyl group, may be saturated or unsaturated, and may contain hetero atoms (e.g., nitrogen, oxygen, sulfur, halogens, etc).

In various embodiments, diols that are useful in the present invention may be represented by the following formula:

wherein W may be a hydrocarbon group; for example, an alkyl, aryl, cycloaliphatic or aralkyl group; and may be saturated or unsaturated. W may also contain hetero atoms (e.g., nitrogen, oxygen, sulfur, etc.).

Additional examples of diols that are useful in the present invention include, but are not limited to commercially available one as follows:

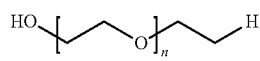

wherein n is an integer between 1 and 100.

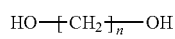

wherein n is an integer between 2 and 12.

1,4-Bis(2-hydroxyethyl)-piperazine

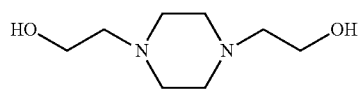 [SMILES: OCCN1CCN(CCO)CC1]

1,3-Cyclopentanediol

1,4-cyclohexanediol

Examples of particularly useful antioxidant derivatives of camptothecin and/or antioxidant derivatives of camptothecin analogs of this embodiment are represented by the following formulas:

Formula V

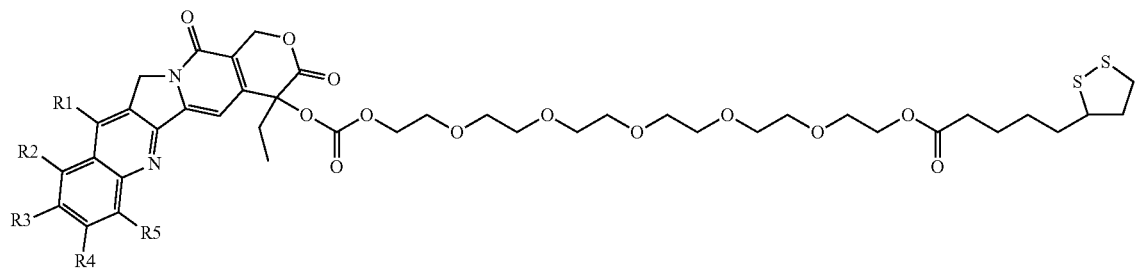

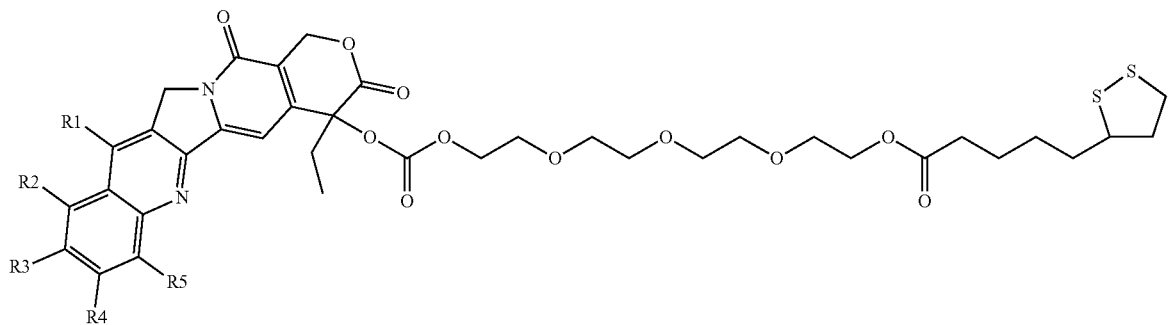
Formula VI
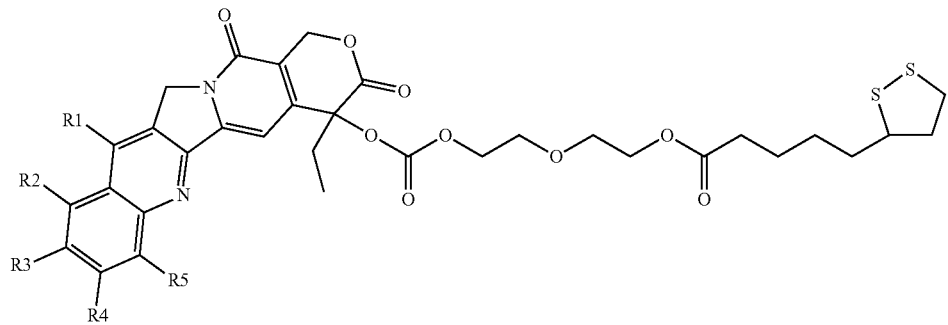
Formula VII
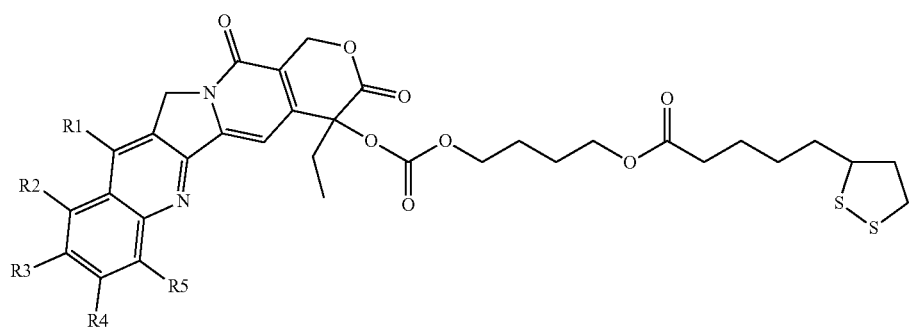
Formula VIII
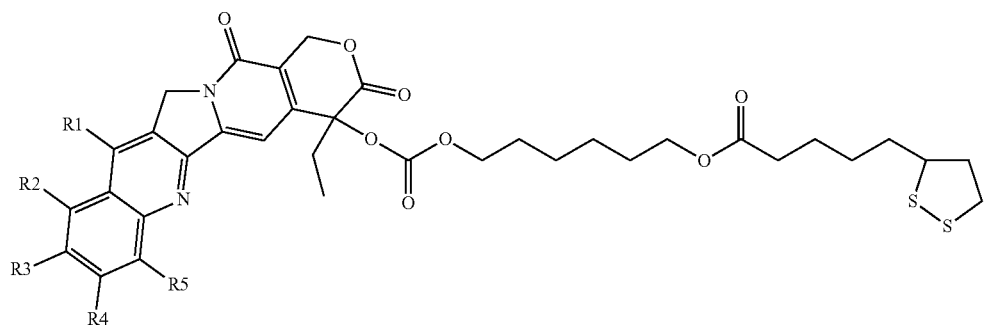
Formula IX -continued
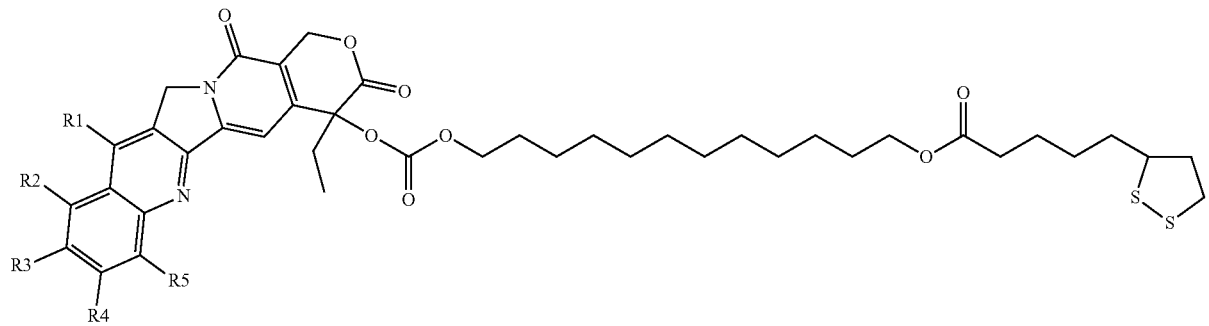
Formula X
wherein $R_1$, $R_2$, $R_3$, $R_4$, and $R_5$ may each be independently selected from hydrogen or a substituent selected from an alkyl, aryl, cycloaliphatic, and aralkyl group, may be saturated or unsaturated, and may contain hetero atoms (e.g., nitrogen, oxygen, sulfur, halogens, etc).
One exemplary compound and its synthesis are shown below.
Formula XLVI
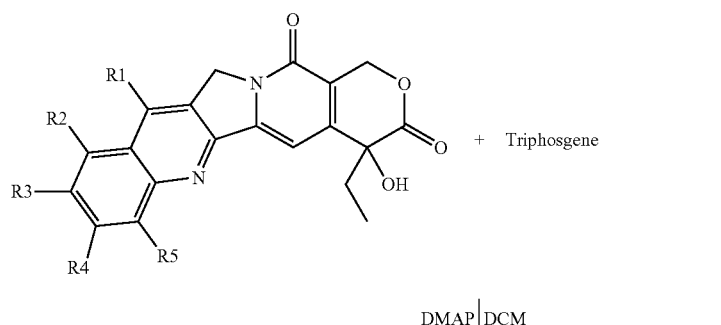
A
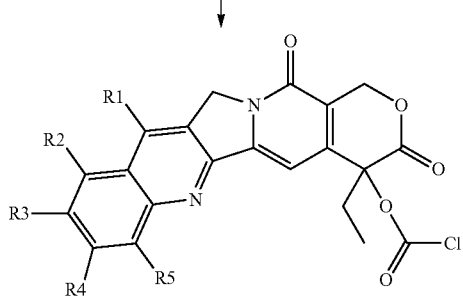
B
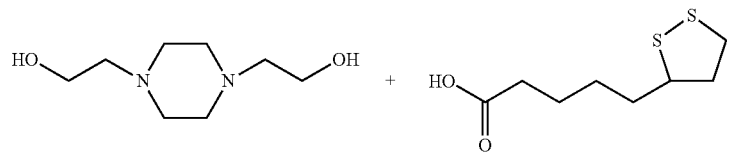
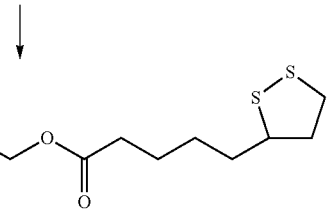

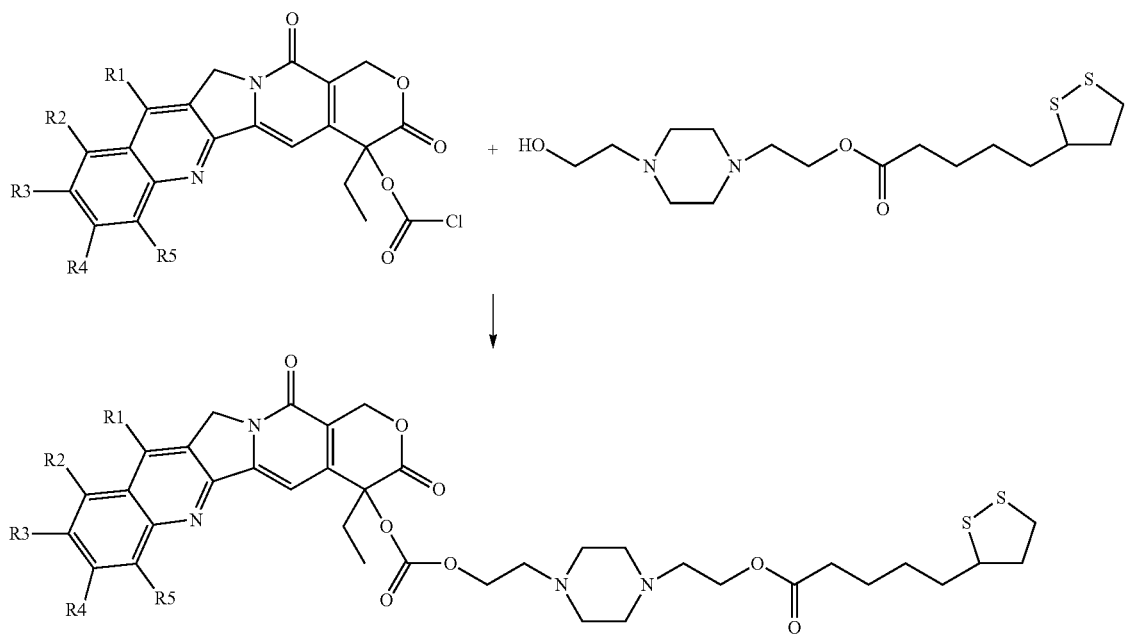

In another embodiment, an antioxidant derivative of a camptothecin and/or antioxidant derivative of a camptothecin analog is prepared by the conjugation of camptothecin or a camptothecin analog and an α-lipoic acid via a diamine and is represented by Formula XI:

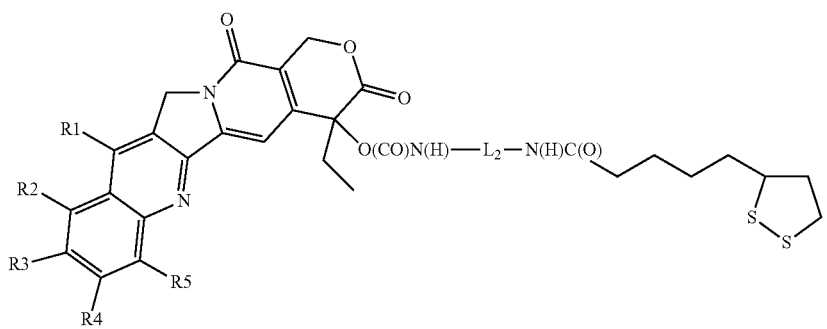

wherein $L_2$ may be a moiety formed by using a diamine as the linker in the process of producing the antioxidant camptothecin derivative or the antioxidant camptothecin analog derivative; and wherein $R_1$, $R_2$, $R_3$, $R_4$, $R_5$ may each be independently selected from hydrogen or a substituent selected from an alkyl, aryl, cycloaliphatic, and aralkyl group, may be saturated or unsaturated, and may contain hetero atoms (e.g., nitrogen, oxygen, sulfur, halogens, etc).

In one embodiment, diamines that are useful in the present invention may be represented by the following formula:

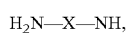

wherein X may be a hydrocarbon group; for example, an alkyl, aryl, cycloaliphatic or aralkyl group; and may be saturated or unsaturated. X may also contain hetero atoms (e.g., nitrogen, oxygen, sulfur, etc.).

In other embodiments, diamines that are useful in the present inventive compounds include, but are not limited to commercially available ones as follows:

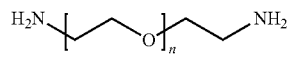

wherein n is an integer between 1 and 100.

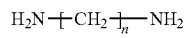

wherein n is an integer between 2 and 12.

Examples of particularly useful antioxidant derivatives of camptothecin and/or antioxidant derivatives of camptothecin analogs of this embodiment are represented by the following formulas:

Formula XII
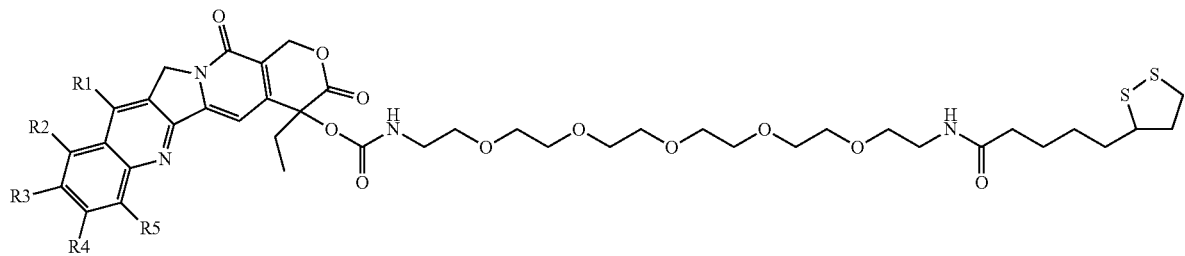
Formula XIII
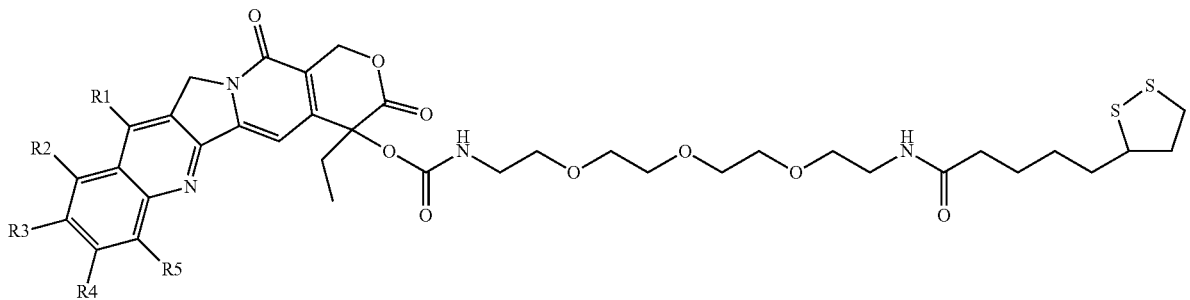
Formula XIV
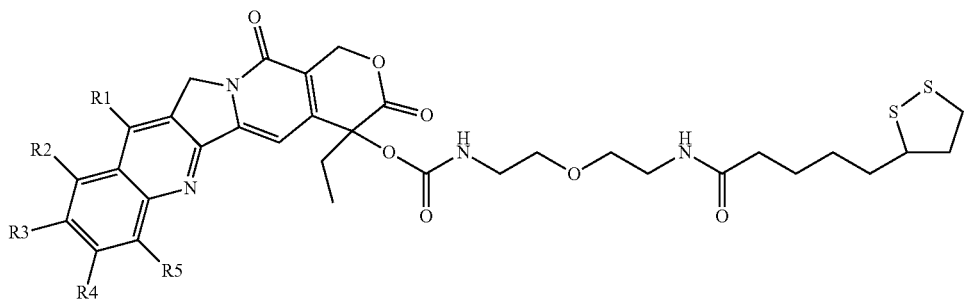
Formula XV
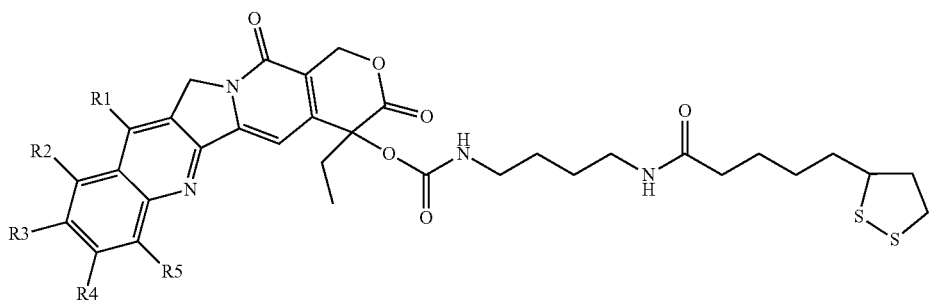
Formula XVI
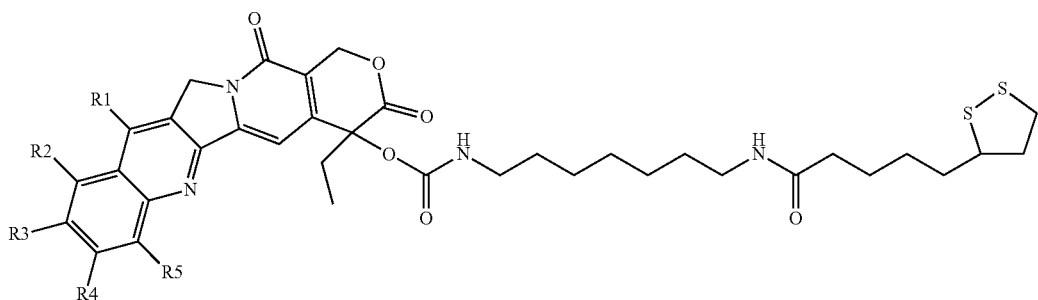

Formula XVII
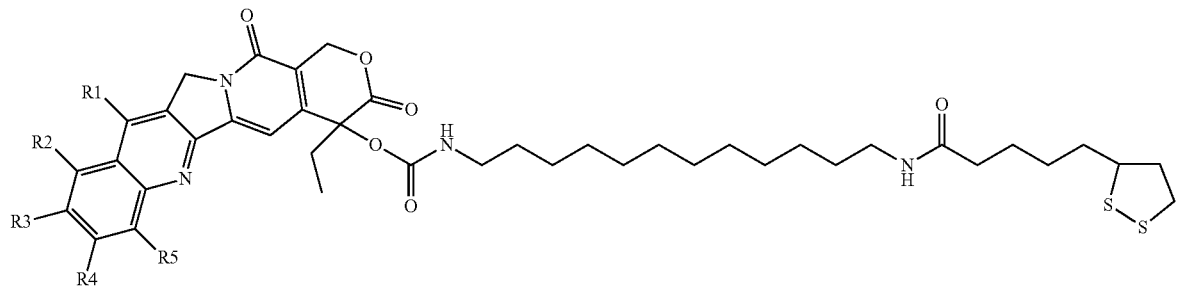
wherein $R_1$, $R_2$, $R_3$, $R_4$, and $R_5$ may each be independently selected from hydrogen or a substituent selected from an alkyl, aryl, cycloaliphatic, and aralkyl group, may be saturated or unsaturated, and may contain hetero atoms (e.g., nitrogen, oxygen, sulfur, halogens, etc).
One exemplary compound and its synthesis are shown below.
Formula XLVII
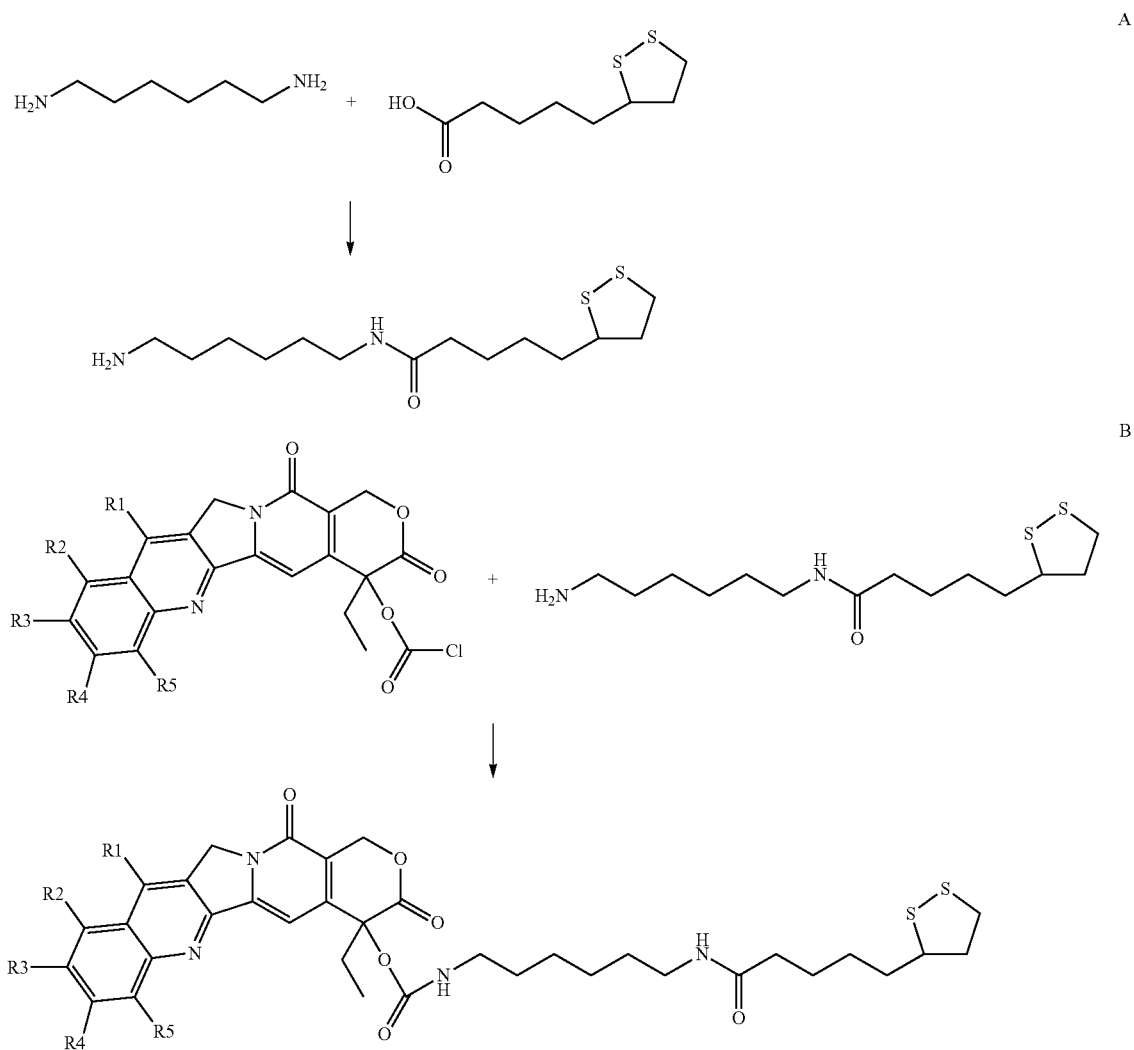

In another embodiment, an antioxidant derivative of camptothecin and/or antioxidant derivative of a camptothecin analog is prepared by the conjugation of camptothecin or a camptothecin analog and an α-lipoic acid via an aminoalcohol and is represented by Formula XVIII:

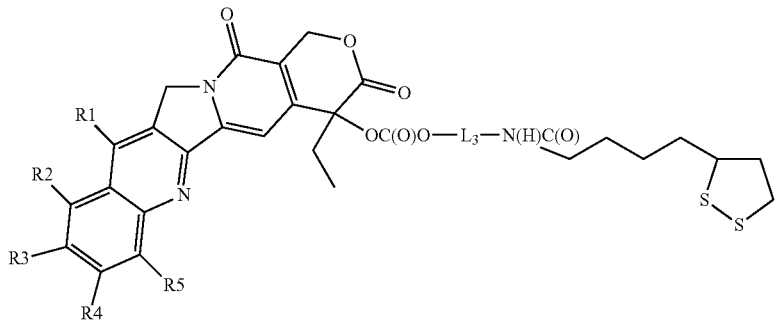

wherein $L_3$ may be a moiety formed by using an aminoalcohol as the linker in the process of producing the antioxidant camptothecin derivative or the antioxidant camptothecin analog derivative; and wherein $R_1$, $R_2$, $R_3$, $R_4$, and $R_5$ may each be independently selected from hydrogen or a substituent selected from an alkyl, aryl, cycloaliphatic, and aralkyl group, may be saturated or unsaturated, and may contain hetero atoms (e.g., nitrogen, oxygen, sulfur, halogens, etc).

Aminoalcohols that are useful in the present invention may be represented by the following formula:

wherein Y may be a hydrocarbon group; for example, an alkyl, aryl, cycloaliphatic or aralkyl group; and may be saturated or unsaturated. Y may also contain hetero atoms (e.g., nitrogen, oxygen, sulfur, etc.).

Examples of aminoalcohols that are useful in the present inventive compounds include, but are not limited to commercially available one as follows:

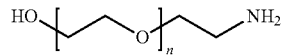

wherein n is an integer between 1 and 100.

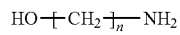

wherein n is an integer between 2 and 12.

Examples of particularly useful antioxidant derivatives of camptothecin and/or antioxidant derivatives of camptothecin analogs of this embodiment are represented by the following formulas:

Formula XIX

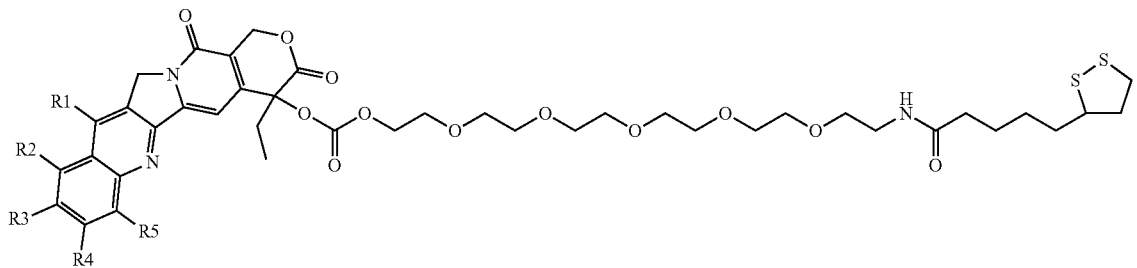

Formula XX

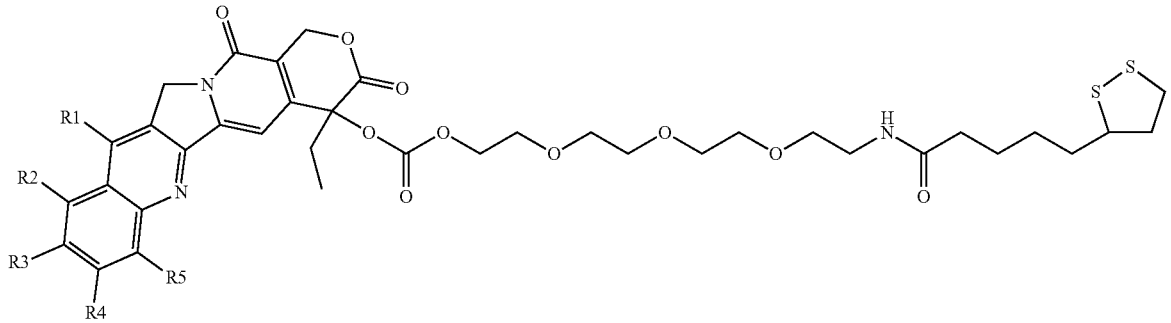

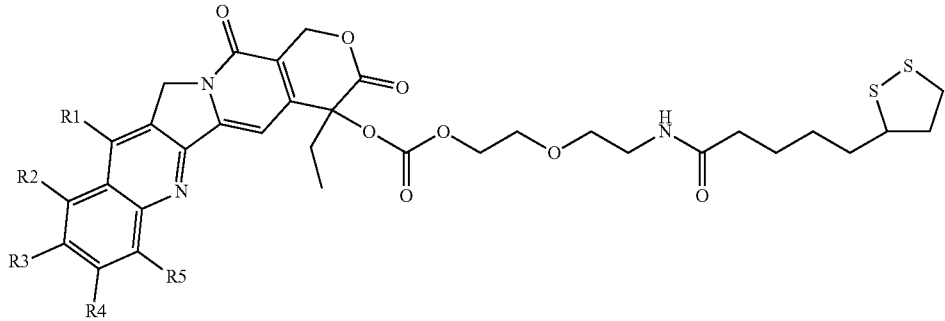
Formula XXI
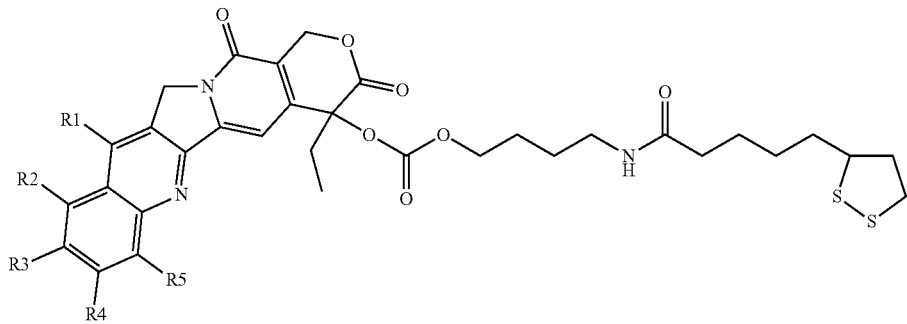
Formula XXII
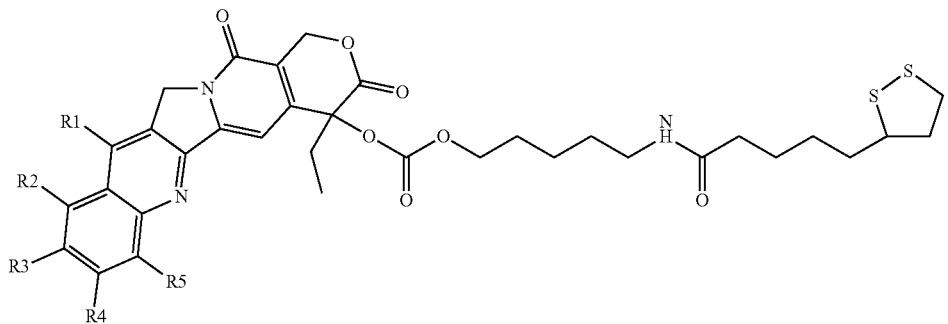
Formula XXIII
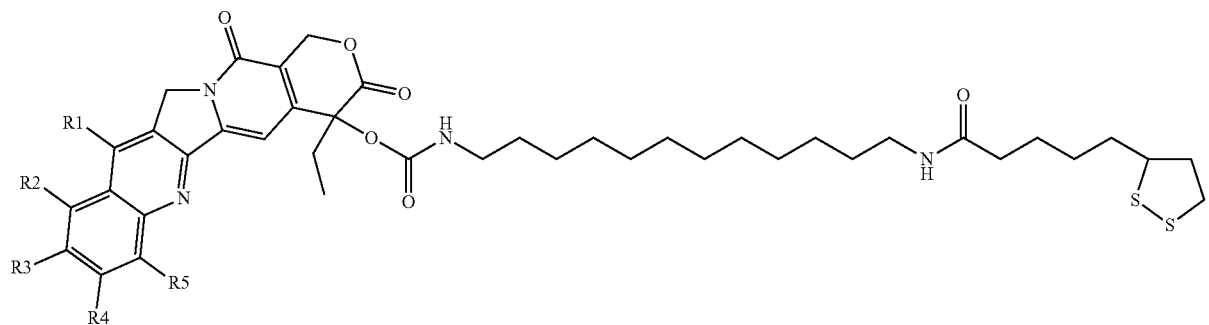
Formula XXIV wherein $R_1$, $R_2$, $R_3$, $R_4$, and $R_5$ may each be independently selected from hydrogen or a substituent selected from an alkyl, aryl, cycloaliphatic, and aralkyl group, may be saturated or unsaturated, and may contain hetero atoms (e.g., nitrogen, oxygen, sulfur, halogens, etc).

One exemplary compound and its synthesis are shown below.

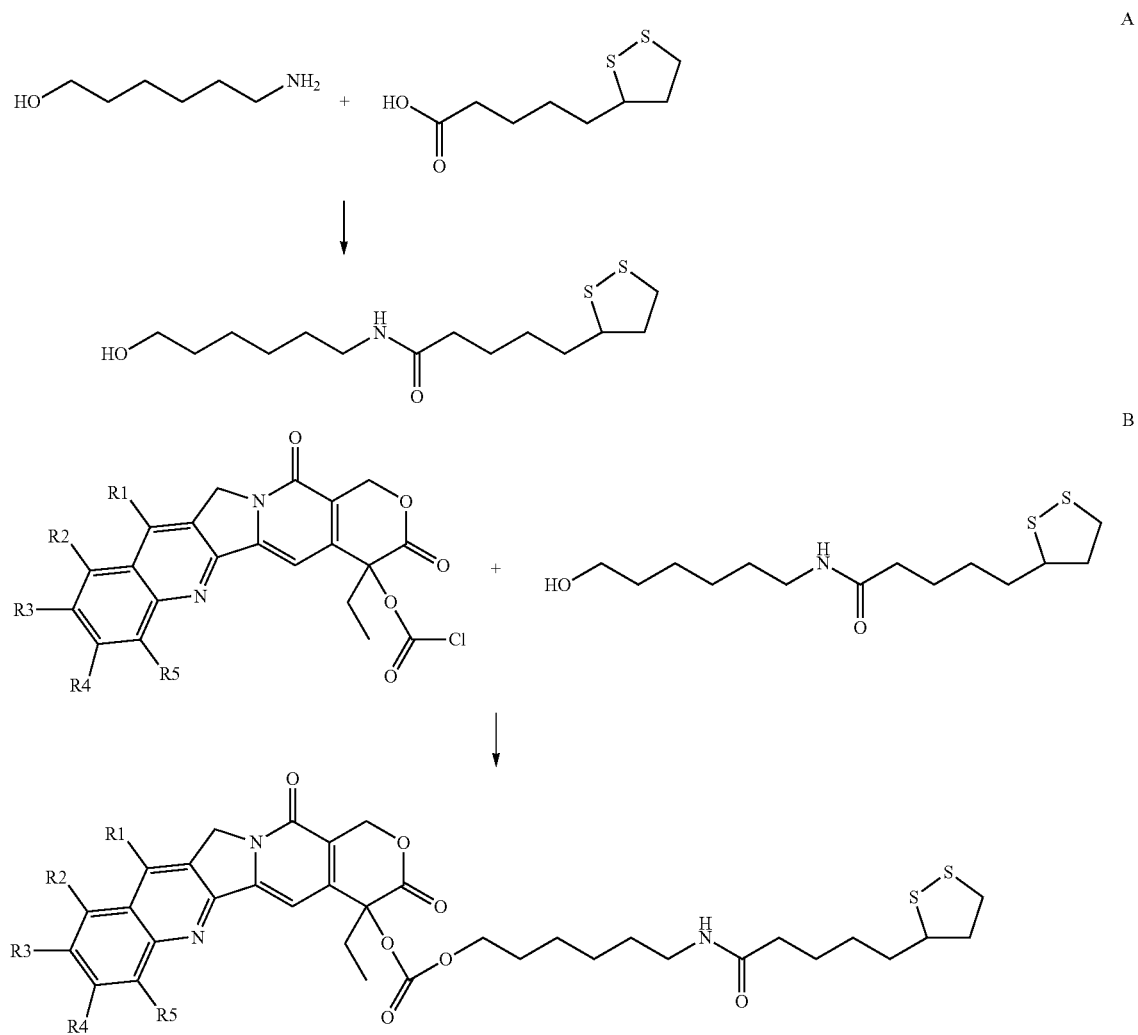

Additional embodiments of the present invention provide for the following compounds:

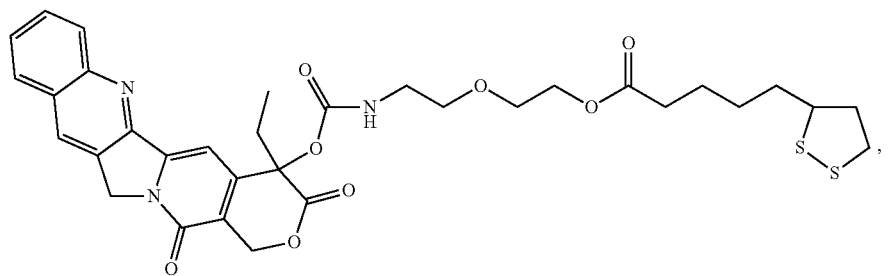

Compound 13

-continued
Compound 14
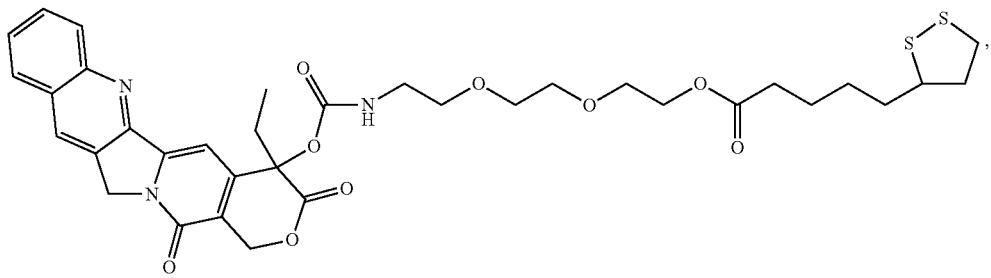
Compound 15
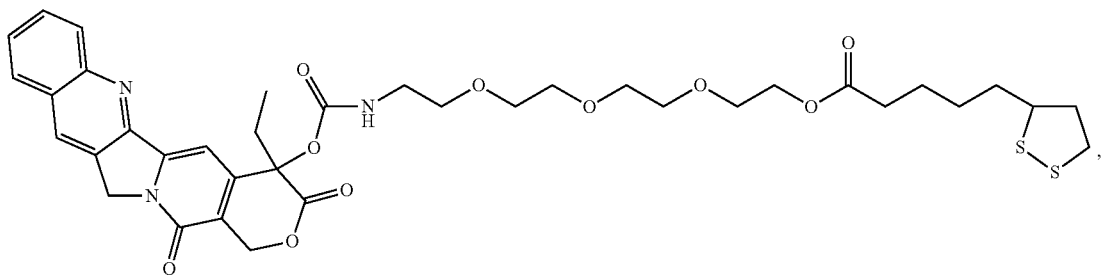
Compound 16
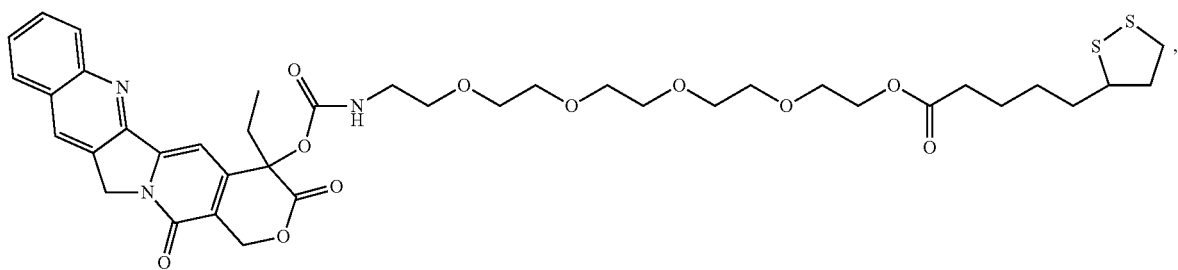
Compound 17
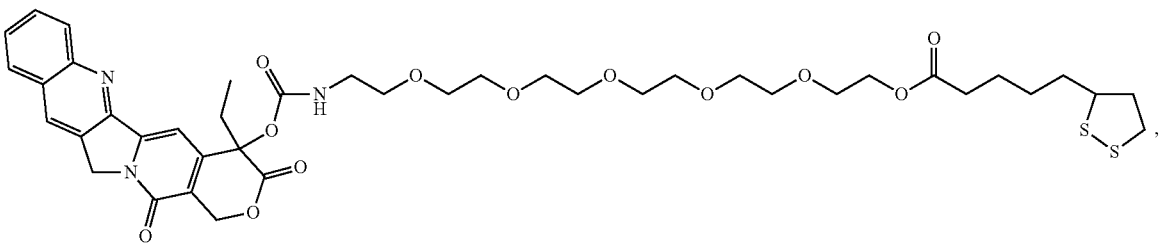
Compound 18
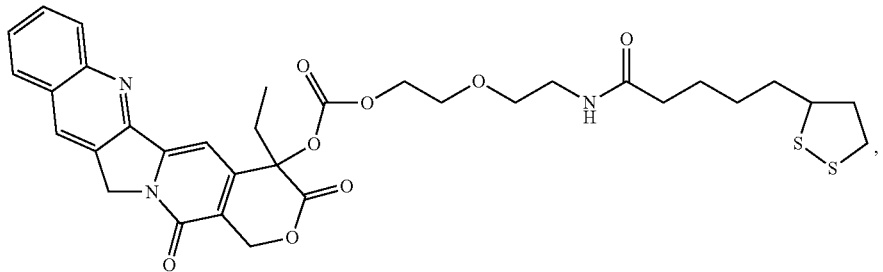

Compound 19

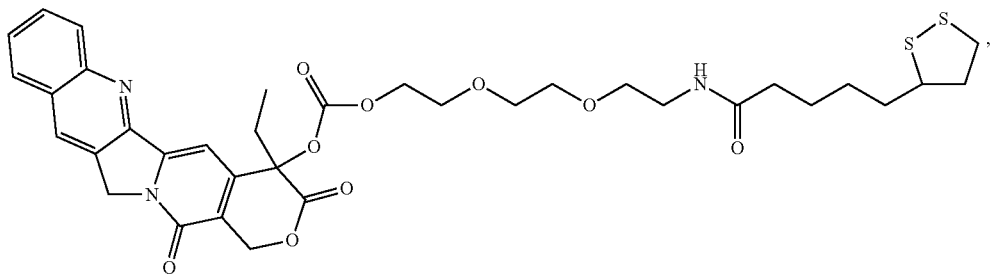

Compound 20

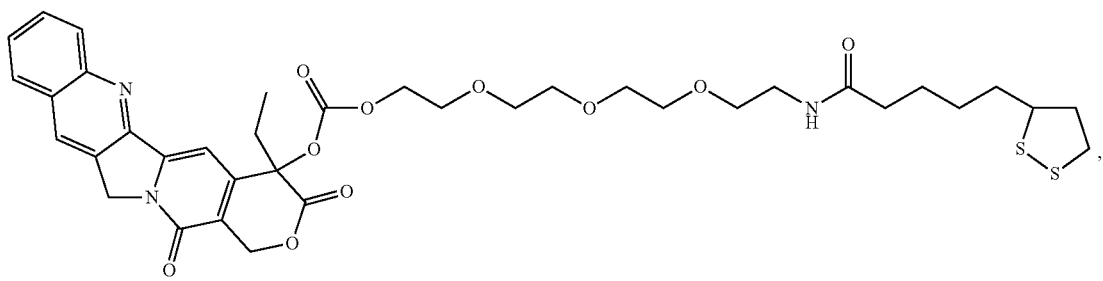

Compound 21

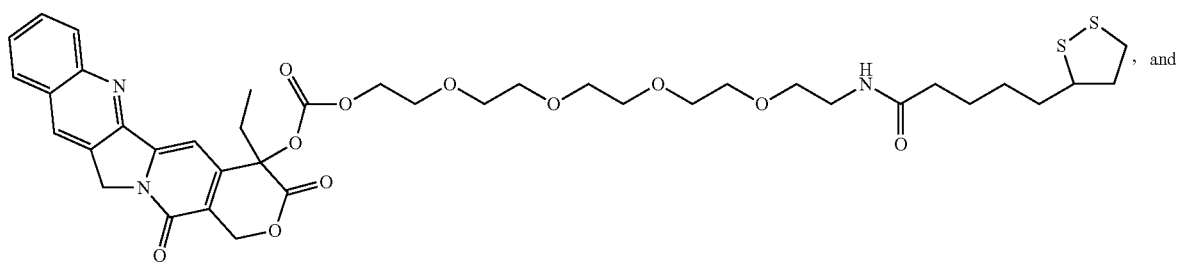

, and

Compound 22

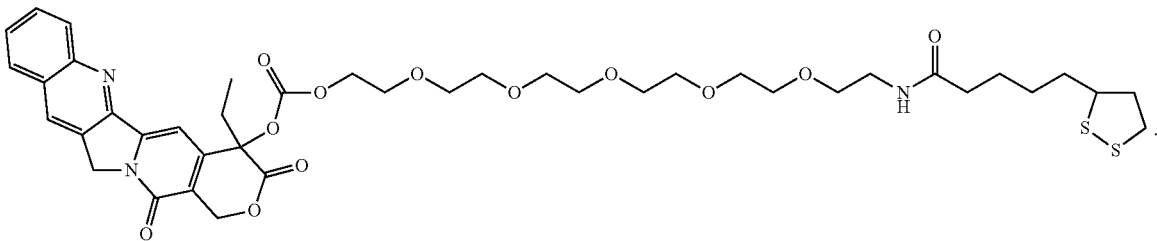

.

In another embodiment, the camptothecin analogs are modified by reaction with succinic anhydride or glutaric anhydride and an antioxidant derivative of camptothecin and/or antioxidant derivative of a camptothecin analog is prepared by the conjugation of an α-lipoic acid and the modified camptothecin or camptothecin analog. One exemplary compound and its synthesis are shown below.

67 68
A
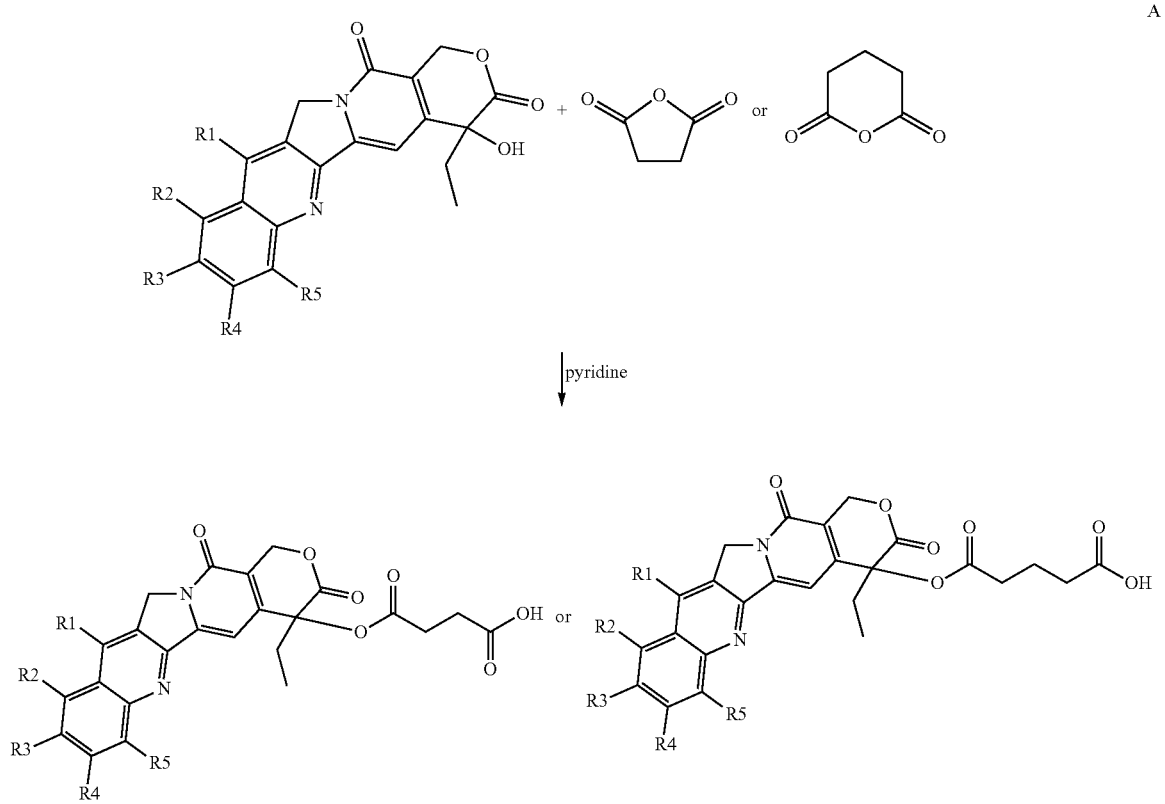
B
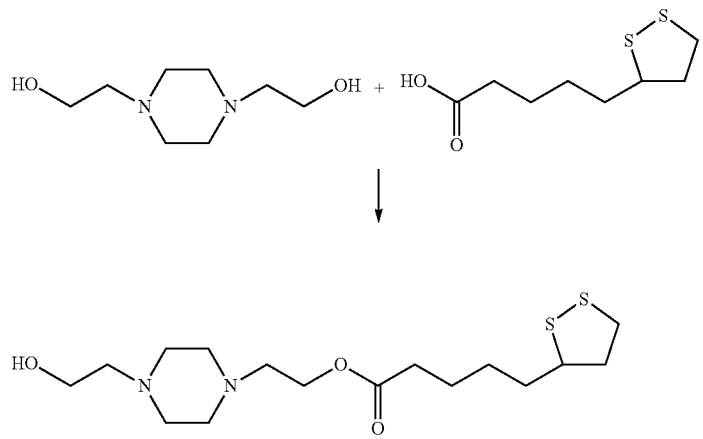
C
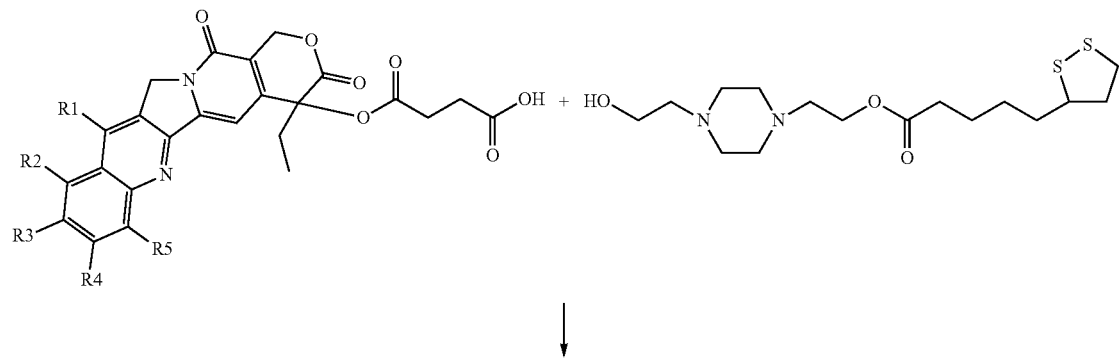

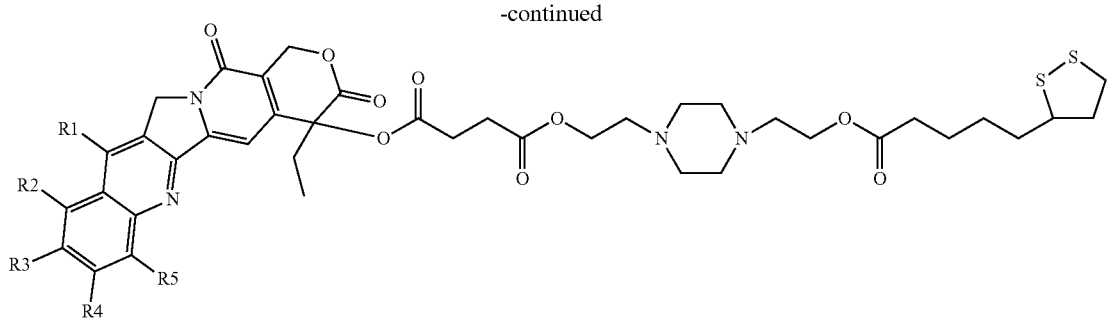

Formula XXV wherein $R_1$, $R_2$, $R_3$, $R_4$, and $R_5$ may each be independently selected from hydrogen or a substituent selected from an alkyl, aryl, cycloaliphatic, and aralkyl group, may be saturated or unsaturated, and may contain hetero atoms (e.g., nitrogen, oxygen, sulfur, halogens, etc).

Additional examples of particularly useful antioxidant derivatives of camptothecin and/or antioxidant derivatives of camptothecin analogs are represented by formulas as follows:

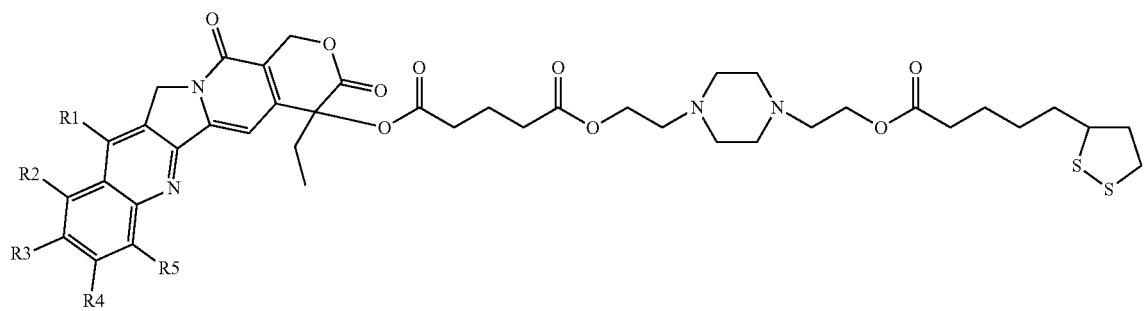

Formula XXVI

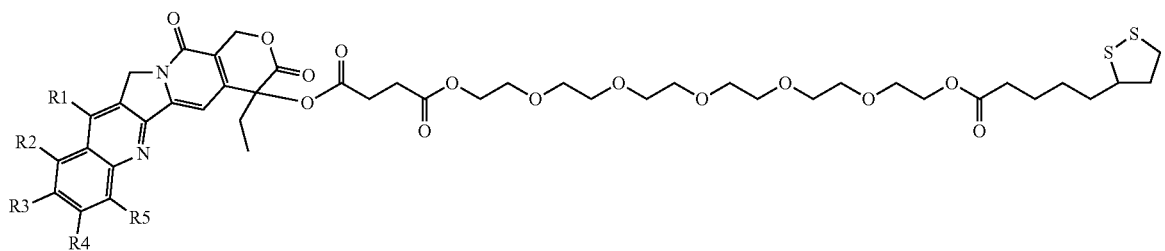

Formula XXVII

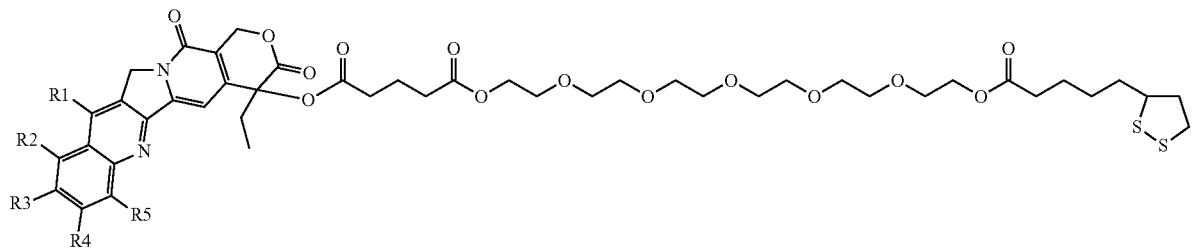

Formula XXVIII

-continued
Formula XXIX
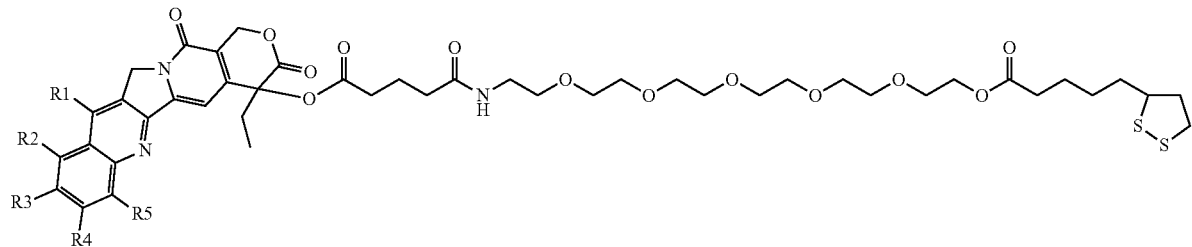
Formula XXX
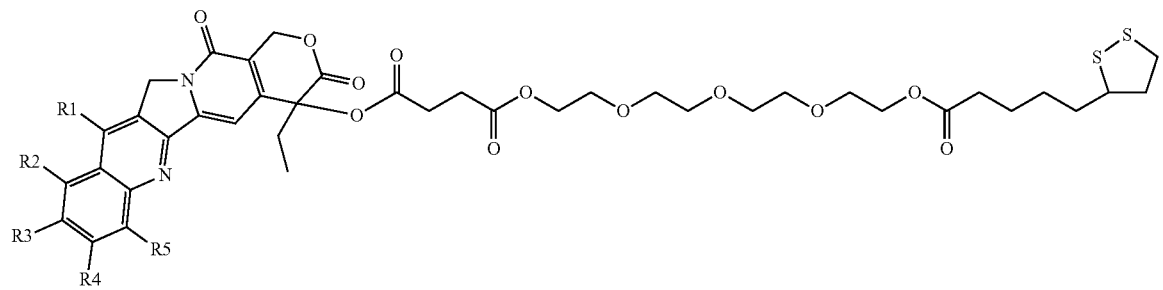
Formula XXXI
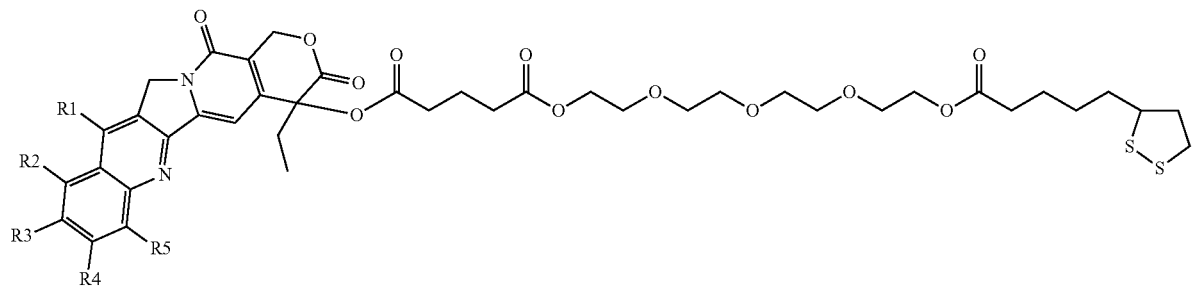
Formula XXXII
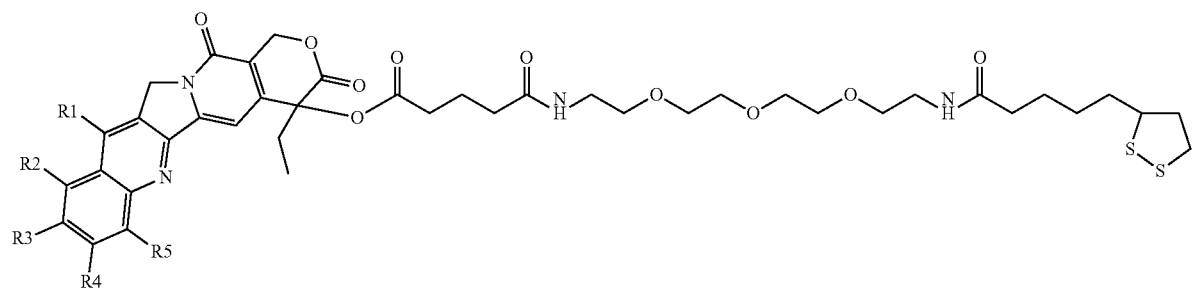
Formula XXXIII
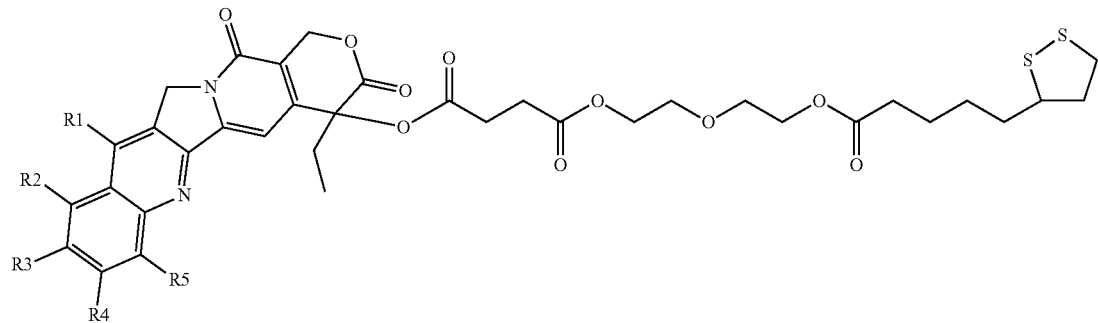

Formula XXXIV
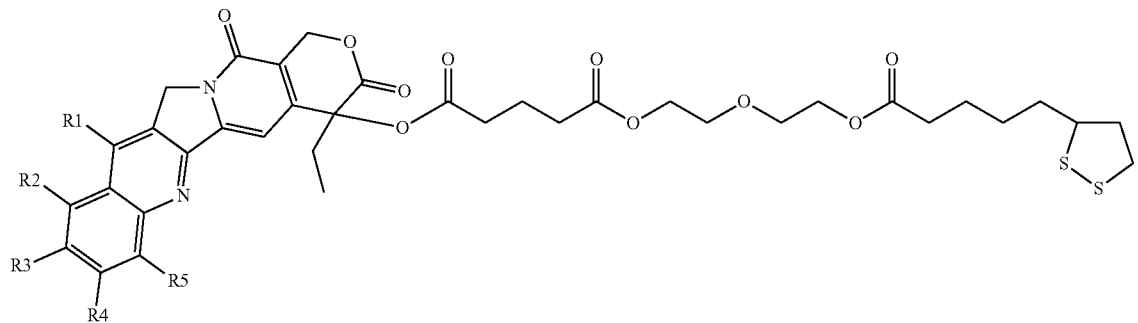
Formula XXXV
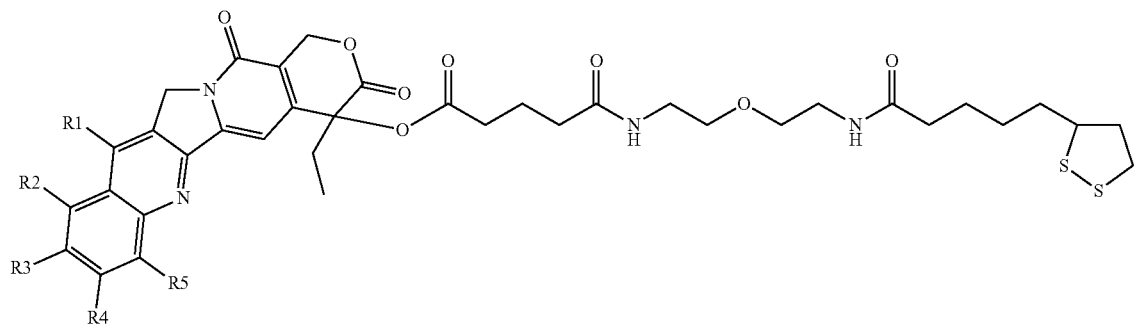
Formula XXVI
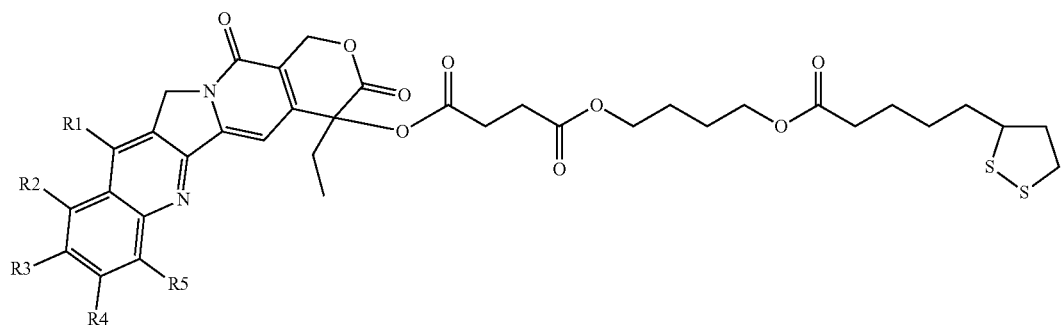
Formula XXXVII
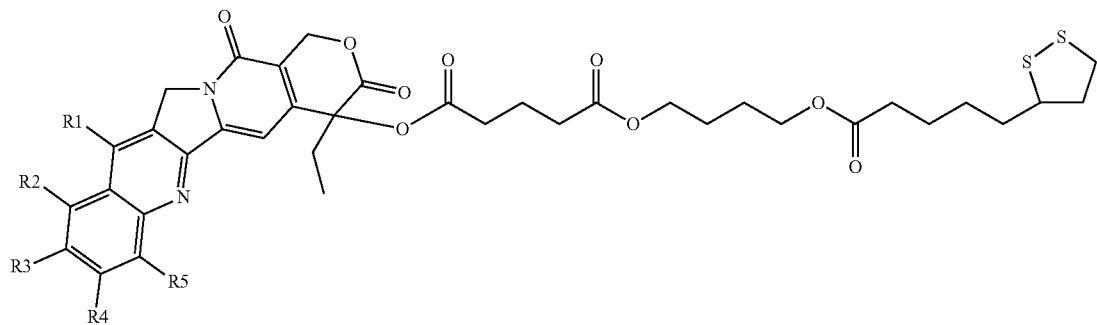

Formula XXXVIII
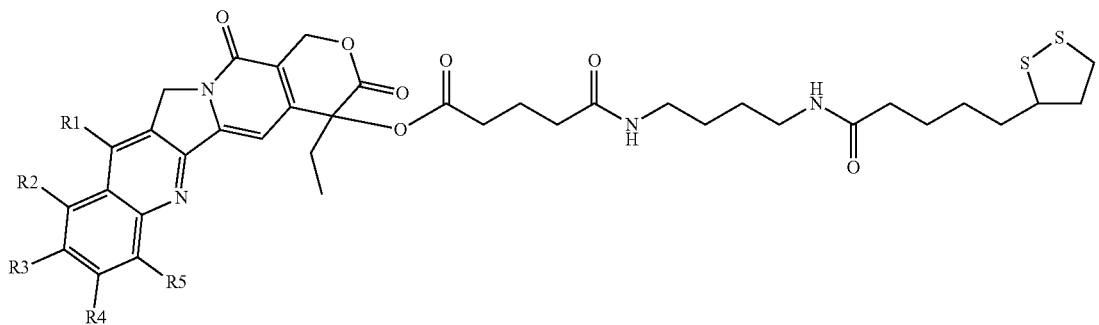
Formula XXXIX
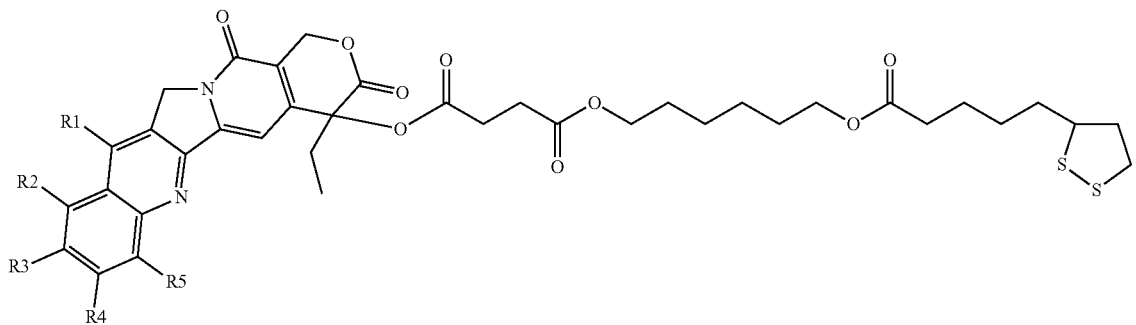
Formula XL
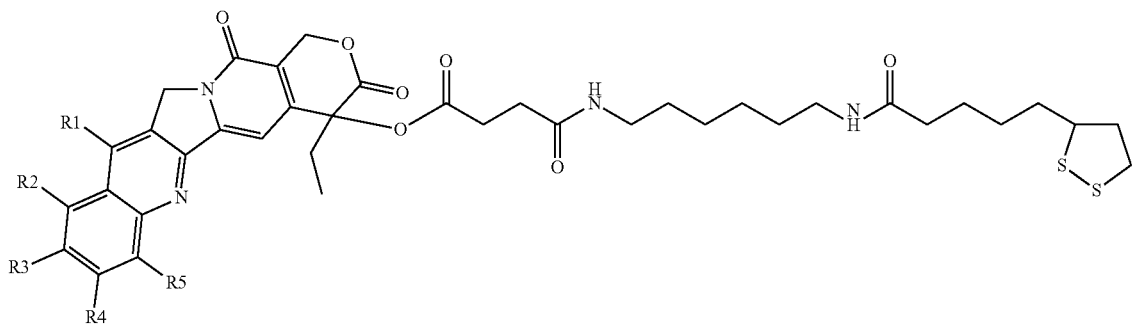
Formula XLI
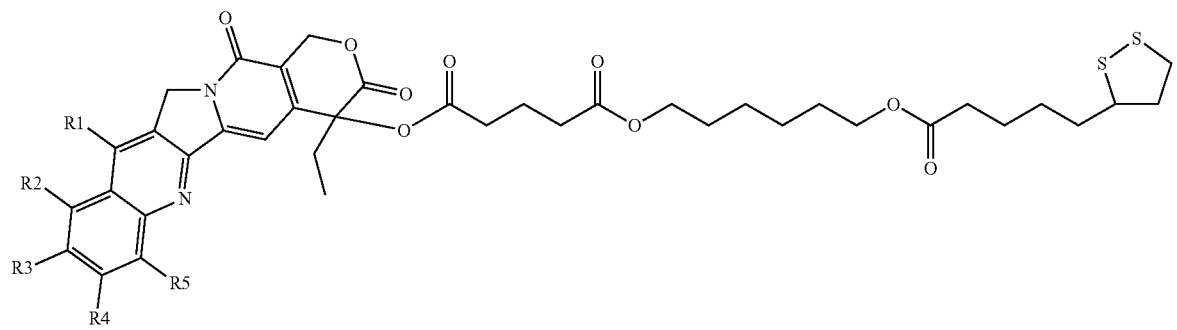

Formula XLII

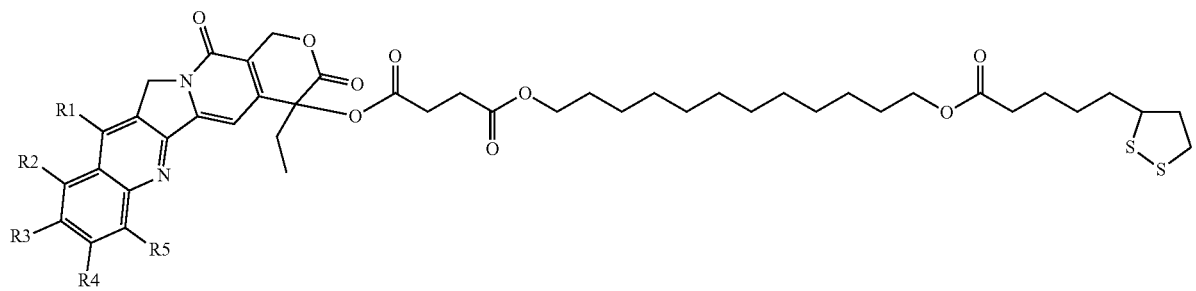

Formula XLIII

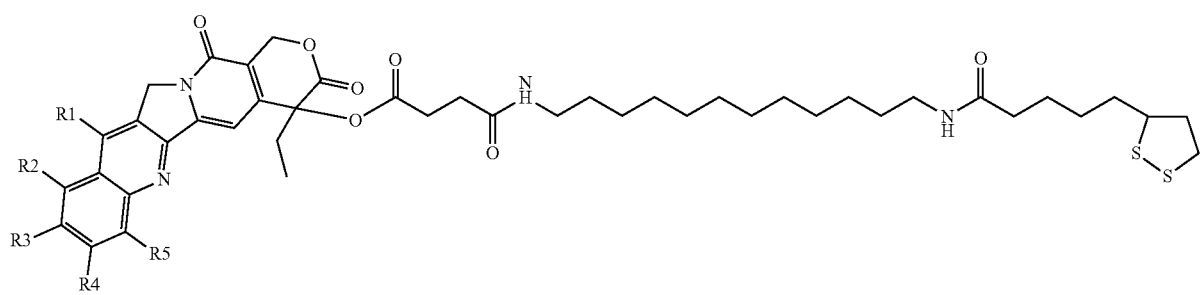

Formula XLIV

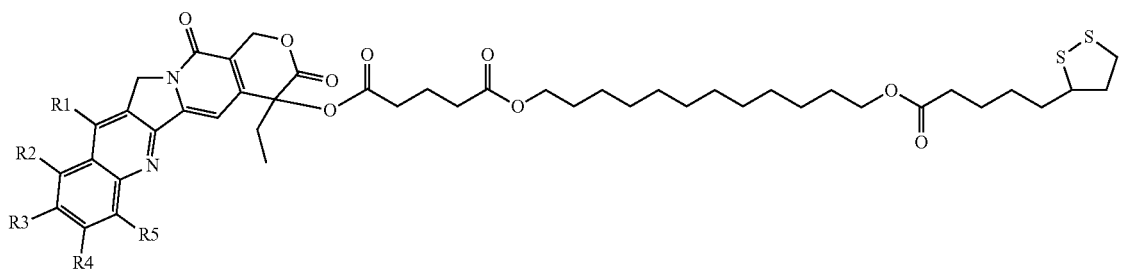

Formula XLV

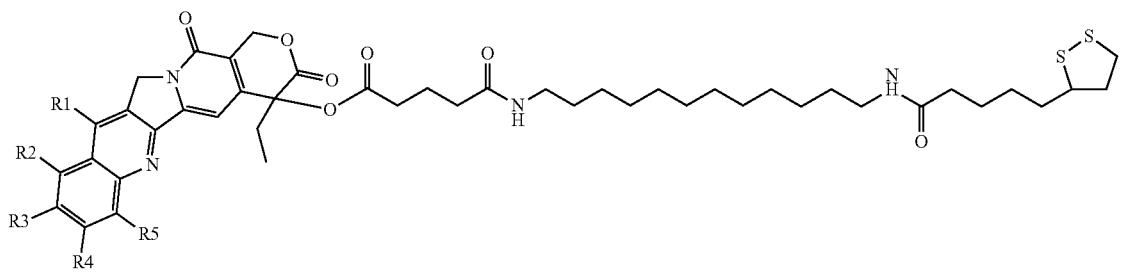

wherein $R_1$, $R_2$, $R_3$, $R_4$, and $R_5$ may each be independently selected from hydrogen or a substituent selected from an alkyl, aryl, cycloaliphatic, and aralkyl group, may be saturated or unsaturated, and may contain hetero atoms (e.g., nitrogen, oxygen, sulfur, halogens, etc).

In one particular embodiment, each of $R_1$ through $R_5$ of the formulas and/or compounds described above is H, and is shown below:

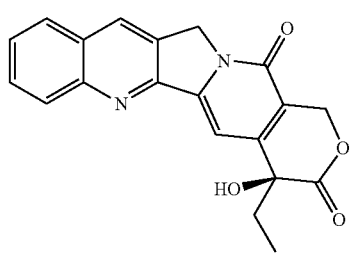 [SMILES: CC[C@@]1(O)C(=O)OCc2c1cc1n(c2=O)Cc2cc3ccccc3nc2-1]

A general scheme for the synthesis of the antioxidant derivatives of camptothecin and antioxidant derivatives of camptothecin analogs and preparation of the antioxidant-antineoplastic nanospheres are described in the ensuing examples. The synthetic procedure is both simple and versatile and leads to the synthesis of the antioxidant derivatives of camptothecin and antioxidant derivatives of camptothecin analogs varying in size and hydrophobicity.

The present invention also provides for methods of treating cancer. In one embodiment, the antioxidant camptothecin derivatives and the antioxidant camptothecin analog derivatives are used for treating cancer. The method comprises providing a pharmaceutical composition comprising an antioxidant camptothecin derivative or an antioxidant camptothecin analog derivative of the present invention, and administering a therapeutically effective amount of the pharmaceutical composition to a subject in need thereof. In a further embodiment, the pharmaceutical composition comprises a pharmaceutically acceptable carrier or excipient.

In one particular embodiment, the antioxidant camptothecin derivatives and the antioxidant camptothecin analog derivatives are used to treat a brain tumor. The method comprises providing a pharmaceutical composition comprising an antioxidant camptothecin derivative or an antioxidant camptothecin analog derivative of the present invention, and administering a therapeutically effective amount of the pharmaceutical composition to a subject in need of treatment for a brain tumor.

Additional embodiments of the present invention provide for methods of preparing the camptothecin nanosphere prodrugs from the antioxidant derivatives of camptothecin and antioxidant derivatives of camptothecin analogs.

In one embodiment, the antioxidant derivatives of camptothecin and antioxidant derivatives of camptothecin analogs are prepared into antioxidant-antineoplastic nanoparticles (e.g., nanospheres) by blending with other antioxidant α-lipoic acid-containing hydrophobic compounds. These compounds are disclosed in U.S. Provisional Application Ser. No. 61/018,749, filed Jan. 3, 2008, and International Application Publication No. WO 2009/086547, filed Dec. 30, 2008, which are incorporated by reference in their entirety as though fully set forth. Examples of these antioxidant α-lipoic acid-containing hydrophobic compounds include, but are not limited to the following:

Antioxidant α-lipoic acid-containing hydrophobic compounds represented by Formula Ia

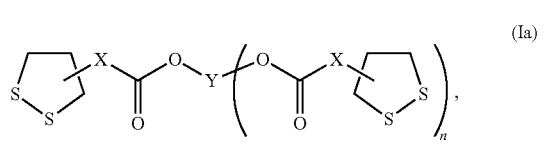

(Ia)

wherein X may be selected from the group consisting of a substituted, unsubstituted, branched or unbranched chain of carbon atoms, and may optionally contain a heteroatom; Y may be selected from the group consisting of a branched and unbranched alkyl, branched and unbranched alkenyl, branched and unbranched alkynyl, heteroatom-containing branched and unbranched alkyl, heteroatom-containing branched and unbranched alkenyl, heteroatom-containing branched and unbranched alkynyl, aryl, cyclic aliphatic, cyclic aromatic, heterocyclic, and aromatic heterocyclic group; and n may be an integer of at least one. In particular embodiments, n may be an integer from 1 to 4; and X may be an unsubstituted, unbranched chain of 1 to 6 carbon atoms.

In one embodiment, the dithiolane moiety in Formula Ia may be an α-lipoic acid and is represented by Formula IIa:

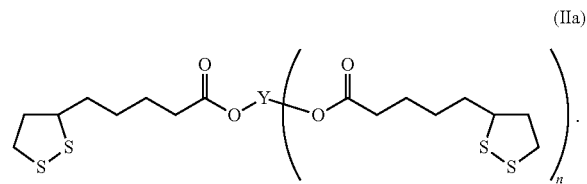

(IIa)

In various embodiments, Y may be a moiety formed by esterification of the hydroxyl groups of a polyol. In various embodiments, the polyol may be selected from the group consisting of

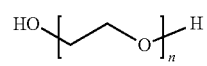

wherein n is an integer between 1 and 4 and

wherein n is an integer between 3 and 16.

One example of a particularly useful multiple α-lipoic acid-containing hydrophobic compound is represented as follows:

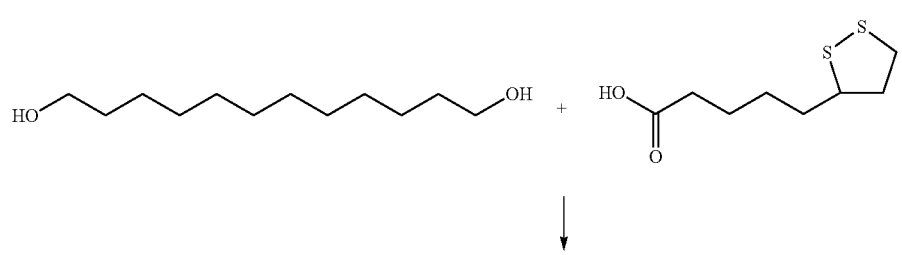

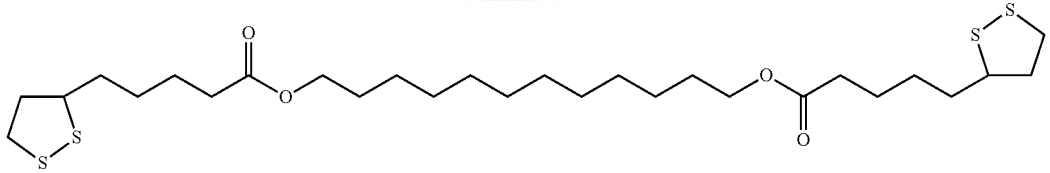

In another embodiment, the antioxidant derivatives of camptothecin and antioxidant derivatives of camptothecin analogs are prepared into nanoparticles (e.g., nanospheres) by blending with a non-steroidal anti-inflammatory drug (NSAID) derivative disclosed in International Application No. PCT/US09/39956, filed on Apr. 8, 2009, which is incorporated by reference in its entirety as though fully set forth. Examples of these NSAID derivatives include, but are not limited to the following:

NSAID derivatives of Formula Ib:

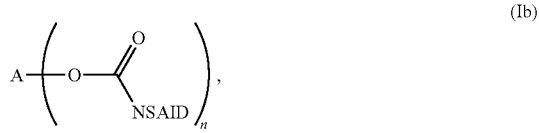
(Ib)

wherein the A may be selected from the group consisting of branched and unbranched alkyl, branched and unbranched alkenyl, branched and unbranched alkynyl, heteroatom-containing branched and unbranched alkyl, heteroatom-containing branched and unbranched alkenyl, heteroatom-containing branched and unbranched alkynyl, aryl, cyclic aliphatic, cyclic aromatic, heterocyclic, and aromatic heterocyclic groups; and n may be an integer of at least two.

In various embodiments, A may be a moiety that is formed by esterification of at least two free esterifiable hydroxyl groups on a polyol. In one embodiment, the polyol may be

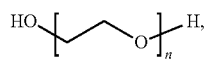

wherein n on the polyol may be an integer between 1 and 6. In another embodiment, the polyol may be

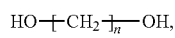

wherein n on the polyol may be an integer between 3 and 16.

In other embodiments, A may be formed from esterification of a polyol selected from group consisting of an ethylene glycol, diethylene glycol, triethylene glycol, tetraethylene glycol, pentaethylene glycol, hexaethylene glycol, 1,3-propanediol, and 1,4-butanediol.

In various embodiments, the NSAID may be selected from the group consisting of aspirin, ibuprofen, flurbiprofen, ketoprofen, fenoprofen, fenbufen, naproxen, indomethacin, diclofenac, ketorolac, tolmetin, flufenamic acid, mefenamic acid, tolfenamic acid, meclofenamic acid, niflumic acid, sulindac, sulindac sulfide and combinations thereof.

NSAID derivatives of Formula IIb

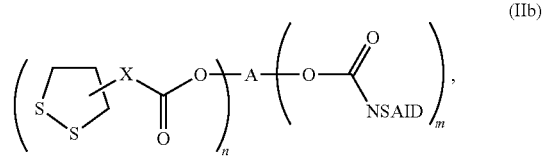
(IIb)

wherein X may be selected from the group consisting of a substituted, unsubstituted, branched or unbranched chain of carbon atoms and may optionally contain a heteroatom; A may be selected from the group consisting of branched and unbranched alkyl, branched and unbranched alkenyl, branched and unbranched alkynyl, heteroatom-containing branched and unbranched alkyl, heteroatom-containing branched and unbranched alkenyl, heteroatom-containing branched and unbranched alkynyl, aryl, cyclic aliphatic, cyclic aromatic, heterocyclic, and aromatic heterocyclic groups; n may be an integer of at least one; and m may be an integer of at least one.

In various embodiments, A may be a moiety that is formed by esterification of at least two free esterifiable hydroxyl groups on a polyol. In particular embodiments, the polyol may be

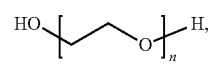

wherein n on the polyol may be an integer between 1 and 6, or

wherein n on the polyol may be an integer between 3 and 16.

In various embodiments, the NSAID may be selected from the group consisting of aspirin, ibuprofen, flurbiprofen, ketoprofen, fenoprofen, fenbufen, naproxen, indomethacin, diclofenac, ketorolac, tolmetin, flufenamic acid, mefenamic acid, tolfenamic acid, meclofenamic acid, niflumic acid, sulindac, sulindac sulfide and combinations thereof.

In one embodiment, the dithiolane moiety may be an α-lipoic acid ("ALA") and is represented by formula IIIb:

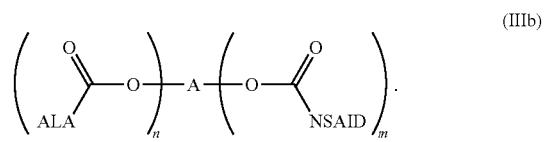
(IIIb)

In another embodiment, the antioxidant derivatives of camptothecin and antioxidant derivatives of camptothecin analogs are prepared into nanoparticles by blending with an antioxidant α-lipoic acid-containing hydrophobic compound and a non-steroidal anti-inflammatory drug (NSAID) derivative disclosed in U.S. Provisional Application Ser. No. 61/018,749, filed Jan. 3, 2008, and International Application Publication No. WO 2009/086547, filed Dec. 30, 2008, and in International Application No. PCT/US09/39956, filed on Apr. 8, 2009, respectively, which are incorporated by reference in their entirety as though fully set forth.

In a further embodiment, α-tocopherol is also added to the mixture for the formation of nanoparticles and camptothecin nanospheres of the present invention. Its addition can provide additional stability to the nanoparticles and nanospheres of the present invention.

The camptothecin nanospheres described above can be used for treating cancer. They can operate as prodrugs as discussed above. The method comprises providing a composition comprising a camptothecin nanosphere of the present invention, and administering a therapeutically effective amount of the composition to a subject in need thereof.

In one particular embodiment, the camptothecin nanospheres are used to treat a brain tumor. The method comprises providing a composition comprising a camptothecin nanosphere, and administering a therapeutically effective amount of the composition to a subject in need of treatment for a brain tumor.

In another embodiment, the camptothecin nanospheres may be used as a carrier of an additional therapeutic agent. In one embodiment, the second therapeutic agent is a chemotherapeutic agent that is useful for cancer treatment. Accordingly, one embodiment provides for a composition comprising a camptothecin nanosphere of the present invention and an additional therapeutic agent.

In one embodiment, the present invention provides for a method to enhance the cytotoxicity of an antineoplastic drug for treatment of a disorder of abnormal cell proliferation. The method comprises providing a composition comprising a camptothecin nanosphere of the present invention; and administering a therapeutically effective amount of the composition and an antineoplastic drug to a subject in need of the treatment to enhance the cytotoxicity of the antineoplastic drug.

In various embodiments, the present invention provides pharmaceutical compositions including a pharmaceutically acceptable excipient along with a therapeutically effective amount of the antioxidant derivatives of camptothecin and/or antioxidant derivatives of camptothecin analogs, or the camptothecin nanosphere prodrugs. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal, parenteral, enteral, or ocular. "Transdermal" administration may be accomplished using a topical cream or ointment or by means of a transdermal patch. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the parenteral route, the compositions may be in the form of solutions or suspensions for infusion or for injection. Via the topical route, the pharmaceutical compositions based on compounds according to the invention may be formulated for treating the skin and mucous membranes and are in the form of ointments, creams, milks, salves, powders, impregnated pads, solutions, gels, sprays, lotions or suspensions. They can also be in the form of microspheres or nanospheres or lipid vesicles or polymer vesicles or polymer patches and hydrogels allowing controlled release. These topical-route compositions can be either in anhydrous form or in aqueous form depending on the clinical indication. Via the ocular route, they may be in the form of eye drops.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins Pa., USA) (2000).

Typical dosages of an effective amount of the antioxidant derivatives of camptothecin and/or antioxidant derivatives of camptothecin analogs, or the camptothecin nanosphere prodrugs can be in the ranges recommended by the manufacturer where known therapeutic compounds are used, and also as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, such as biopsied malignant tumors, or the responses observed in the appropriate animal models, as previously described.

The present invention is also directed to a kit to treat cancer. The kit is an assemblage of materials or components, including at least one of the inventive compositions. Thus, in some embodiments the kit contains a composition including antioxidant derivatives of camptothecin and/or antioxidant derivatives of camptothecin analogs, or the camptothecin nanospheres of the present invention as described above.

The exact nature of the components configured in the inventive kit depends on its intended purpose. For example, some embodiments are configured for the purpose of treating cancer. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to treat cancer. Optionally, the kit also contains other useful components, such as, diluents, buffers, pharmaceutically acceptable carriers, syringes, catheters, applicators, pipetting or measuring tools, or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing antioxidant derivatives of camptothecin and/or antioxidant derivative of camptothecin analogs, or an inventive composition containing antioxidant-antineoplastic nanospheres. The packaging material generally has an external label which indicates the contents and/or purpose of the kit and/or its components.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

General Procedures and Materials

Unless otherwise noted, solvents and chemicals were obtained as highest purity from Sigma-Aldrich Chemical Co. (St Louis, Mo., USA) and used without further preparation. Chromatographic purification of all newly synthesized compounds was performed using silica gel (60 Å, 200-400 mesh). The compounds were analyzed by thin layer chromatography (TLC): silicagel plates (Merck 60 F254); compounds were visualized by irritation by treatment with a solution of 1.5 g of $KMnO_4$, 10 g $K_2CO_3$, and 1.25 mL 10% NaOH in 200 mL of $H_2O$, followed by gentle heating.

HPLC analysis was performed on Merck-Hitachi analytical LaChrom D-7000 HPLC/UV detector system with CAPCELL PAK, Type SG 120 (phenomenex) $C_{18}$ reversed phase column (250/4.6 mm, 5 µm). The composition of the mobile phase (acetonitrile/water mixture containing 0.1% (v/v) trifluoroacetic acid) was adjusted for camptothecin and α-lipoic acid derivatives, multiple α-lipoic acid-containing compounds and NSAID derivatives in order to provide an appropriate retention time and separation.

Example 2

Synthesis of the Camptothecin and α-Lipoic Acid Derivatives A

α-Lipoic acid (ALA, 2.06 g, 10 mmol.) and a diol compound (tetraethylene glycol, TEG) (30 mmol) in 50 mL of anhydrous dichloromethane (DCM) were reacted with 4-(dimethylamino)-pyridine (DMAP, 15 mmol) in the presence of a molecular sieve (60 Å, 10-20 mesh beads) for 10 min at room temperature. N-(3-Dimethylaminopropyl)-N-ethylcarbodiimide hydrochloride (EDCI, 2.3 g, 12 mmol) was added portionwise over 10 min and the reaction mixture was stirred for 5 h at room temperature in the dark, filtered, and then concentrated under vacuum to reduce the volume. The resulting reaction mixture was purified using silica gel by direct loading onto the column without further preparation. The solvent was removed under reduced pressure to give the products.

A suspension of camptothecin (0.4 mmol), triphosgene (0.15 mmol), and DMAP (1.3 mmol) in anhydrous DCM was stirred for 10 min. The mono-ALA-TEG (0.4 mmol) was added and the reaction mixture was stirred for 24 h. The reaction mixture was concentrated under vacuum to reduce the volume. The resulting reaction mixture was purified using silica gel by direct loading onto the column without further preparation. The solvent was removed under reduced pressure to give the products. The same procedure was used for the synthesis of the compounds 1-3 (See Scheme 1).
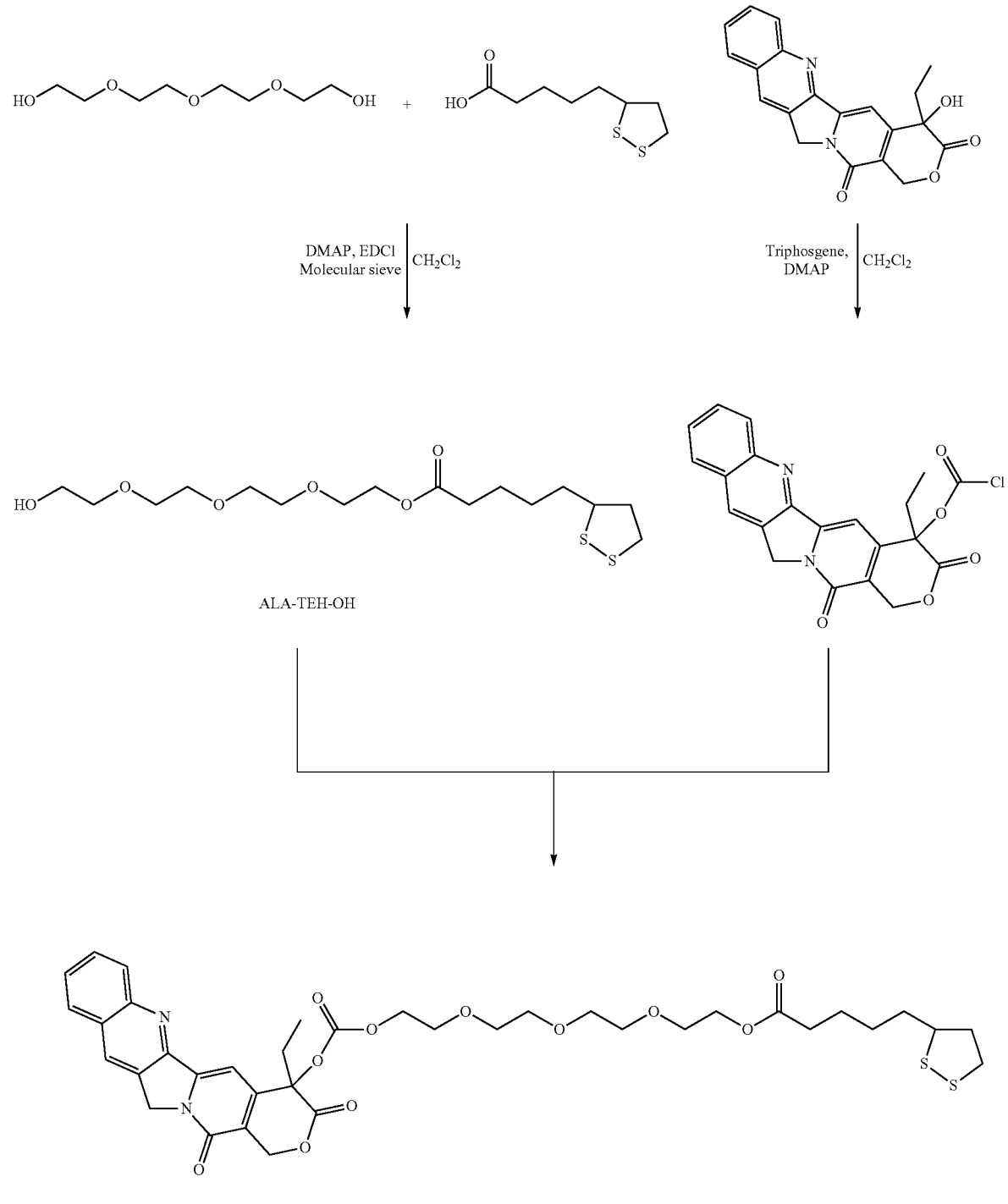
Compound 10

Compound 23:

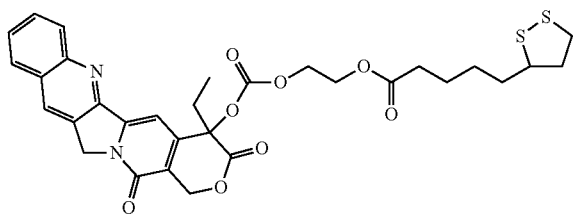 [SMILES: CCC1(OC(=O)OCCOC(=O)CCCCC2CCSS2)C(=O)OCc2c1cc1n(c2=O)Cc2cc3ccccc3nc2-1]

Compound 1, (Camptothecin)-diethylene glycol-(α-lipoic acid):

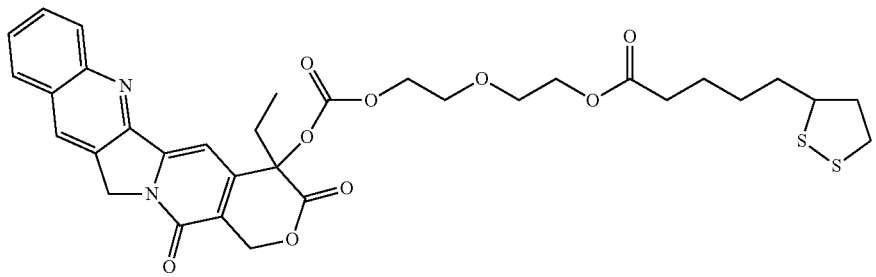 [SMILES: CCC1(OC(=O)OCCOCCOC(=O)CCCCC2CCSS2)C(=O)OCc2c1cc1n(c2=O)Cc2cc3ccccc3nc2-1]

Compound 2, (Camptothecin)-triethylene glycol-(α-lipoic acid):

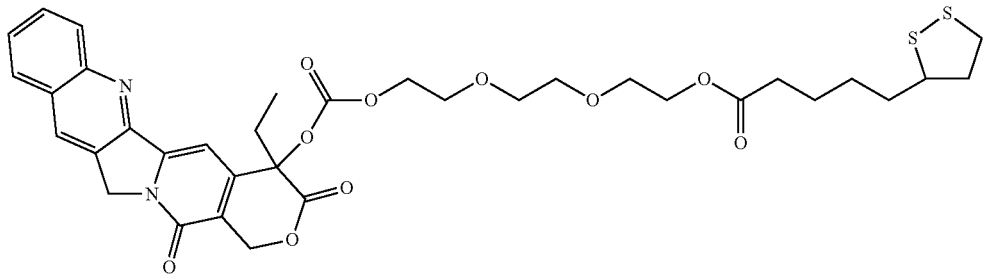 [SMILES: CCC1(OC(=O)OCCOCCOCCOC(=O)CCCCC2CCSS2)C(=O)OCc2c1cc1n(c2=O)Cc2cc3ccccc3nc2-1]

Compound 3, (Camptothecin)-hexaethylene glycol-(α-lipoic acid):

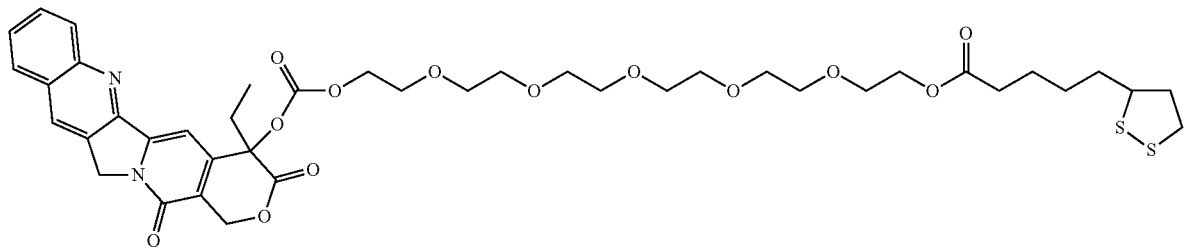 [SMILES: CCC1(OC(=O)OCCOCCOCCOCCOCCOCCOC(=O)CCCCC2CCSS2)C(=O)OCc2c1cc1n(c2=O)Cc2cc3ccccc3nc2-1]

Example 3

Synthesis of the Camptothecin and α-Lipoic Acid Derivatives B

Mono-ALA-TEG was prepared as described in Example 1. Mono-ALA-TEG (10 mmol) and succinic anhydride (100 mmol) were dissolved in 100 mL of pyridine and the reaction mixture was stirred for 3 h at room temperature. The reaction mixture was concentrated under vacuum to reduce the volume. The resulting reaction mixture was purified using silica gel by direct loading onto the column without further preparation. The solvent was removed under reduced pressure to give the products.

Mono-ALA-TEG-SA (5 mmol) and camptothecin (5 mmol) in 10 mL of anhydrous dichloromethane (DCM) were reacted with 4-(dimethylamino)-pyridine (DMAP, 10 mmol) in the presence of molecular sieve (60 Å, 10-20 mesh beads) for 10 min at room temperature. N-(3-Dimethylaminopropyl)-N-ethylcarbodiimide hydrochloride (EDCI, 10 mmol) was added portionwise over 10 min and the reaction mixture was stirred for 5 h at room temperature in the dark, filtered, and then concentrated under vacuum to reduce the volume. The resulting reaction mixture was purified using silica gel by direct loading onto the column without further preparation. The solvent was removed under reduced pressure to give the products. The same procedure was used for the synthesis of the compounds 4-6 (See Scheme 2).

Scheme 2 Synthesis of the camptothecin and α-lipoic acid derivatives B
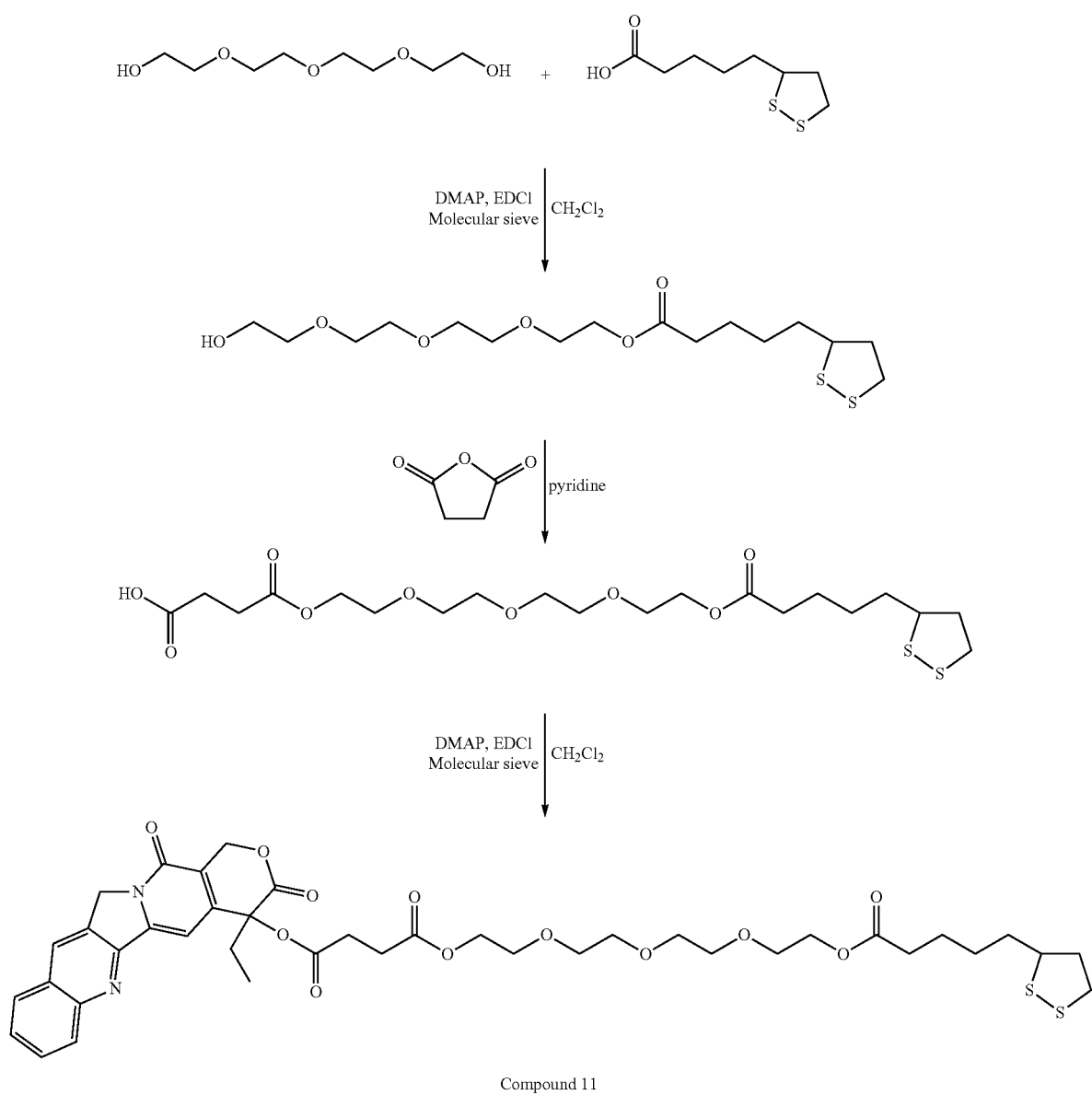
Compound 4, (Camptothecin)-diethylene glycol-(α-lipoic acid):
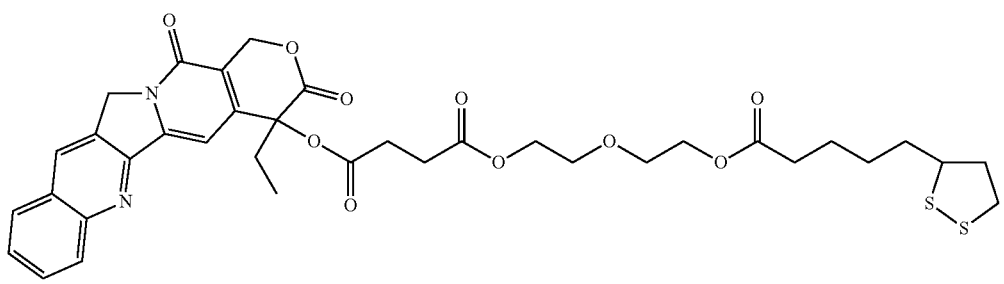 [SMILES: CCC1(OC(=O)CCC(=O)OCCOCCOC(=O)CCCCC2CCSS2)C(=O)OCc2c1cc1n(c2=O)Cc2cc3ccccc3nc2-1]

Compound 5, (Camptothecin)-triethylene glycol-(α-lipoic acid):
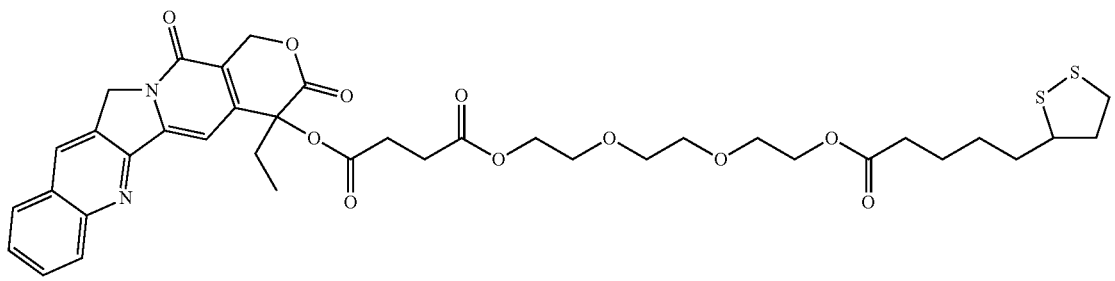 [SMILES: CCC1(OC(=O)CCC(=O)OCCOCCOCCOC(=O)CCCCC2CCSS2)C(=O)OCc2c1cc1n(c2=O)Cc2cc3ccccc3nc2-1]
Compound 6, (Camptothecin)-hexaethylene glycol-(α-lipoic acid):
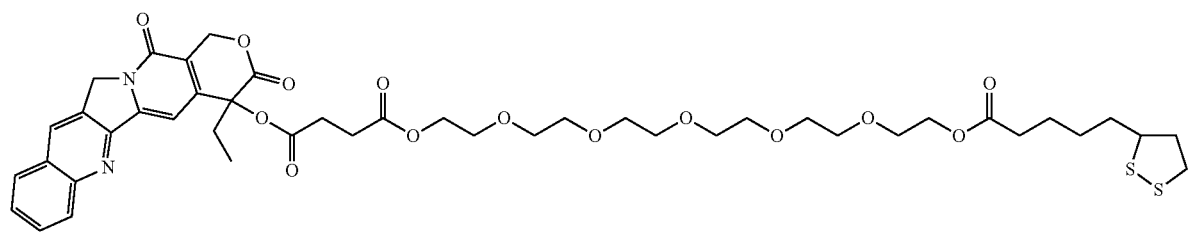 [SMILES: CCC1(OC(=O)CCC(=O)OCCOCCOCCOCCOCCOCCOC(=O)CCCCC2CCSS2)C(=O)OCc2c1cc1n(c2=O)Cc2cc3ccccc3nc2-1]
Scheme 3
Synthesis of the Camptothecin and α-Lipoic Acid Derivatives C
The derivatives C were prepared as described in Example 2.
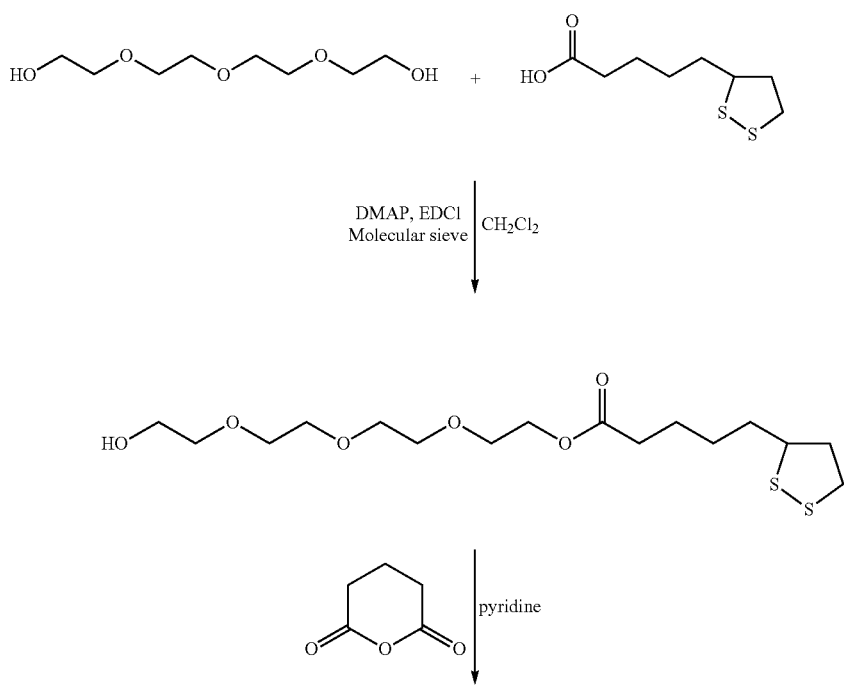

-continued
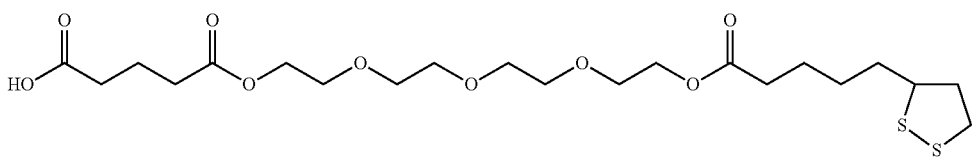
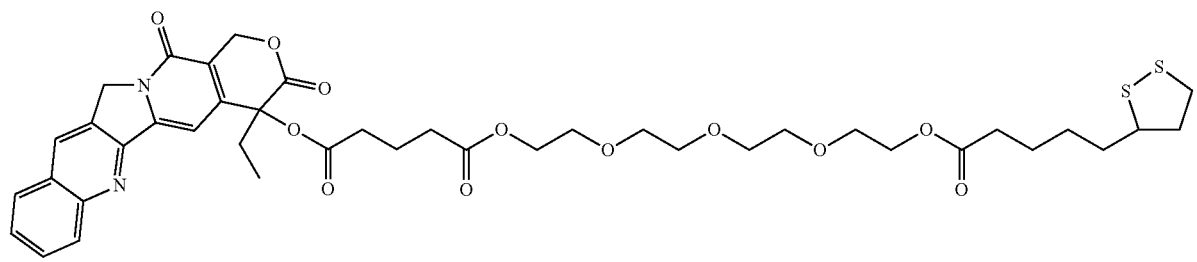
Compound 12
Compound 7, (Camptothecin)-diethylene glycol-(α-lipoic acid):
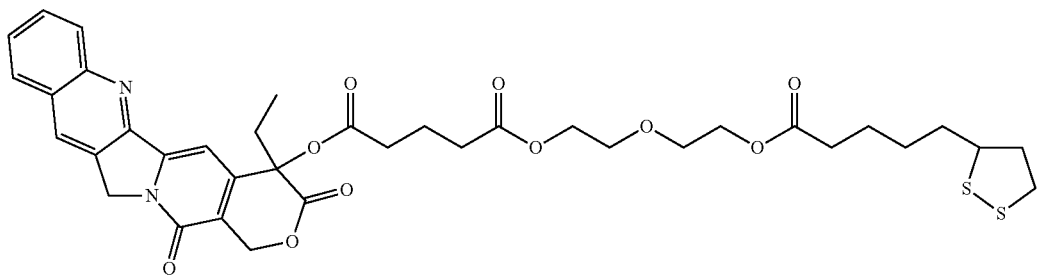 [SMILES: CCC1(OC(=O)CCCC(=O)OCCOCCOC(=O)CCCCC2CCSS2)C(=O)OCc2c1cc1n(c2=O)Cc2cc3ccccc3nc2-1]
Compound 8, (Camptothecin)-triethylene glycol-(α-lipoic acid):
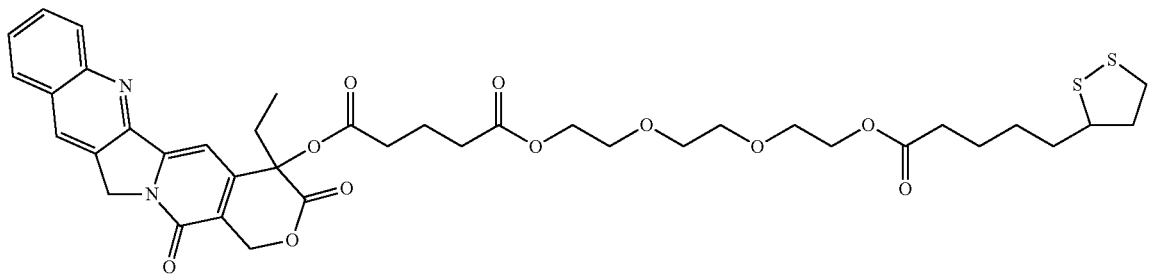 [SMILES: CCC1(OC(=O)CCCC(=O)OCCOCCOCCOC(=O)CCCCC2CCSS2)C(=O)OCc2c1cc1n(c2=O)Cc2cc3ccccc3nc2-1]

Compound 9, (Camptothecin)-hexaethylene glycol-(α-lipoic acid):

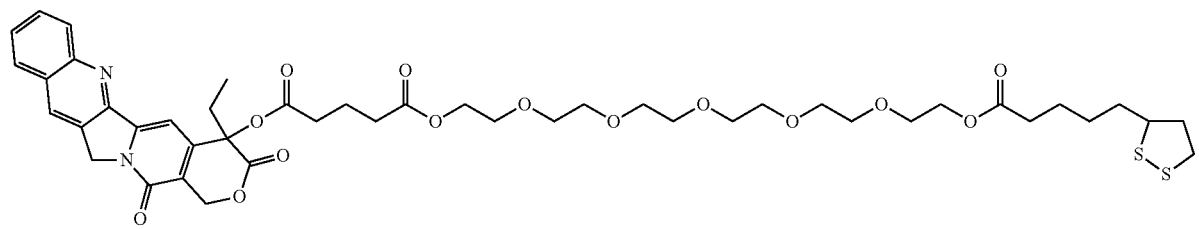 [SMILES: CCC1(OC(=O)CCCC(=O)OCCOCCOCCOCCOCCOCCOC(=O)CCCCC2CCSS2)C(=O)OCc2c1cc1n(c2=O)Cc2cc3ccccc3nc2-1]

Example 4

Synthesis of α-Lipoic Acid Derivative ALA$_2$(1,12-Dodecanediol)

α-Lipoic acid (2.48 g, 12 mmol, 1.2 equiv.) and 1,12-dodecanediol (10 mmol OH, 1.0 equiv.) in 20 mL of anhydrous dichloromethane (DCM) were reacted with 4-(dimethylamino)-pyridine (DMAP, 1.47 g, 12 mmol, 1.2 equiv.) in the presence of molecular sieve (60 Å, 10-20 mesh beads) for 10 min at room temperature. N-(3-Dimethylaminopropyl)-N-ethylcarbodiimide hydrochloride (EDCI, 2.3 g, 12 mmol, 1.2 equiv.) was added portionwise over 10 min and the reaction mixture was stirred for 12 h at room temperature in the dark, filtered, and then concentrated under vacuum to reduce the volume. The resulting reaction mixture was purified using silica gel by direct loading onto the column without further preparation. The solvent was removed under reduced pressure to give the products. $^1$H NMR and $^{13}$C NMR spectra of the compound are provided.

U.S. Provisional Application Ser. No. 61/018,749, filed Jan. 3, 2008, and International Application Publication No. WO 2009/086547, filed Dec. 30, 2008, herein incorporated by reference in their entirety as though fully set forth, provide additional examples of synthesizing α-lipoic acid derivatives that are used in the present invention.

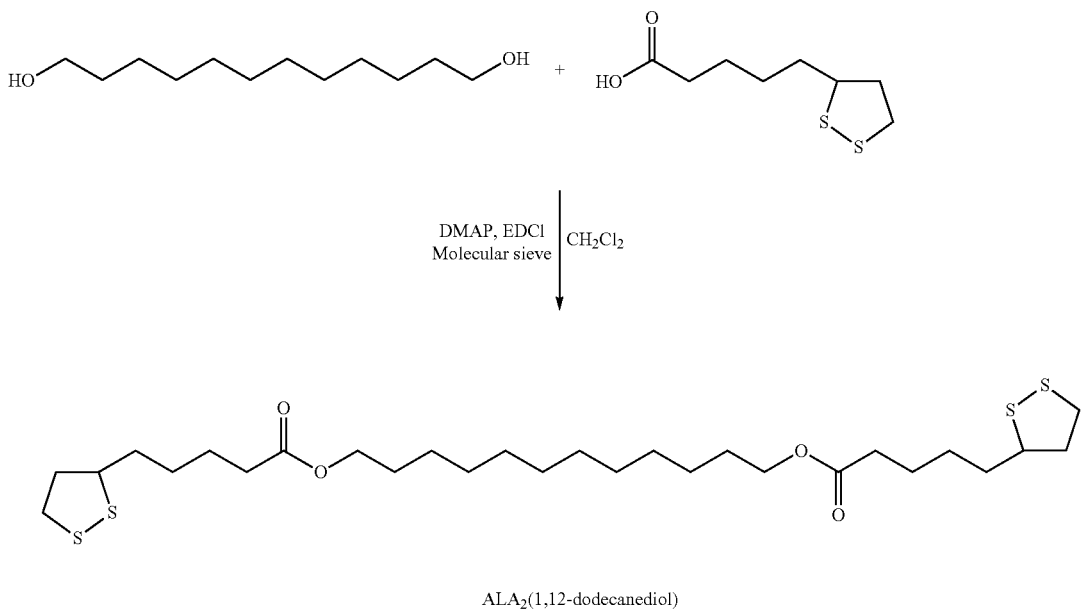

Example 5

Preparation of the Antioxidant-Antineoplastic Nanospheres

Nanospheres were prepared according to the method using spontaneous emulsification with slight modification. Briefly, 15 mg of the compounds (mixture of camptothecin derivatives and ALA$_2$(1,12-dodecanediol)) were dissolved in acetone (5 mL, 0.1% polysorbate 80). The organic solution was poured under moderate stirring on a magnetic plate into an aqueous phase prepared by dissolving 25 mg of Pluronic F68 in 10 mL bidistilled water (0.25% w/v). Following 15 min of magnetic stirring, the acetone was removed under reduced pressure at room temperature. The nanospheres were filtered through 0.8 μm hydrophilic syringe filter and stored at 4° C. The hydrodynamic size measurement and size distribution of the nanospheres was performed by the dynamic light scattering (DLS) using a Coulter N4-Plus Submicron Particle Sizer (Coulter Corporation, Miami, Fla.).

Additionally, 25 mg of the compounds (mixture of the antioxidant camptothecin derivatives, multiple α-lipoic acid containing compounds and α-tocopherol) were dissolved in acetone (5 mL, 0.1% polysorbate 80). The organic solution was poured under moderate stirring on a magnetic plate into an aqueous phase prepared by dissolving 25 mg of Pluronic F68 in 10 mL bidistilled water (0.25% w/v). Following 15 min of magnetic stirring, the acetone was removed under reduced pressure at room temperature. The nanospheres were filtered through 0.8 μm hydrophilic syringe filter and stored at 4° C. The hydrodynamic size measurement and size distribution of the nanospheres was performed by the dynamic light scattering (DLS) using a Coulter N4-Plus Submicron Particle Sizer (Coulter Corporation, Miami, Fla.). Control nanosphere was prepared from multiple α-lipoic acid containing compounds and α-tocopherol in the absence of camptothecin derivatives.

TABLE 1

Size and Polydispersity Index (P.I.):
Antioxidant-Antineoplastic Nanosphere I

| $ALA_2(1,12$-dodecanediol) (mg) | α-Tocopherol (mg) | Compound 10 (mg) | Size (nm) | P.I. |
|---|---|---|---|---|
| 25 | 5 | 0 | 124 ± 32 | 0.09 |
| 25 | 5 | 1 | 132 ± 39 | 0.13 |

Example 6

Preparation of the Antioxidant-Antineoplastic Nanospheres

Nanospheres were prepared according to the method described in Example 5 using spontaneous emulsification from 25 mg of the compounds (mixture of camptothecin derivatives and α-tocopherol). Control nanosphere was prepared from α-tocopherol or $Ibu_2TEG$ in the absence of camptothecin derivatives.

TABLE 2

Size and Polydispersity Index (P.I.):
Antioxidant-Antineoplastic Nanosphere II

| α-Tocopherol (mg) | Compound 10 (mg) | Size (nm) | P.I. |
|---|---|---|---|
| 25 | 1 | 128 ± 45 | 0.25 |
| 25 | 0 | 121 ± 40 | 0.20 |

Example 7

Preparation of the Anti-Inflammatory-Antineoplastic Nanosphere

Nanospheres were prepared according to the method described in Example 5 using spontaneous emulsification from 25 mg of the compounds (mixture of camptothecin derivatives, derivatives of non-steroidal anti-inflammatory drugs (NSAIDs) and α-tocopherol). Control nanosphere was prepared from α-tocopherol or a mixture of α-tocopherol and derivatives of NSAIDs in the absence of camptothecin derivatives.

TABLE 3

Size and Polydispersity Index (P.I.):
Anti-inflammatory-Antineoplastic Nanosphere

| $Ibu_2TEG$ (mg) | α-Tocopherol (mg) | Compound 10 (mg) | Size (nm) | P.I. |
|---|---|---|---|---|
| 25 | 5 | 1 | 124 ± 32 | 0.09 |
| 25 | 5 | 0 | 130 ± 34 | 0.09 |

Example 8

Anticancer and Antiproliferative Effects of the Nanospheres Comprising Camptothecin Derivatives The U87-MG human glioma cell line was obtained from American Type Culture Collection (ATCC) (Rockville, Md., USA). The cells were grown and maintained in Minimum Essential Medium (MEM) (Invitrogen) containing antibiotics 100 U/mL penicillin (Invitrogen) and 100 μg/mL streptomycin (Invitrogen), and supplemented with 10% fetal bovine serum (FBS) (Invitrogen). Cells were kept at 37° C. in a humidified atmosphere including 5% $CO_2$.

Figure 5:
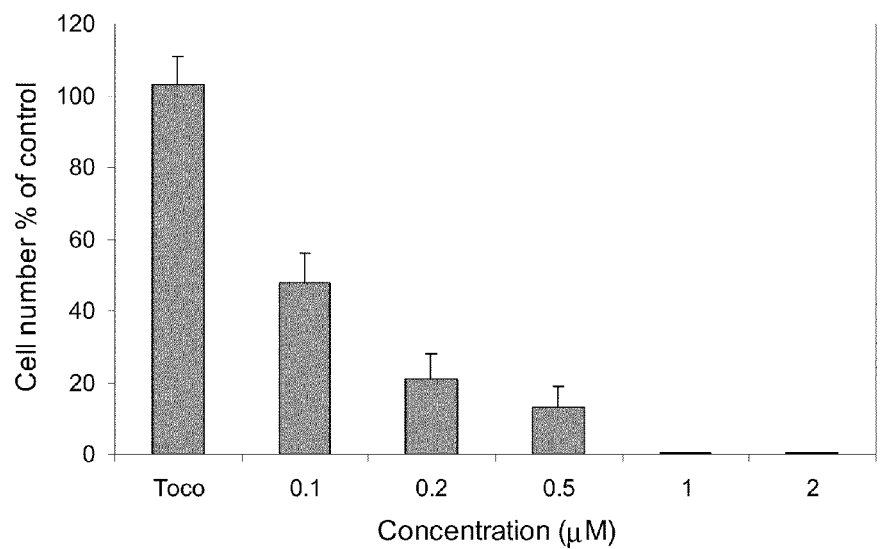
FIG. 5 depicts the effect of nanospheres comprising Compound 10 on glioma cell viability in accordance with an embodiment of the present invention. Control nanospheres prepared from α-tocopherol only in the absence of Compound 10 (Toco); cells are treated with nanospheres prepared from a mixture of α-tocopherol and Compound 10, which contained 0.1-2.0 μM of Compound 10. Error bar represents ±S.D. calculated from triplicate determinations.
Figure 6:
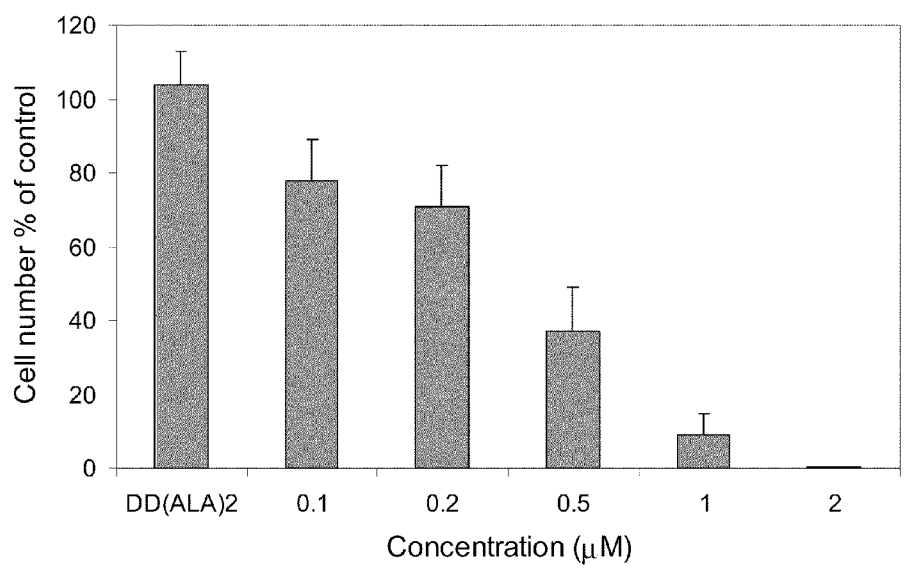
FIG. 6 depicts the effect of nanospheres comprising Compound 10 on glioma cell viability in accordance with an embodiment of the present invention. Control nanospheres prepared from ALA$_2$(1,12-dodecanediol) only in the absence of Compound 10 (DD(ALA2)); cells treated with nanospheres prepared from a mixture of ALA$_2$(1,12-dodecanediol) and Compound 10, which contained 0.1-2.0 μM of Compound 10. Error bar represents ±S.D. calculated from triplicate determinations.
Figure 7:
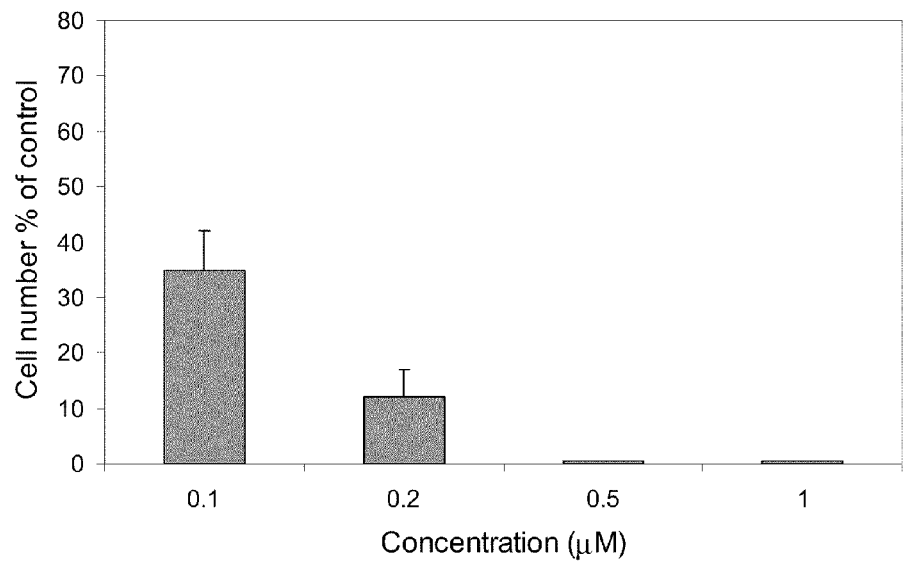
FIG. 7 depicts the effect of nanospheres comprising Compound 10 and Ibu$_2$TEG on glioma cell viability in accordance with an embodiment of the present invention. Cells treated with nanospheres prepared from a mixture of Ibu$_2$TEG and Compound 10, which contained 0.1-2.0 μM of Compound 10. For control experiment with nanospheres prepared from Ibu$_2$TEG only in the absence of Compound 10, see FIG. 8. Error bar represents ±S.D. calculated from triplicate determinations.
Figure 8:
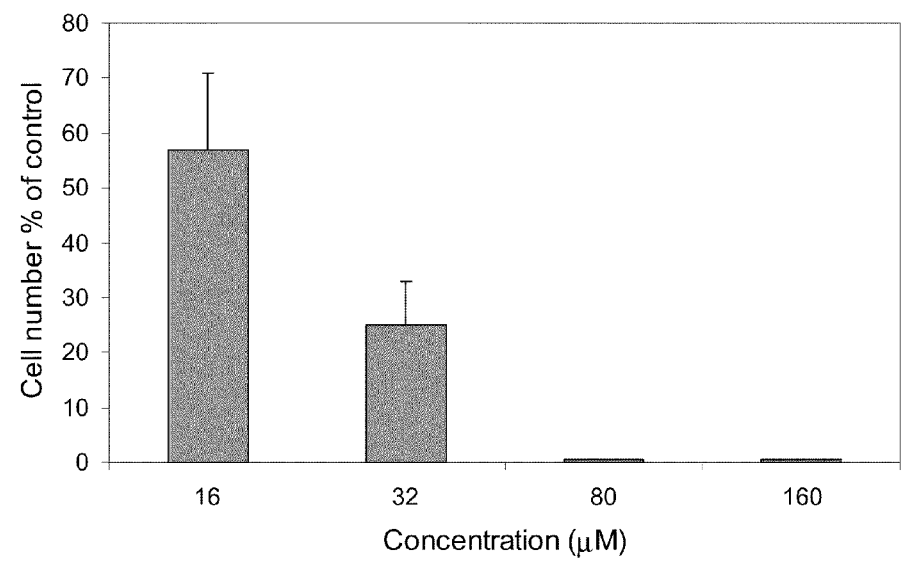
FIG. 8 depicts the effect of nanospheres containing Ibu$_2$TEG on glioma cell viability in accordance with an embodiment of the present invention. Cells were treated with nanospheres prepared from Ibu$_2$TEG only which contained 16-160 μM of Ibu$_2$TEG. The amount of Ibu$_2$TEG in this experiment is equal to the amount of Ibu$_2$TEG contained in the nanospheres prepared from a mixture of Ibu$_2$TEG and Compound 10 (FIG. 7). Thus, the results serve as a control for the experiment of FIG. 7 in the absence of Compound 10. Error bar represents ±S.D. calculated from triplicate determinations.
Figure 9:
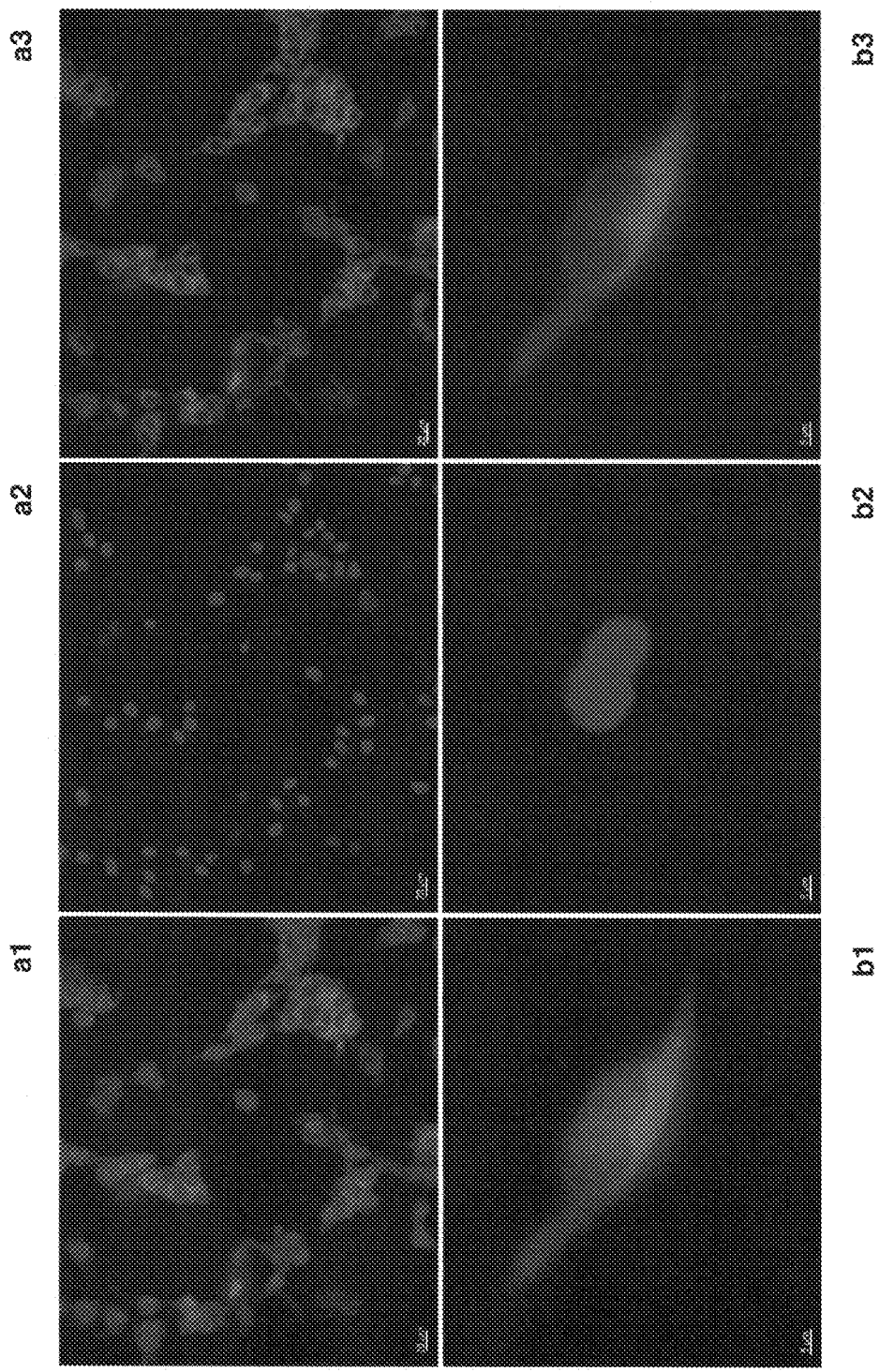
FIG. 9 depicts in vitro cellular uptake of the CM6 fluorescent-labeled antioxidant-antineoplastic nanosphere CPT-TEG-ALA/Toco in accordance with an embodiment of the present invention. In vitro cellular uptake of fluorescent-labeled antioxidant-antineoplastic nanosphere CPT-TEG-ALA/Toco in U87 glioma cells. Cells were incubated with CM6-labeled CPT-TEG-ALA/Toco nanosphere for 5 h. The panels show images of overlapped fluorescence of DAPI and CM6 (a1 and b1), DAPI (a2 and b2) and CM6 (a3 and b3).
Figure 10:
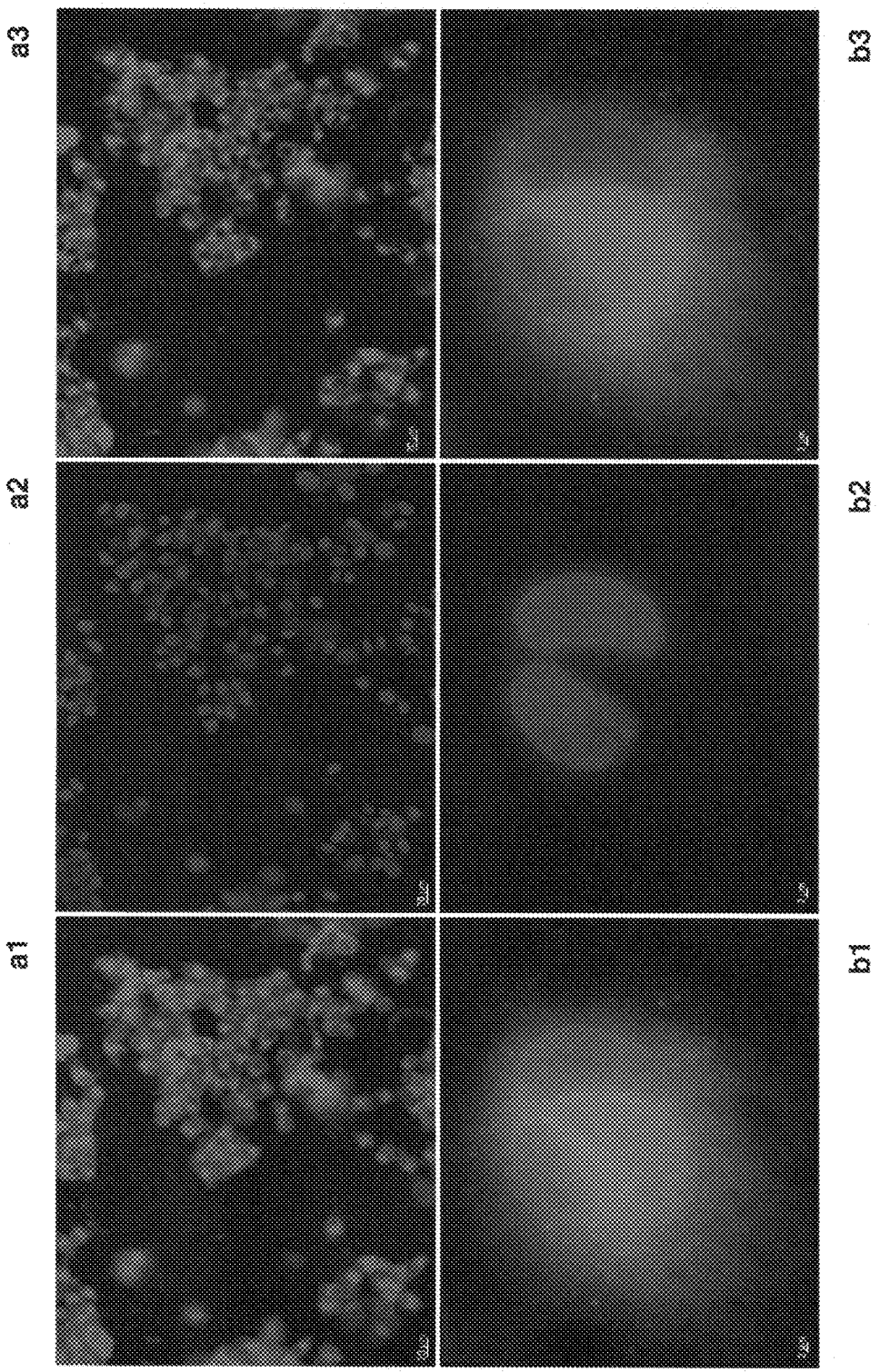
FIG. 10 depicts in vitro cellular uptake of the Cy3 fluorescent-labeled antioxidant-antineoplastic nanosphere CPT-TEG-ALA/Toco in accordance with an embodiment of the present invention. In vitro cellular uptake of fluorescent-labeled antioxidant-antineoplastic nanosphere CPT-TEG-ALA/Toco in U87 glioma cells. Cells were incubated with Cy3-labeled CPT-TEG-ALA/Toco nanosphere for 5 h. The panels show images of overlapped fluorescence of DAPI and Cy3 (a1 and b1), DAPI (a2 and b2) and cy3 (a3 and b3).
Figure 11:
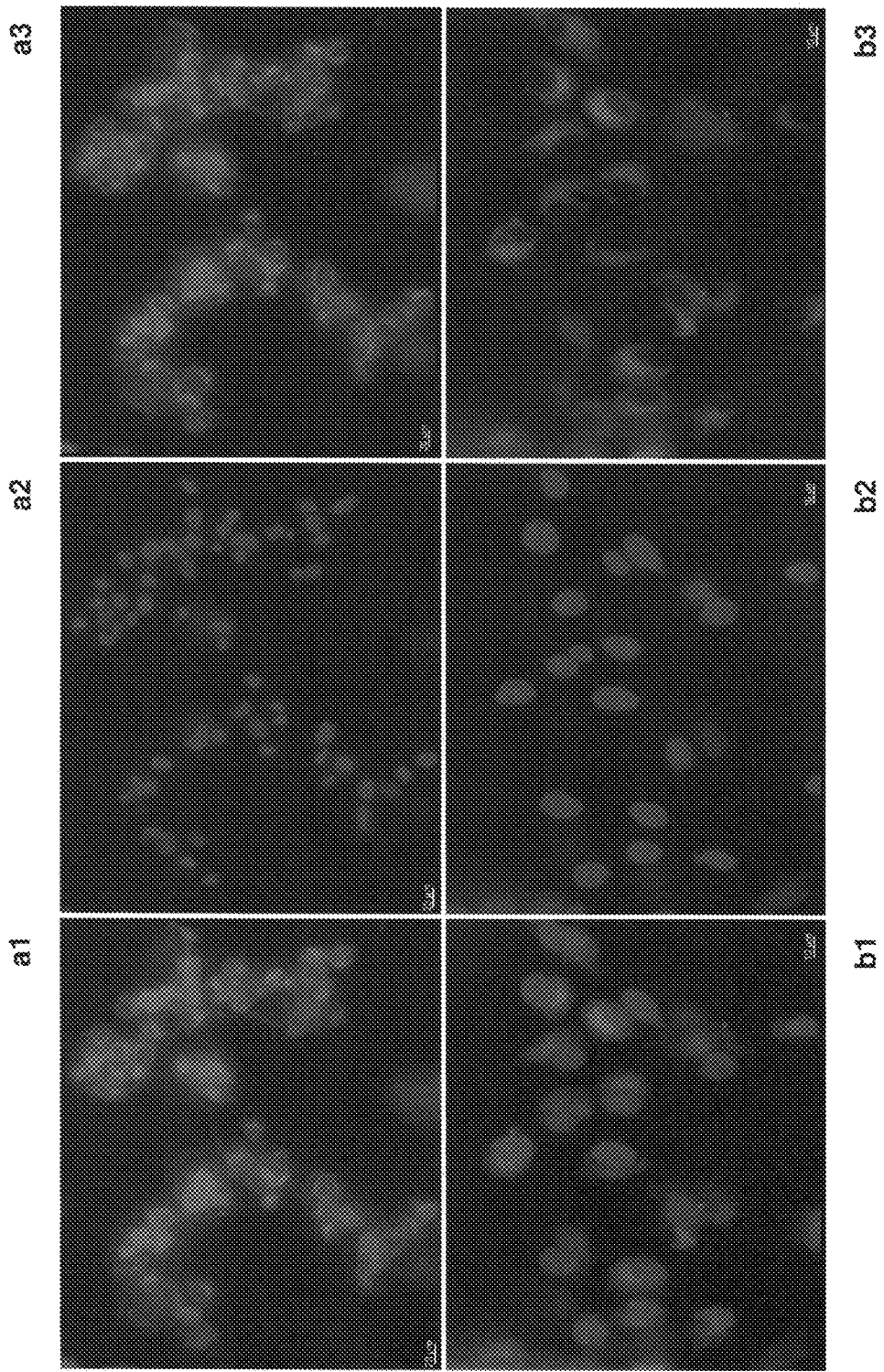
FIG. 11 depicts in vitro cellular uptake of the Cy5.5 fluorescent-labeled antioxidant-antineoplastic nanosphere CPT-TEG-ALA/Toco in accordance with an embodiment of the present invention. In vitro cellular uptake of fluorescent-labeled antioxidant-antineoplastic nanospheres CPT-TEG-ALA/Toco in U87 glioma cells. Cells were incubated with cy5-labeled CPT-TEG-ALA/Toco nanosphere for 5 h. The panels show images of overlapped fluorescence of DAPI and cy5.5 (a1 and b1), DAPI (a2 and b2) and cy5.5 (a3 and b3).
Figure 12:
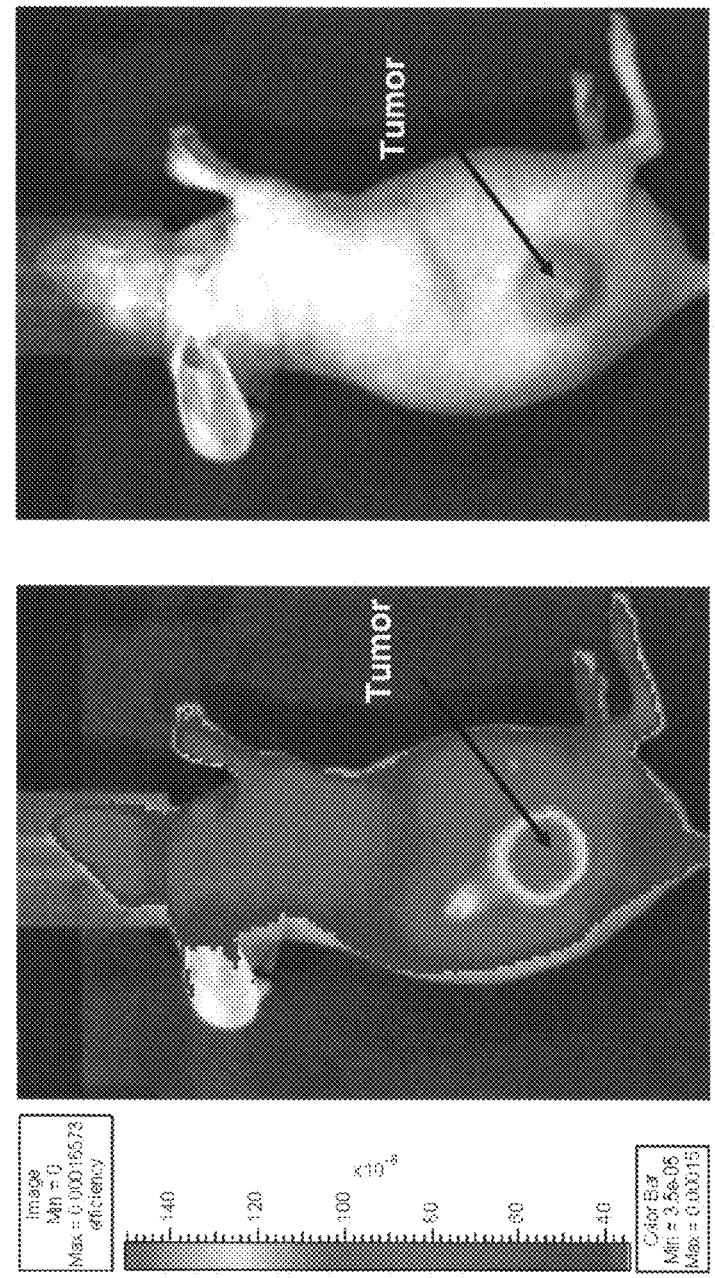
FIG. 12 depicts in vivo fluorescent imaging of mouse bearing subcutaneous tumor 72 h after i.v. injection with the antioxidant-antineoplastic nanosphere CPT-TEG-ALA/Toco in accordance with an embodiment of the present invention. Intra-tumoral accumulation of the fluorescent-labeled nanoprodrug in subcutaneous tumor of U87 glioma cells. The in vivo fluorescent imaging was performed using Xenogen IVIS 200 imaging system. The red zone indicates where the fluorescent-labeled nanosphere has been accumulated in the body.
Figure 13:
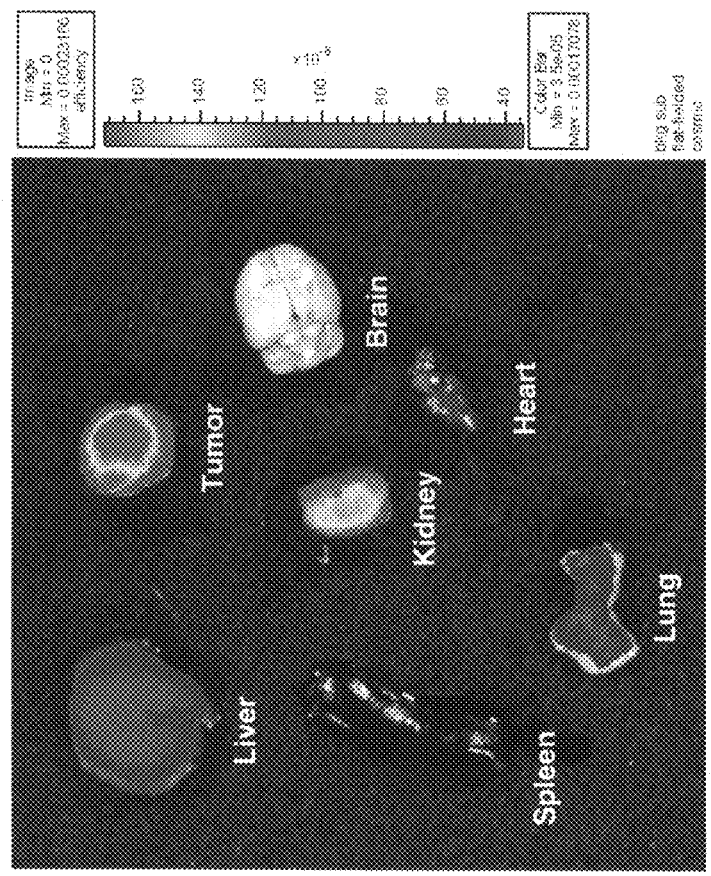
FIG. 13 depicts fluorescent imaging of the organs harvested from the mouse 72 h after i.v. injection with the antioxidant-antineoplastic nanosphere CPT-TEG-ALA/Toco in accordance with an embodiment of the present invention. Intra-tumoral accumulation of the fluorescent-labeled CPT-TEG-ALA/Toco nanosphere in subcutaneous tumor of U87 glioma cells and other organs. The fluorescent imaging was performed using Xenogen IVIS 200 imaging system. The red zone indicates where the fluorescent-labeled nanospheres has been accumulated in the organs.
Figure 14:
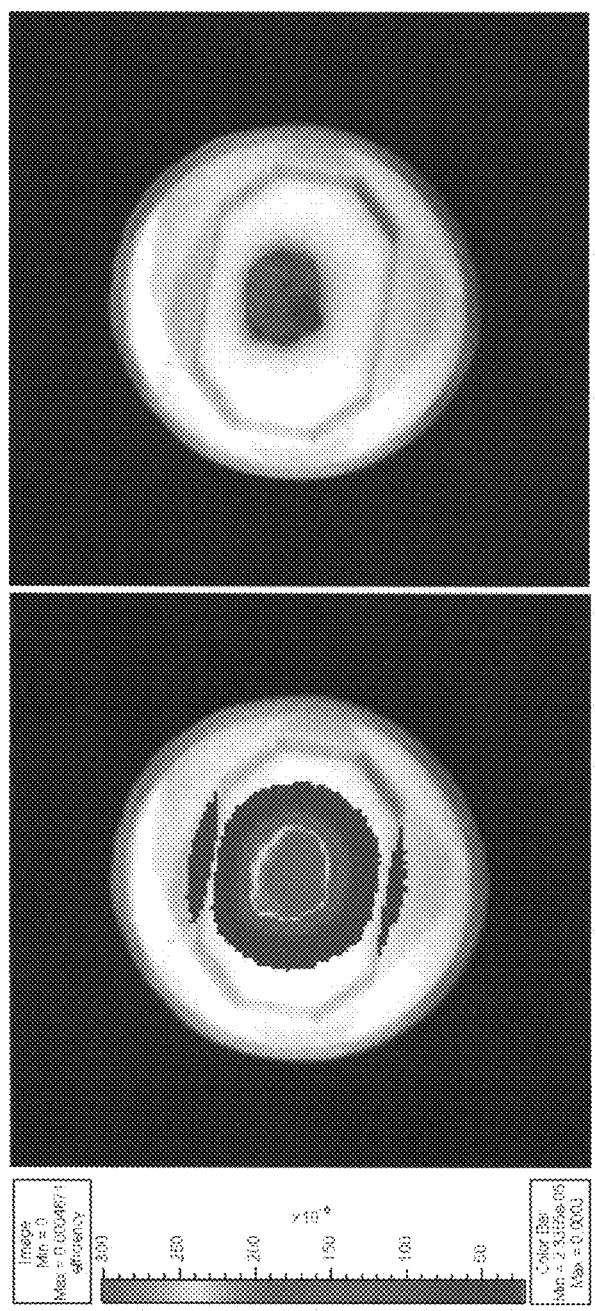
FIG. 14 depicts fluorescent imaging of the tumor section in OCT block harvested from the mouse 72 h after i.v. injection with the antioxidant-antineoplastic nanosphere CPT-TEG-ALA/Toco in accordance with an embodiment of the present invention.
Figure 15:
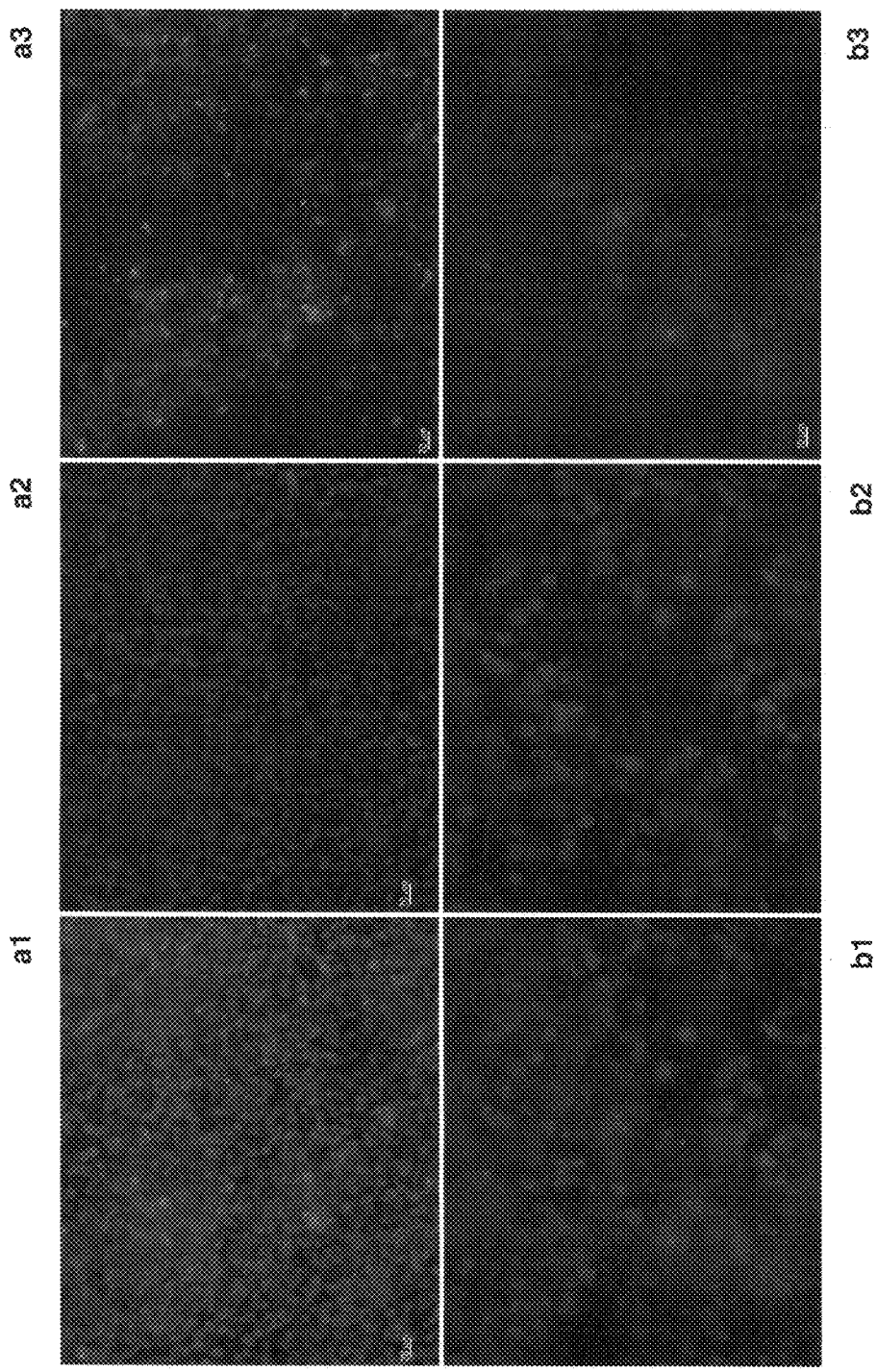
FIG. 15 depicts intra-tumoral accumulation of the fluorescent-labeled antioxidant-antineoplastic nanosphere CPT-TEG-ALA/Toco in the subcutaneous tumor section as determined by confocal fluorescence microscopy in accordance with an embodiment of the present invention. Intra-tumoral accumulation of fluorescent-labeled nanosphere in U87 subcutaneous tumor in mouse. The panels show images of the sections of subcutaneous tumor harvested 72 h after i.v. injection of the nanosphere (a: 20×; b: 40×) with overlapped fluorescence of DAPI and cy5 (a1 and b1), DAPI (a2 and b2) and cy5 (a3 and b3).
Figure 16:
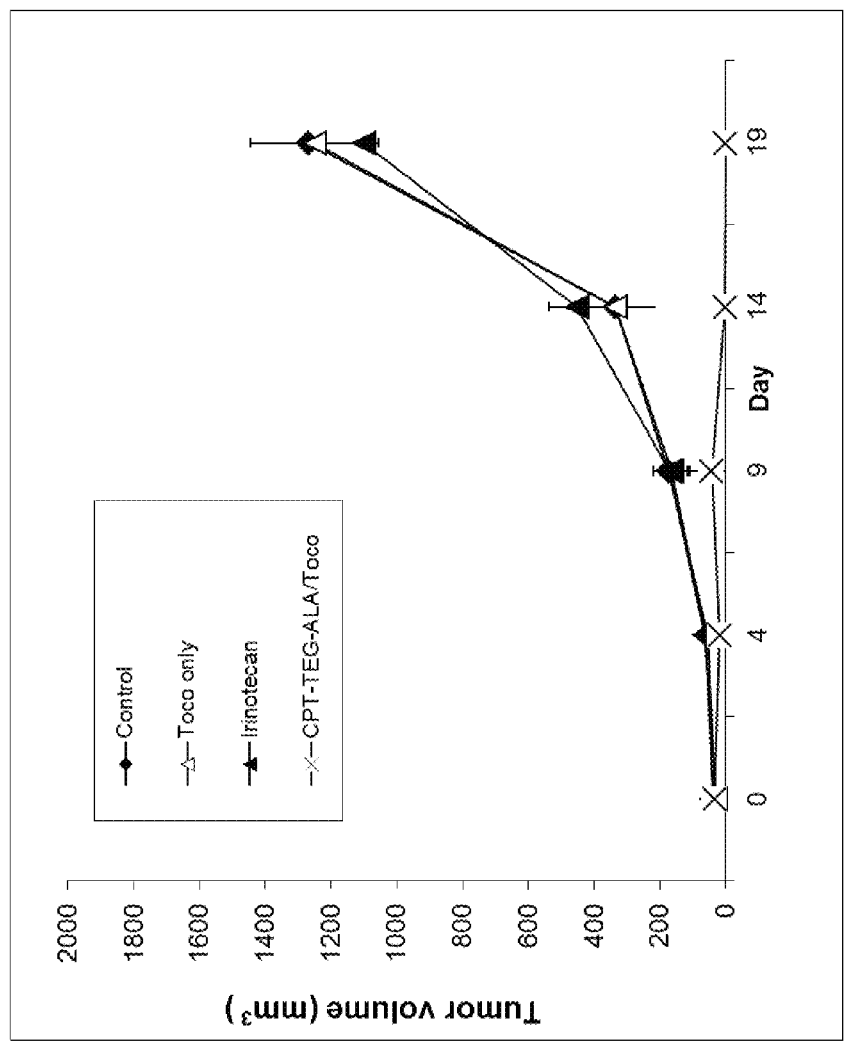
FIG. 16 depicts subcutaneous tumor suppression by CPT-TEG-ALA/Toco in accordance with an embodiment of the present invention. The treatment was started when the tumor size reached approx. 0.5 cm in diameter (day 0). The animals are pair-matched into treatment and control groups.
Figure 17:
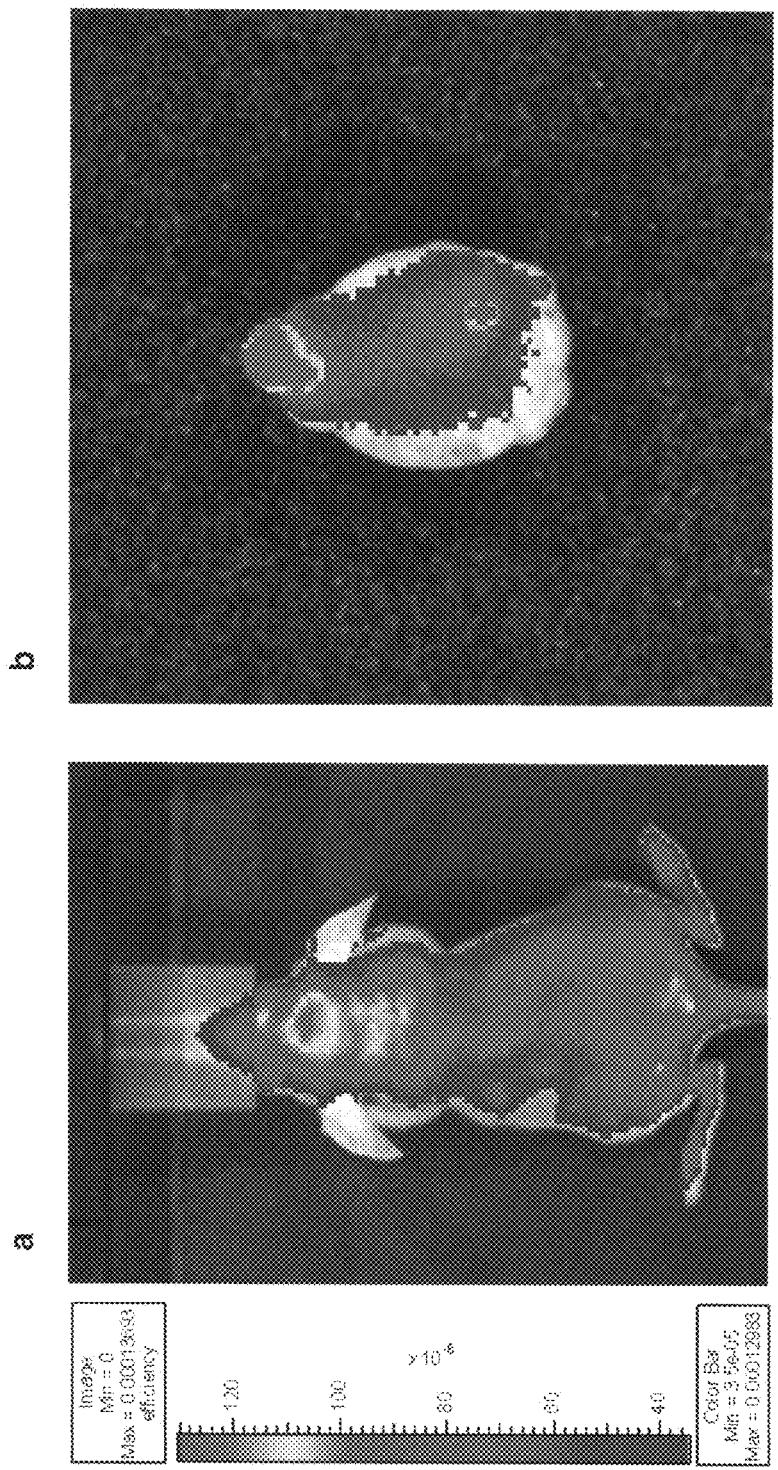
FIG. 17 depicts in vivo fluorescent imaging of brain tumor-bearing mouse and brain 24 h after i.v. injection with the antioxidant-antineoplastic nanosphere CPT-TEG-ALA/Toco in accordance with an embodiment of the present invention. Intra-tumoral accumulation of the fluorescent-labeled nanosphere in brain tumor (U87 glioma). The in vivo fluorescent imaging was performed using Xenogen IVIS 200 imaging system equipped with cy5.5 filter. The panels shows the imaging of whole body (a) and isolated brain bearing tumor. The red zone indicates where the fluorescent-labeled nanosphere has been accumulated in the body (a) and in the tumor-bearing brain (b).
Figure 18:
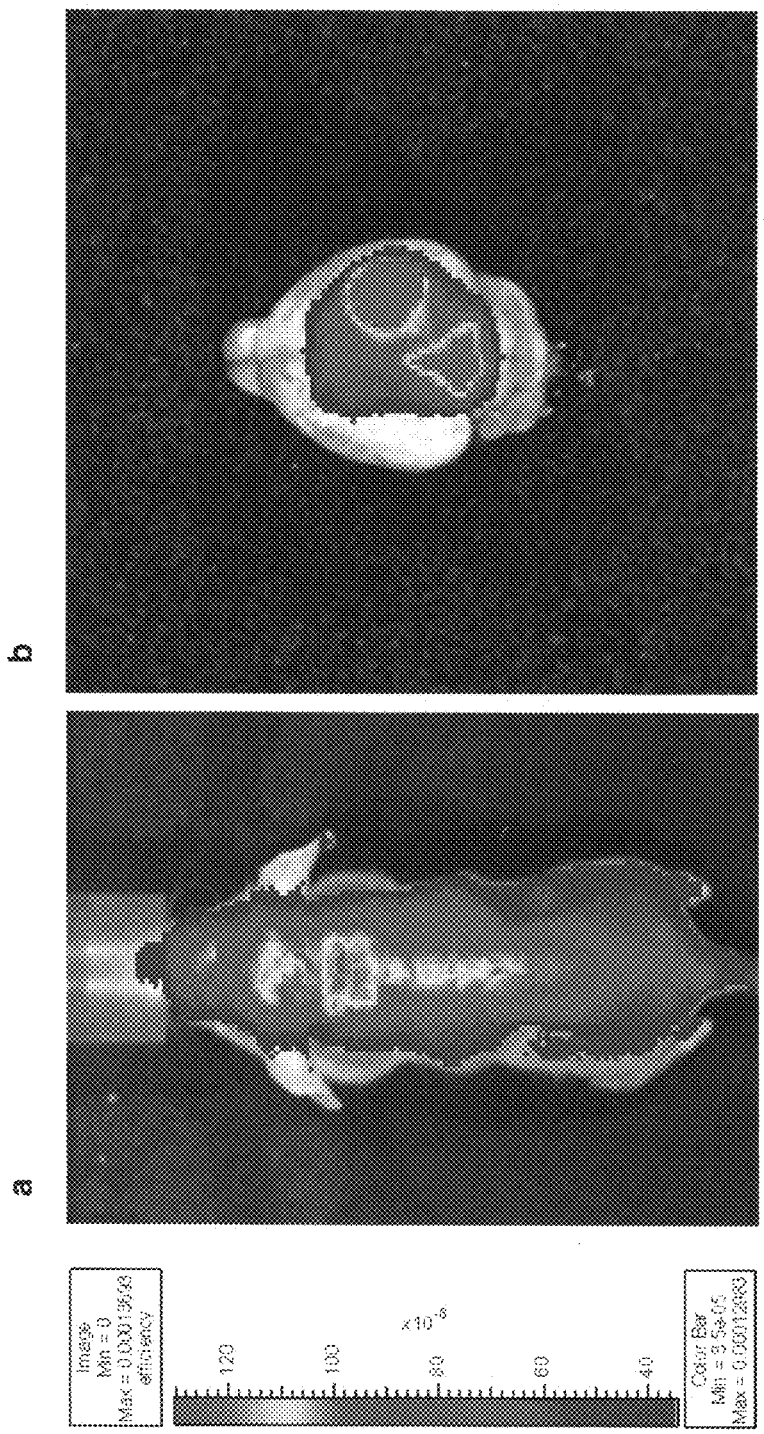
FIG. 18 depicts in vivo fluorescent imaging of brain tumor-bearing mouse and brain 5 h after i.v. injection with the antioxidant-antineoplastic nanosphere CPT-TEG-ALA/Toco in accordance with an embodiment of the present invention. Intra-tumoral accumulation of the fluorescent-labeled nanosphere in brain tumor (U87 glioma). The in vivo fluorescent imaging was performed using Xenogen IVIS 200 imaging system equipped with cy5.5 filter. The panels shows the imaging of whole body (a) and isolated brain tumor-bearing mouse brain. The red zone indicates where the fluorescent-labeled nanosphere has been accumulated in the body (a) and in the tumor-bearing brain (b).
Figure 19:
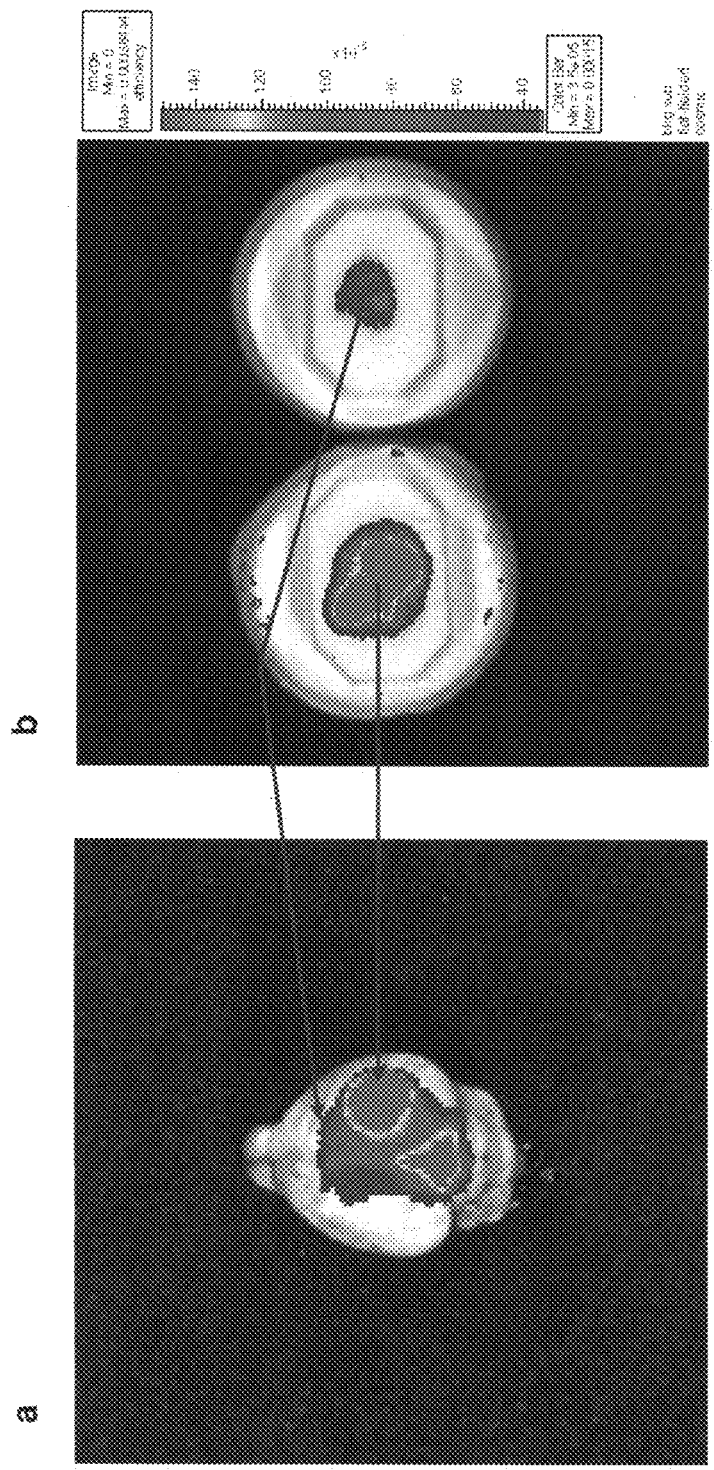
FIG. 19 depicts fluorescent imaging of brain tumor-bearing brain harvested 5 h after i.v. injection with the antioxidant-antineoplastic nanosphere CPT-TEG-ALA/Toco in accordance with an embodiment of the present invention. Intra-tumoral accumulation of the fluorescent-labeled nanosphere in brain tumor (U87 glioma). The imaging was performed using Xenogen IVIS 200 imaging system equipped with cy5.5 filter. The panels shows the imaging of the whole brain tumor-bearing brain (a) and brain tumor sections cut through the brain as shown by the arrows (b). The red zone indicates where the fluorescent-labeled nanosphere has been accumulated in the brain.
Figure 20:
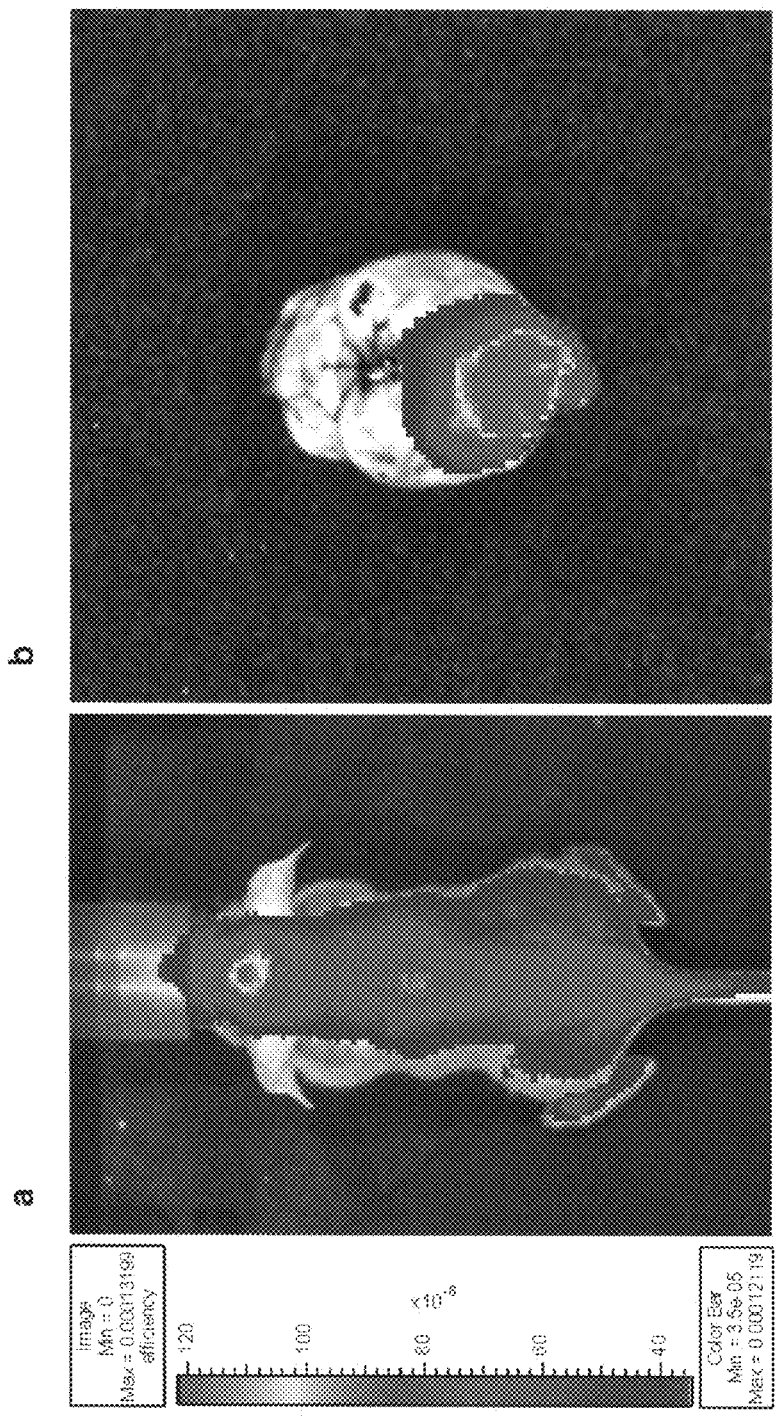
FIG. 20 depicts in vivo fluorescent imaging of brain tumor-bearing mouse and brain 24 h after i.v. injection with the antioxidant-antineoplastic nanosphere CPT-TEG-ALA/Toco in accordance with an embodiment of the present invention. Intra-tumoral accumulation of the fluorescent-labeled nanosphere in brain tumor (U87 glioma). The in vivo fluorescent imaging was performed using Xenogen IVIS 200 imaging system equipped with cy5.5 filter. The panels shows the imaging of whole body (a) and isolated brain bearing tumor. The red zone indicates where the fluorescent-labeled nanosphere has been accumulated in the body (a) and in the tumor-bearing brain (b).
Figure 21:
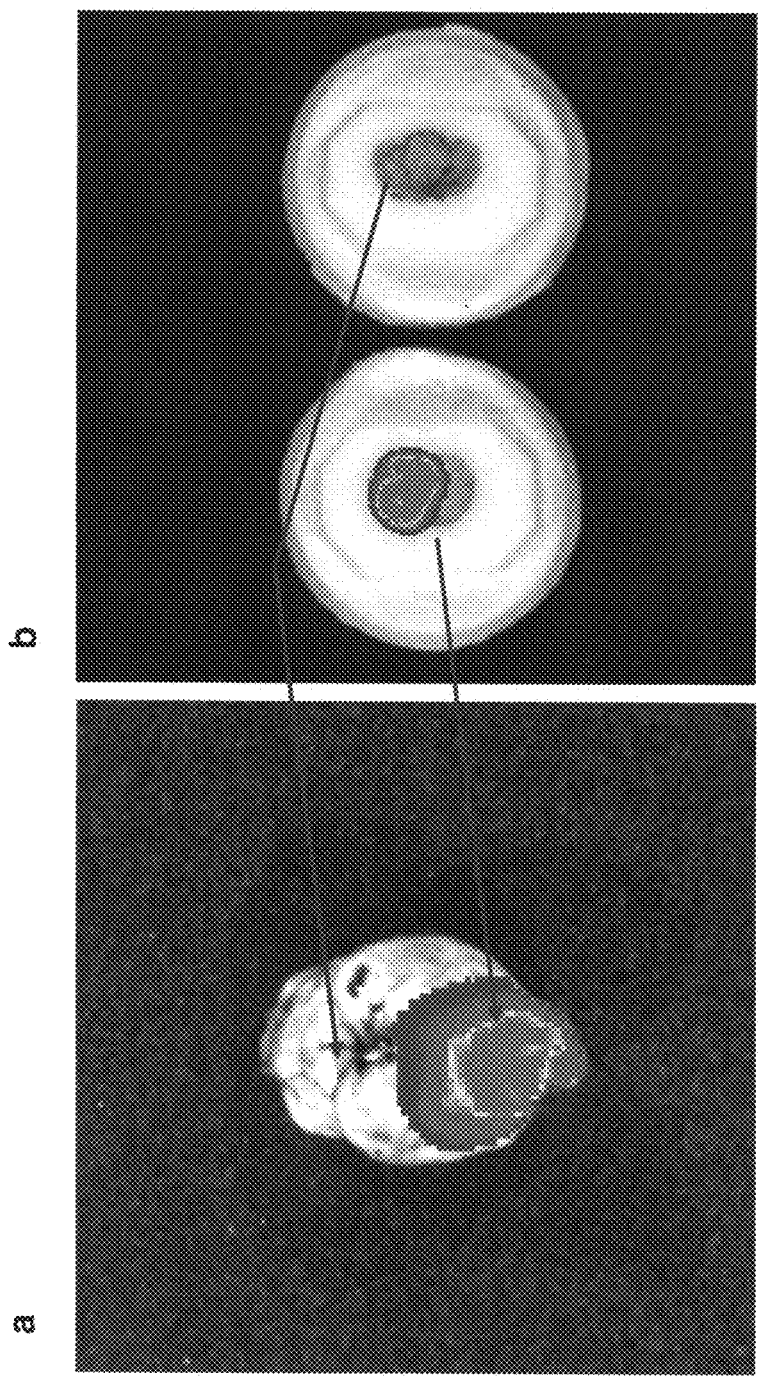
FIG. 21 depicts fluorescent imaging of brain tumor-bearing brain harvested 24 h after i.v. injection with CPT-TEG-ALA/Toco nanoprodrug in accordance with an embodiment of the present invention. Intra-tumoral accumulation of the fluorescent-labeled nanosphere in brain tumor (U87 glioma). The imaging was performed using Xenogen IVIS 200 imaging system equipped with cy5.5 filter. The panels shows the imaging of the whole brain tumor-bearing brain (a) and brain tumor sections cut through the brain as shown by the arrows (b). The red zone indicates where the fluorescent-labeled nanosphere has been accumulated only in the brain tumor, but not in the normal brain.
Figure 22:
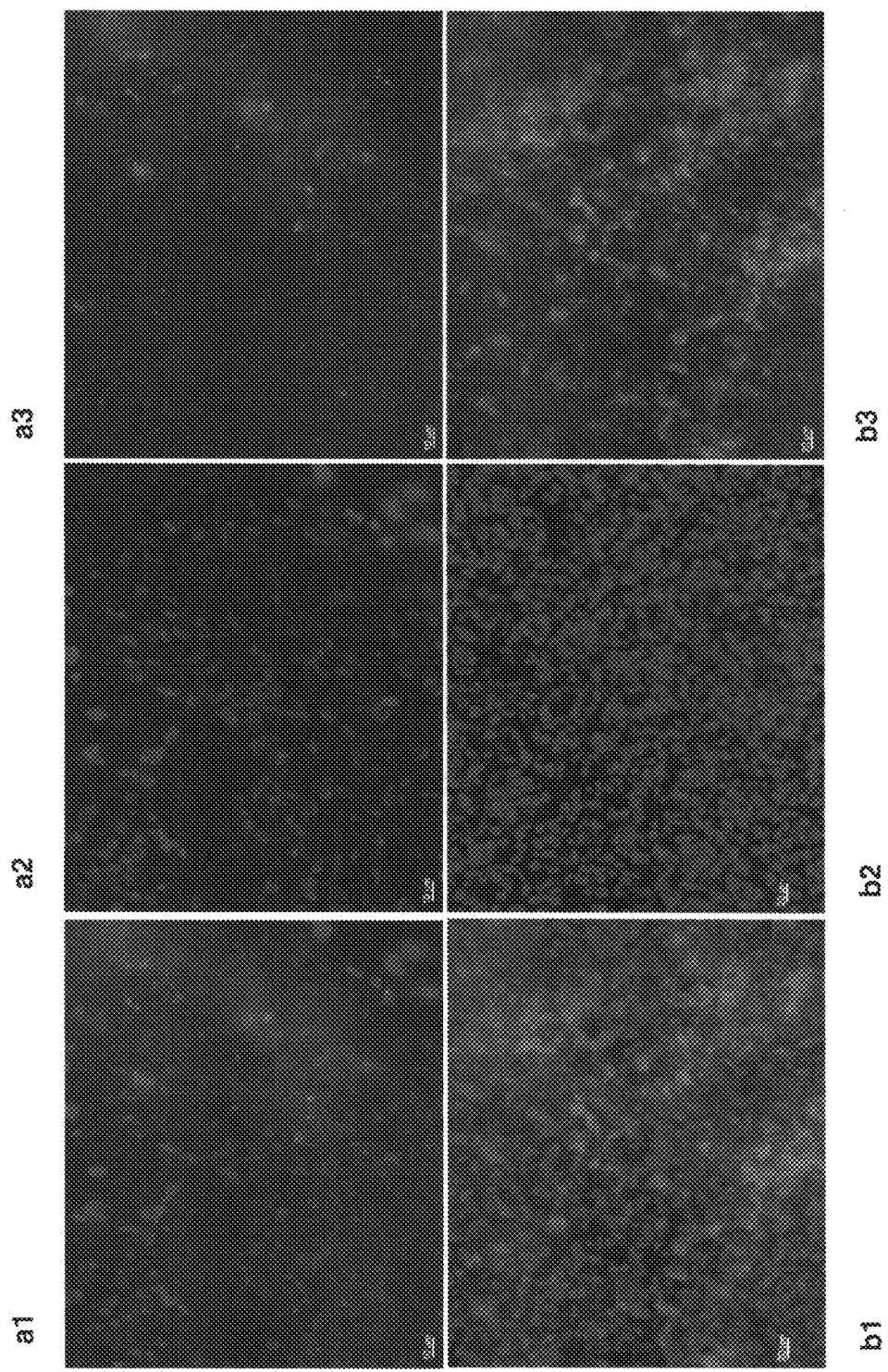
FIG. 22 depicts intra-tumoral accumulation of the fluorescent-labeled antioxidant-antineoplastic nanosphere CPT-TEG-ALA/Toco in the brain tumor section as determined by confocal fluorescence microscopy in accordance with an embodiment of the present invention. Intra-tumoral accumulation of fluorescent-labeled nanosphere in U87 glioma in mouse. The panels show images (a: 40×; b: 20×) of sections of tumor-bearing brain harvested 5 h (a1-a3) and 24 h (b1-b3) after i.v. injection of the nanosphere with overlapped fluorescence of DAPI and cy5 (a1 and b1), DAPI (a2 and b2) and cy5 (a3 and b3).
Figure 23:
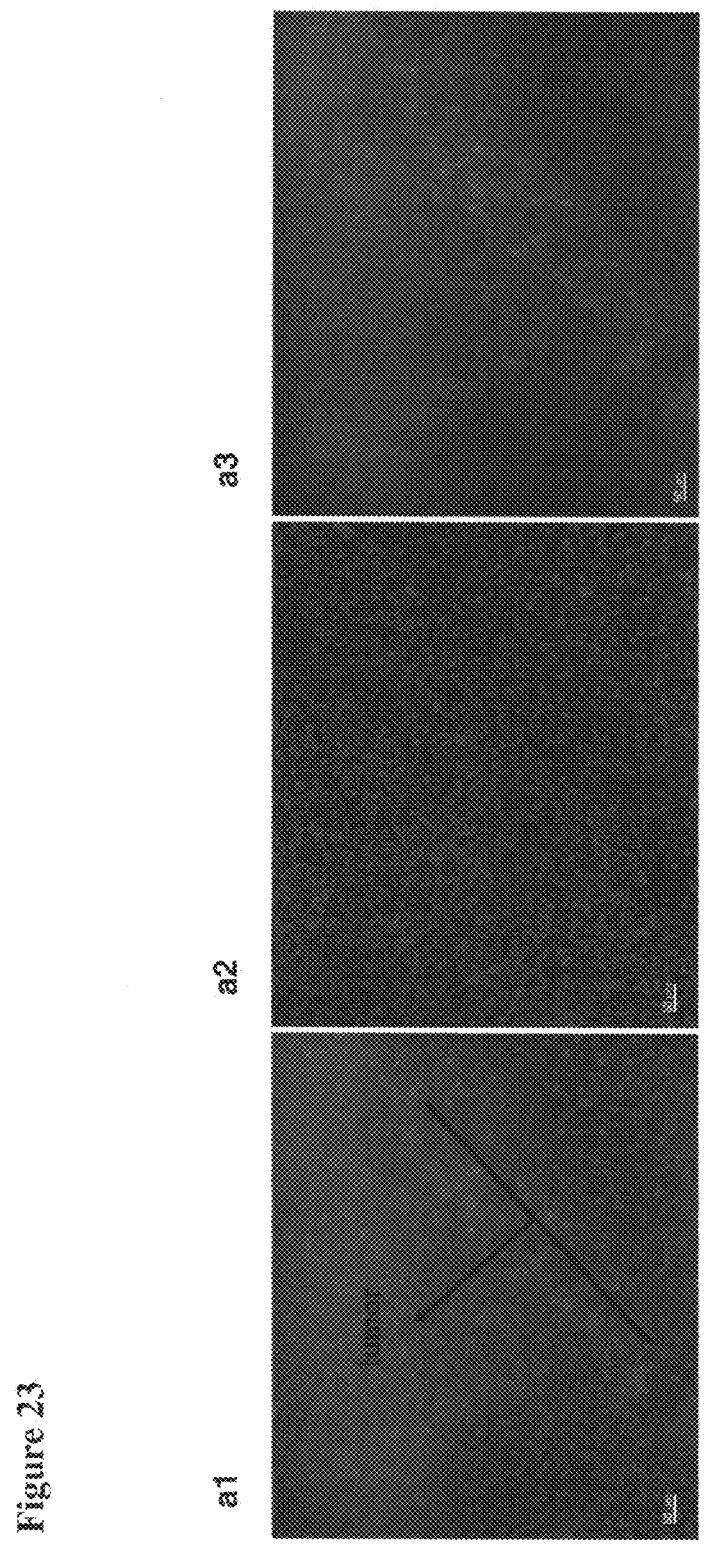
FIG. 23 depicts intra-tumoral accumulation of the fluorescent-labeled antioxidant-antineoplastic nanosphere CPT-TEG-ALA/Toco in the brain tumor section as determined by confocal fluorescence microscopy in accordance with an embodiment of the present invention. Intra-tumoral accumulation of fluorescent-labeled nanosphere in U87 glioma in mouse. The panels show images of a section of tumor-bearing brain harvested 24 h after i.v. injection of the nanosphere with overlapped fluorescence of DAPI and cy5 (a1), DAPI (a2) and cy5 (a3). The border area between the tumor and normal tissue is clearly distinguishable.

Nanospheres were prepared from the mixture of Compound 10 (1 mg), α-tocopherol (25 mg), and multiple α-lipoic acid containing compound $(ALA)_3$Glycerol; or Compound 10 (1 mg) and α-tocopherol (25 mg); or Compound 10 (1 mg), α-tocopherol (25 mg), and NSAID derivative $Ibu_2TEG$ as described in Examples 5, 6, and 7, and dialyzed in phosphate buffered saline (PBS) overnight. The human glioma cells (U87-MG) were seeded in a 6-well flask at $10^5$ cells/well and allowed to grow for 24 h. The medium was changed and the cells were treated with nanospheres at final concentration ranging from 0.1 to 2 μM for the Compound 10. After a 4-day treatment, the medium was remove, cells were washed with PBS and 1 mL of 0.25% trypsin/EDTA (Gibco) was added to detach the cells. The cells were counted immediately in a hemacytometer (See FIGS. 5-8). Control culture was grown in the absence of nanospheres.

Example 9

Synthesis of Bifunctional Derivatives of α-Lipoic Acid and NSAIDs

α-Lipoic acid (ALA, 10 mmol) and tetraethylene glycol (TEG, 30 mmol) in 50 ml of anhydrous dichloromethane (DCM) were reacted with 4-(dimethylamino)-pyridine (DMAP, 15 mmol) in the presence of a molecular sieve (Fluka, 3 Å, 10-20 mesh beads) for 10 min at room temperature. N-(3-Dimethylaminopropyl)-N-ethylcarbodiimide hydrochloride (EDCI, 10 mmol) was added portionwise over 10 min and the reaction mixture was stirred for 5 h at room temperature in the dark, filtered, and then concentrated under vacuum to reduce the volume. The product ALA-TEG-OH and dimeric byproduct ALA-TEG-ALA were purified using column chromatography by loading the concentrated reaction mixture on the column without prior preparation and characterized as described above. Mono-ALA derivatives of TEG (3.8 mmol) and NSAIDs (4.1 mmol, indomethacin: Ind, ibuprofen: Ibu, naproxen: Npx) in 20 ml of anhydrous DCM were reacted with DMAP (4.1 mmol) in the presence of molecular sieve for 10 min at room temperature. EDCI (4.1 mmol) was added portionwise over 10 min and the reaction mixture was stirred for 5 h at room temperature in the dark, filtered, and then concentrated under vacuum at room temperature. The products were purified using column chromatography and characterized as described above.

International Application No. PCT/US09/39956, filed on Apr. 8, 2009, which is incorporated by reference in its entirety as though fully set forth, provides additional examples of synthesizing bifunctional derivatives of α-lipoic acid and NSAIDs.

Example 10

Synthesis of Dimeric Derivatives of NSAIDs

NSAIDs (6 mmol) and TEG (2.5 mmol) in 40 ml of anhydrous DCM were reacted with DMAP (6 mmol) in the presence of molecular sieve for 10 min at room temperature. EDCI (6 mmol) was added portionwise over 10 min and the reaction mixture was stirred for 5 h at room temperature in the dark, filtered, and then concentrated under vacuum. The products were purified (column chromatography, 100:0.5 $CH_3Cl$:MeOH) and characterized as described above.

International Application No. PCT/US09/39956, filed on Apr. 8, 2009, which is incorporated by reference in its entirety as though fully set forth, provides additional examples of synthesizing dimeric derivatives of NSAIDs.

Example 11

Preparation of the Antioxidant-Antineoplastic Nanospheres Using Multiple-Step Spontaneous Emulsification to Increase Concentration To prepare the antioxidant-antineoplastic nanospheres with a higher concentration, a multiple-step spontaneous emulsification was applied. Generally, 25-100 mg of the compounds (mixture of the antioxidant camptothecin derivatives, multiple α-lipoic acid containing compounds, derivatives of non-steroidal anti-inflammatory drugs (NSAIDs) and α-tocopherol) were dissolved in acetone (5 mL, 0.1% polysorbate 80). The organic solution was poured under moderate stirring on a magnetic plate into an aqueous phase prepared by dissolving 25 mg of Pluronic F68 in 10 mL bidistilled water (0.25% w/v). Following 15 min of magnetic stirring, the acetone was removed under reduced pressure at room temperature. The combined process of spontaneous emulsification and removal of acetone was repeated up to five times using the same aqueous suspension.

The suspension was dialyzed in cellulose membrane tube (Sigma, code D9777) overnight in distilled water and filtered through 0.45 μm hydrophilic syringe filter (Sigma, code CLS431220) and stored at 4° C. The hydrodynamic size measurement and size distribution of the nanospheres was performed by the dynamic light scattering (DLS) using a Coulter N4-Plus Submicron Particle Sizer (Coulter Corporation, Miami, Fla.).

Example 12

Preparation of the Fluorescent-Labeled Antioxidant-Antineoplastic Nanospheres

To demonstrate intracellular uptake in vitro cell culture, distribution in animal body, and intra-tumoral accumulation of the antioxidant-antineoplastic nanospheres, we prepared antioxidant-antineoplastic nanospheres labeled with a hydrophobic dye Coumarin 6 (Sigma, code 442631) or with a hydrophilic dye cy3/cy5/cy5.5 (GE Healthcare Life Sciences). Coumarin 6-labeled antioxidant-antineoplastic nanospheres were prepared using identical procedure as described in Example 5-Example 8 except that 50 μg of the dye was added to the organic phase prior to spontaneous emulsification. The incorporated Coumarin 6 remains associated with antioxidant-antineoplastic nanospheres during dialysis overnight.

To prepare cy3/cy5/cy5.5-labeled antioxidant-antineoplastic nanospheres, antioxidant-antineoplastic nanospheres were prepared using identical procedure as described in Example 5-Example 8 except that 0.1-2 mg of 1-octadecanethiol (Aldrich, code 01858) was added to the organic phase prior to spontaneous emulsification. The antioxidant-antineoplastic nanospheres were dialyzed overnight, and the concentration of thiol groups was determined as follows: Aldrithiol-2 (Sigma, code143049) was dissolved in ethanol (100 mM) and 10 μm of the solution was added to the suspension of antioxidant-antineoplastic nanospheres (80 μL). After addition of 10 μL of 10×PBS the mixture was incubated for 30 min at 37° C. The released 2-thiopyridone was separated using RP-HPLC with 50% acetonitrile as described in Example 1 and detected with UV detector at 341 nm. A standard curve for the determination of the released 2-thiopyridone was generated by measuring 2-thiopyridone generated from the reaction of known amount of Aldrithiol-2 and DTT.

To 3 mL of the suspension of 1-octadecanethiol-containing antioxidant-antineoplastic nanospheres 500 μL of 10×PBS and 1.5 molar equivalent of Cy3/Cy5/Cy5.5 maleimide were added. The reaction mixture was incubated overnight at room temperature and dialyzed at least 6 h to remove unbound cy5.5 maleimide from the suspension and filtered through 0.45 μm hydrophilic syringe filter (Sigma, code CLS431220) and stored at 4° C.

Example 13

Intracellular Uptake of Fluorescent-Labeled Antioxidant-Antineoplastic Nanospheres U87 glioma cells were incubated in the presence of fluorescent-labeled antioxidant-antineoplastic nanospheres. Four chamber culture slides (BD Biosciences, Bedford, Mass.) were seeded with U87 cells, and the cells were allowed to attach for 24 h. The medium was replaced with 1.0 mL of freshly prepared suspension of the fluorescent-labeled antioxidant-antineoplastic nanospheres in medium, and the chamber slides were incubated for up to 5 h. Cells were washed three time with PBS to remove uninternalized antioxidant-antineoplastic nanospheres, one drop of mounting medium with DAPI (Vectashield, Vector Laboratories, Burlingame, Calif.) was added and then cover slides were placed. For microscopic analysis of intracellular uptake of the fluorescent-labeled nanospheres, a Carl Zeiss Axio Imager Z1 fluorescence microscope equipped with ApoTome (Carl Zeiss MicroImaging, Inc., Thornwood, N.Y., USA) and Leica DMIRE2 confocal laser-scanning microscope with Confocal Software (Leica Microsystems, Bannockburn, Ill., USA) were used. For processing and analysis of the images, AxioVision (Rel. 4.6.3) software (Carl Zeiss) was used.

Example 14

In Vivo Imaging of Animals Treated with Fluorescent-Labeled Antioxidant-Antineoplastic Nanospheres For in vivo fluorescent imaging of animals treated with fluorescent-labeled antioxidant-antineoplastic nanospheres, Xenogen IVIS 200 imaging system (Xenogen, Alameda, Calif.) was used. Animals received intravenous injection (tail vein) with 150 μL of the fluorescent-labeled antioxidant-antineoplastic nanospheres at predetermined intervals. Imaging was made on whole body at predetermined intervals. Imaging was also made on isolated organs and tumor sections embedded and frozen in OCT (optimal cutting temperature) block. For imaging experiments, antioxidant-antineoplastic nanospheres were labeled with Cy5.5.

Example 15

Subcutaneous and Intracranial Tumor Implantation and Treatment

Subcutaneous Tumor Model:

5-6 week old nu/nu mice (obtained from Charles River Laboratories) were injected in the right flank with $10^6$ U87 glioma tumor cells suspended in PBS (100 uL). Animals were examined every other day for tumor growths, and treatment was started when the tumor size reached approx. 0.5 cm in diameter. The animals are pair-matched into treatment and control groups (day 0).

Starting on day 0, the animals received intravenous (tail vein) injection of 100-200 μl drugs or control on a daily basis for five days. Nu/nu mice received intravenous injection of the antioxidant-antineoplastic nanospheres prepared with a mixture of camptothecin derivatives and tocopherol up to 16 mg/kg/day. As control, animals received intravenous injection of saline, tocopherol nanoparticle, or irinotecan. Two perpendicular diameters are measured in the tumor twice a week, and the volume of each tumor is calculated according to the equation: V (mm3)=L (mm)×$W^2$ ($mm^2$)/2, where L is the longest diameter and W is the diameter perpendicular to L.

Intracranial Tumor Model:

The mice underwent intracranial stereotactic implantation of U87 glioblastoma tumor cells. To do the implantation, Mice were anesthetized using a ketamine (75 mg/kg) and dexmedetomidine (0.5 mg/kg) combination as a single intraperitoneal injection. Betadyne prep was used to prepare the skin at the incision site on the skull. A skin incision was made, a hole was drilled in the skull, and $10^5$ U87 cells suspended in 2 μl of PBS were implanted in the right frontal region of the brain using a Hamilton syringe. The animals were injected with atipamezole intraperitoneally to reverse the dexmedetomidine effect and are allowed to recover from anesthesia. A single subcutaneous injection of buprenorphine was administered as pain relief.

The animals were examined daily for signs of neurological impairment. The in vivo imaging was performed with the animals showing a moderate to severe symptom of brain tumor. For in vivo fluorescent imaging of the brain tumor-bearing animals, animals received intravenous injection (tail vein) with 150 μL of the fluorescent-labeled antioxidant-antineoplastic nanospheres. Imaging was made on whole body at predetermined intervals. The animals were scarified at predetermined intervals. Imaging was also made on isolated organs and tumor sections embedded and frozen in OCT (optimal cutting temperature) block. For imaging experiments on mice, antioxidant-antineoplastic nanospheres were labeled with Cy5.5. If the animals manifested severe hemiparesis, exhibited inability to access food or water, exhibited seizure activity, weakness, or paralysis, the animals were sacrificed. The brains were then harvested and examined.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A compound of Formula III:

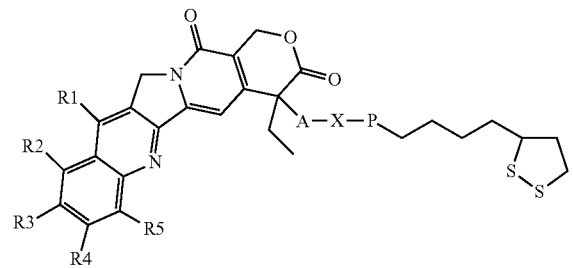

wherein

A is selected from the group consisting of —OC(O)—, —OC(O)O—, and —OC(O)N(R)—;

P is selected from the group consisting of —OC(O)— and —N(R)C(O)—;

Wherein each R is independently selected from the group consisting of a hydrogen atom or a $C_{2-12}$ alkyl;

X is a linker selected from the group consisting of:

i) $C_{2-12}$ alkyl;

ii) a moiety formed by esterification of two free esterifiable hydroxyl groups on a diol, wherein the diol is selected from the group consisting of:

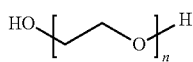

wherein n is an integer between 1 and 100,

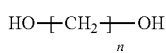

wherein n is an integer between 2 and 12,

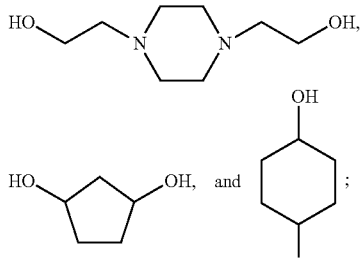

iii) a moiety formed by using a diamine as the linker X in the process of producing the compound, wherein the diamine is selected from the group consisting of:

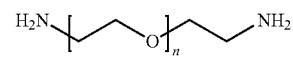

wherein n is an integer between 1 and 100, and

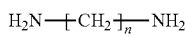

wherein n is an integer between 2 and 12; and iv) a moiety formed by using an aminoalcohol as the linker X in the process of producing the compound, wherein the aminoalcohol is selected from the group consisting of:

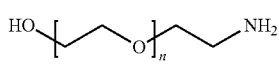

wherein n is an integer between 1 and 100, and

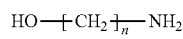

wherein n is an integer between 2 and 12;

wherein $R_1$, $R_2$, $R_3$, $R_4$, and $R_5$ are each independently hydrogen or alkyl.

2. A compound of claim 1, having Formula IV:

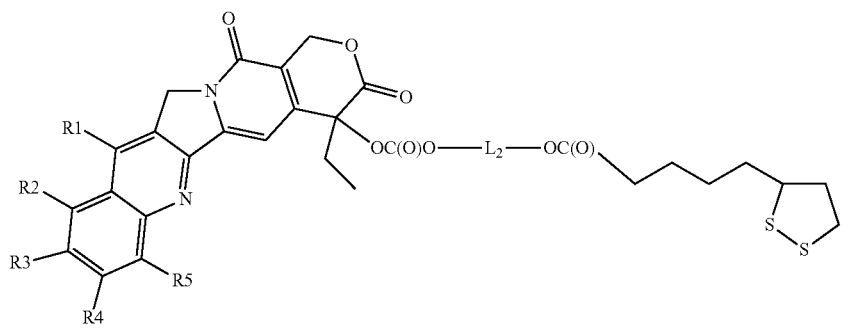

wherein $L_1$ is a moiety a moiety formed by esterification of two free esterifiable hydroxyl groups on a diol, wherein the diol is selected from the group consisting of:

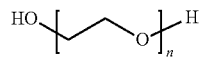

wherein n is an integer between 1 and 100,

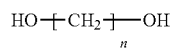

wherein n is an integer between 2 and 12,

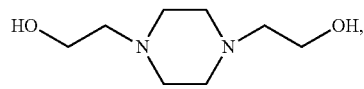

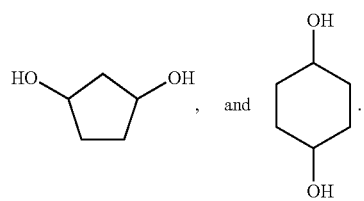

3. A compound of claim 1, having Formula XI:

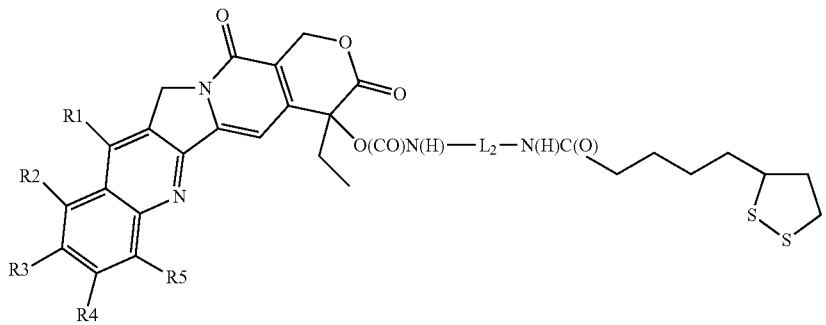

wherein $L_2$ is a moiety formed by using a diamine as the linker in the process of producing the compound, wherein the diamine is selected from the group consisting of:

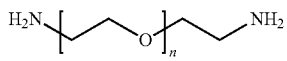

wherein n is an integer between 1 and 100, and

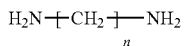

wherein n is an integer between 2 and 12; and
wherein $R_1$, $R_2$, $R_3$, $R_4$, and $R_5$ are each independently hydrogen or alkyl.

4. A compound of claim 1, having Formula XVIII:

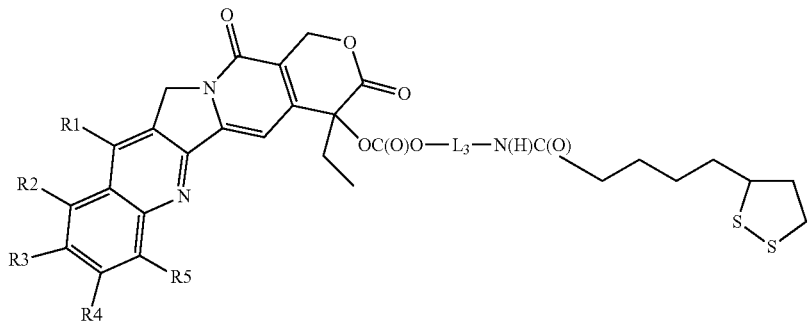

wherein $L_3$ is a moiety formed by using an aminoalcohol as the linker in the process of producing the compound, wherein the aminoalcohol is selected from the group consisting of:

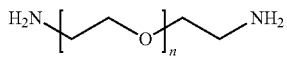

wherein n is an integer between 1 and 100, and

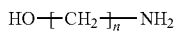

wherein n is an integer between 2 and 12.

5. The compound of claim 2, selected from the group consisting of:

Formula V
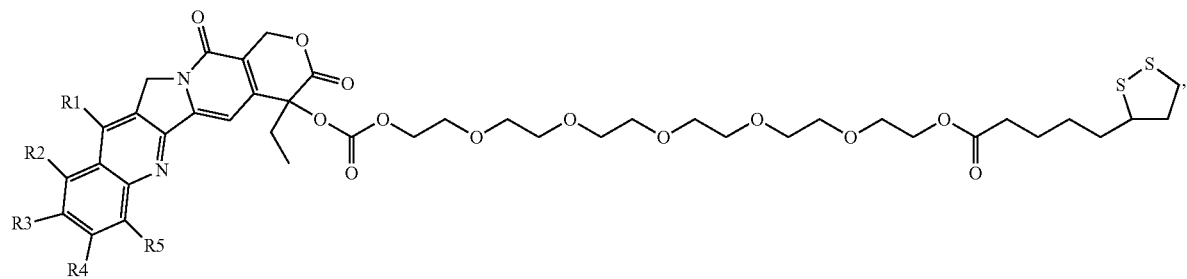
Formula VI
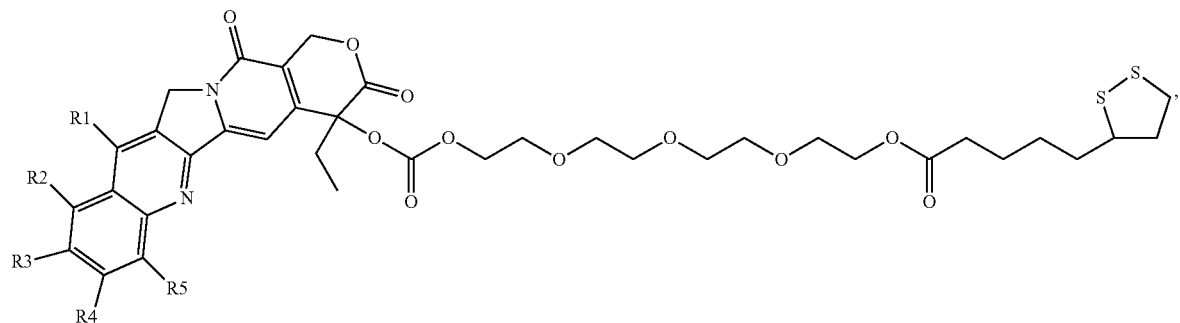
Formula VII
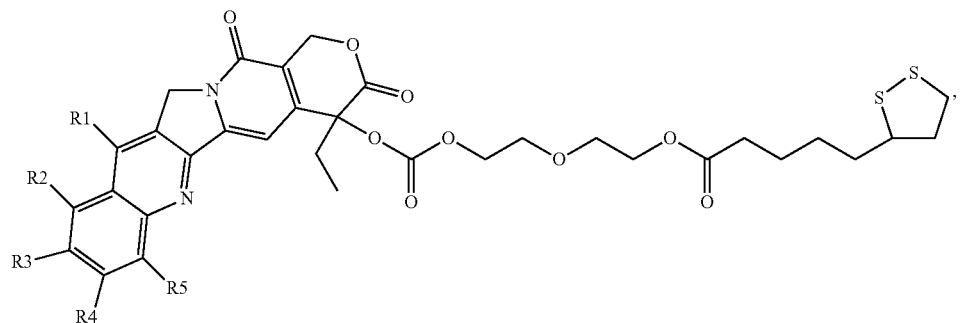
Formula VIII
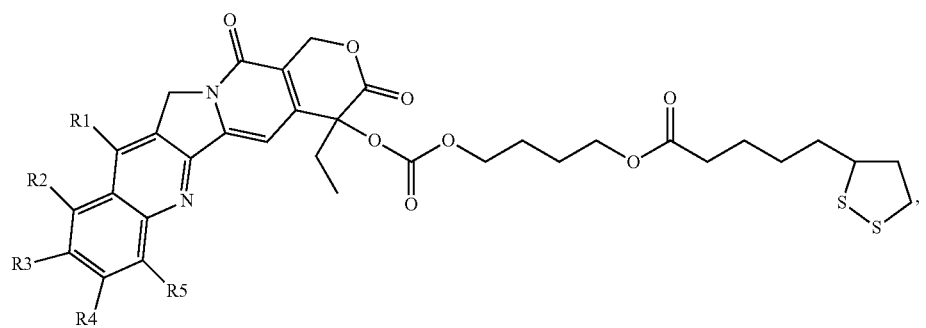
Formula IX
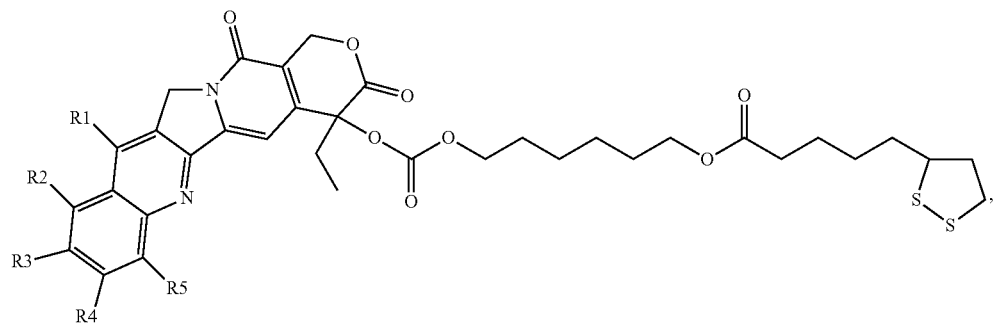

Formula X
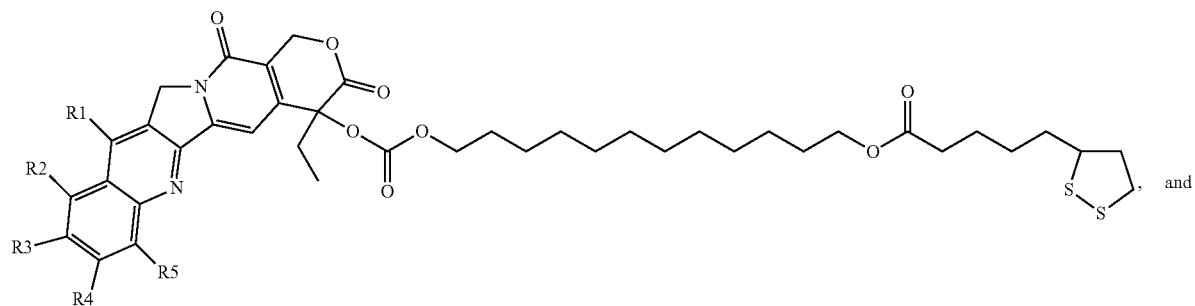
and
Formula XLVI
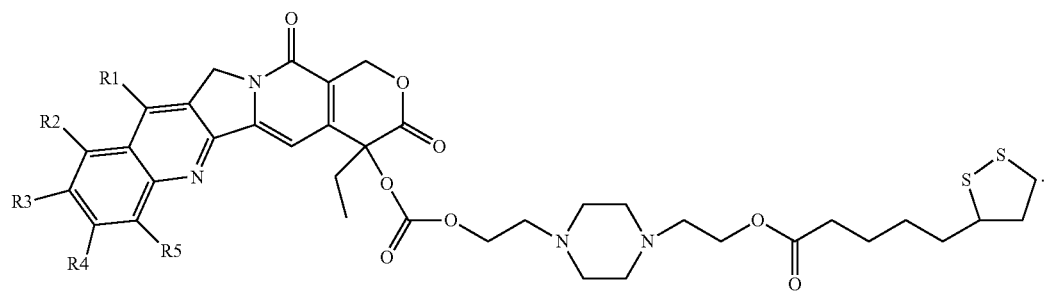
6. The compound of claim 3, selected from the group consisting of:
Formula XII
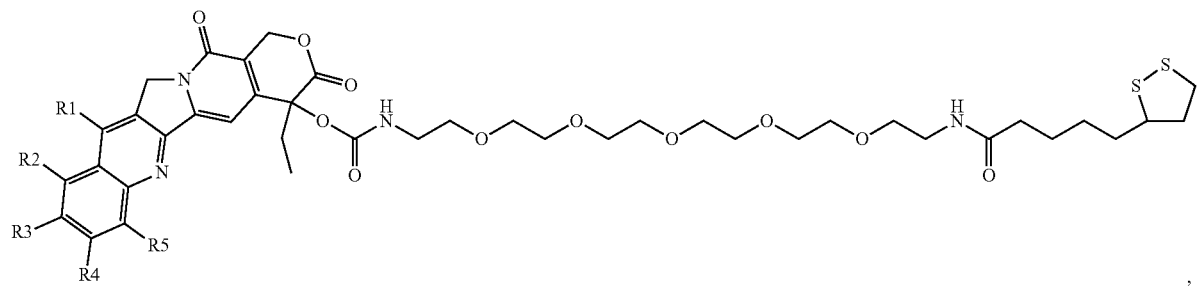
,
Formula XIII
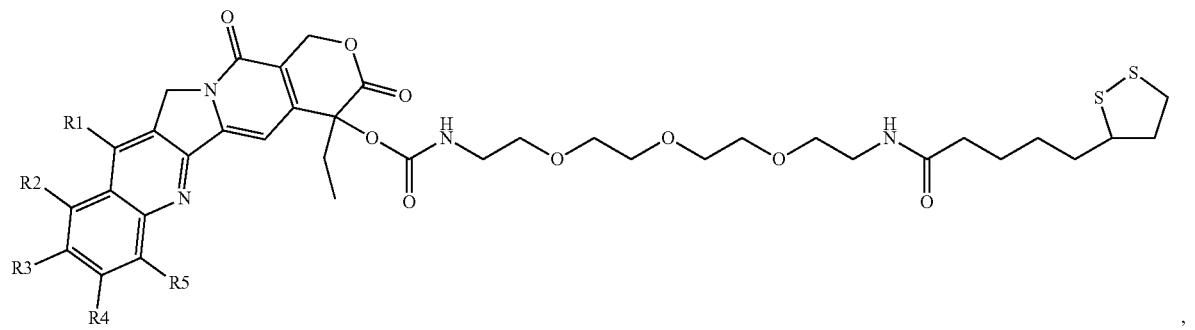
, -continued
Formula XIV
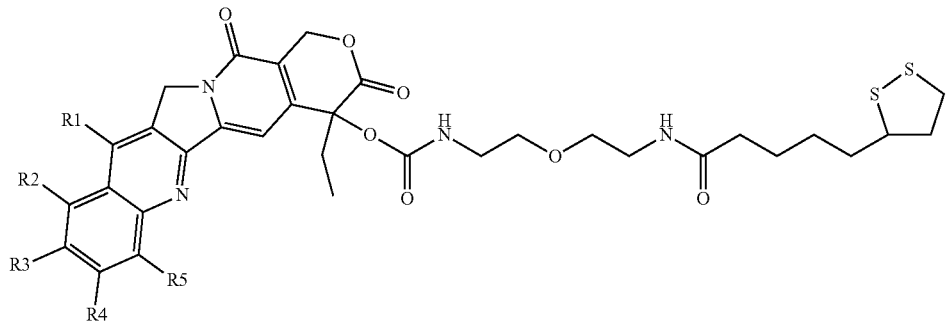
Formula XV
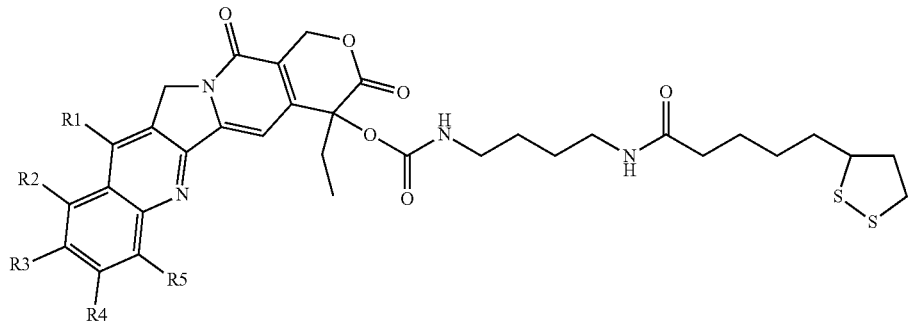
Formula XVI
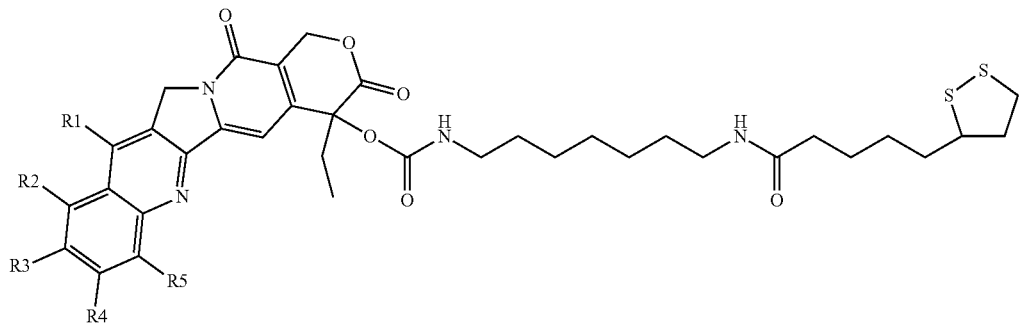
Formula XVII
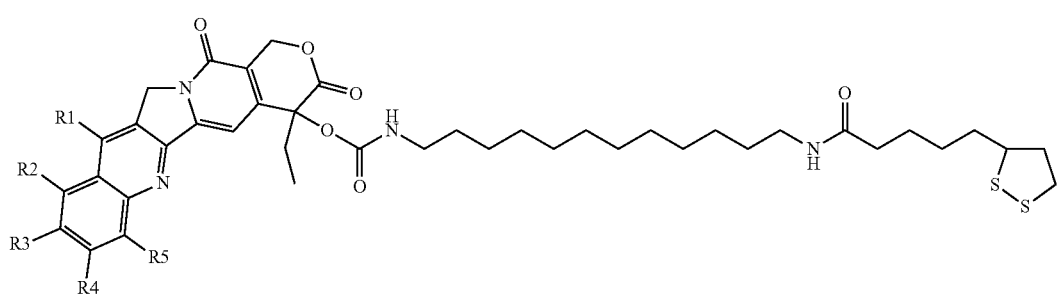
and
Formula XLVII
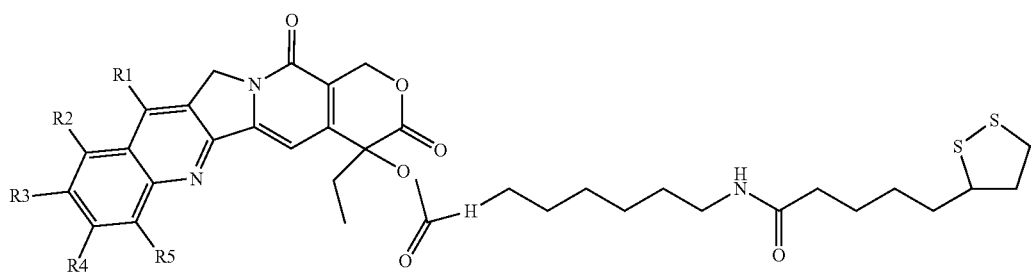

7. The compound of claim 4, selected from the group consisting of:
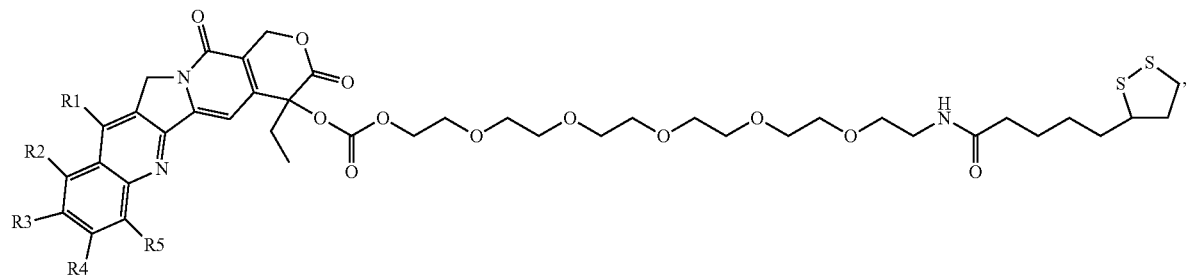
Formula XIX
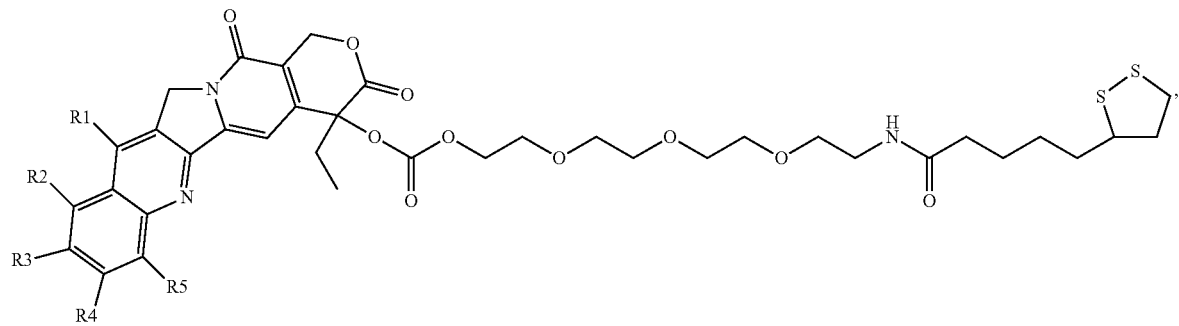
Formula XX
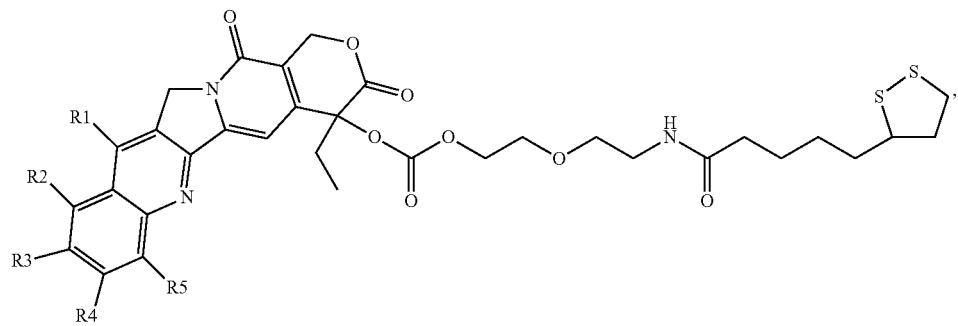
Formula XXI
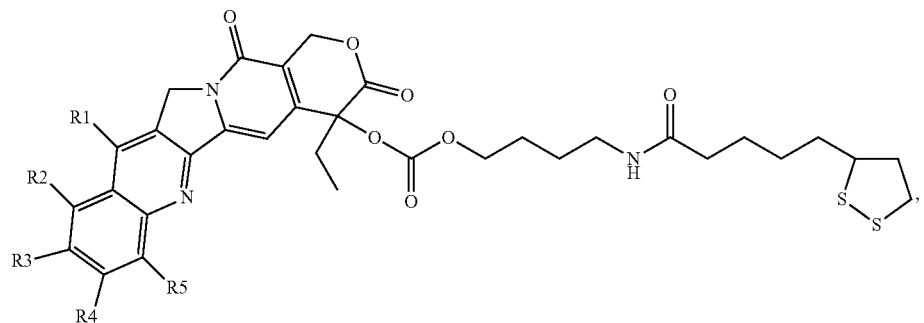
Formula XXII Formula XXIII
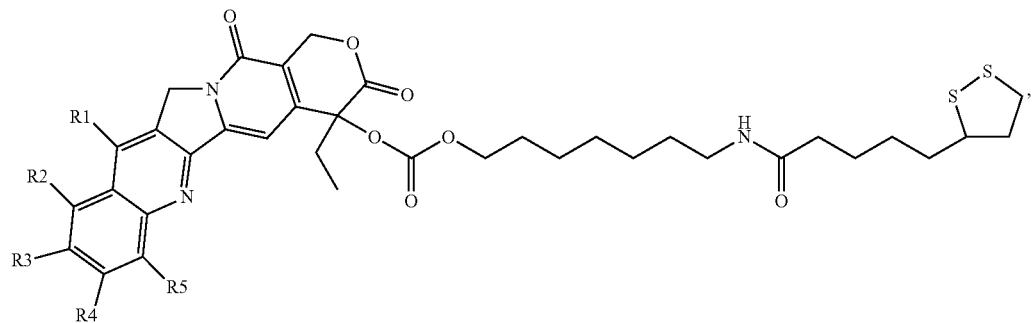
Formula XXIV
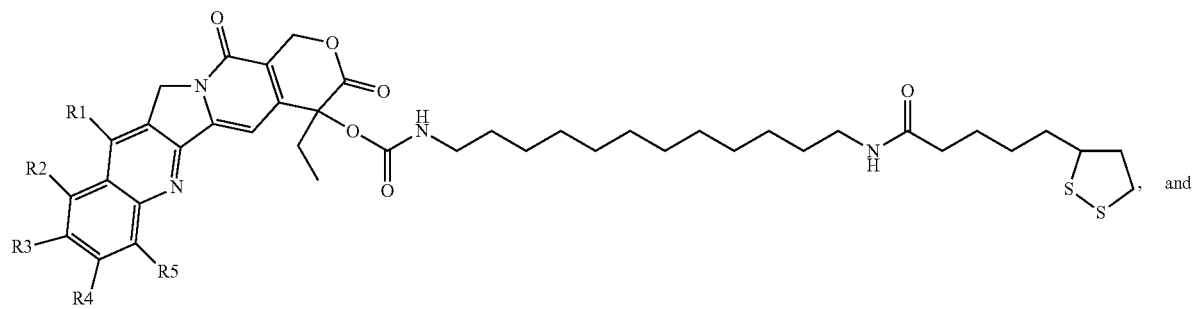
, and
Formula XLVIII
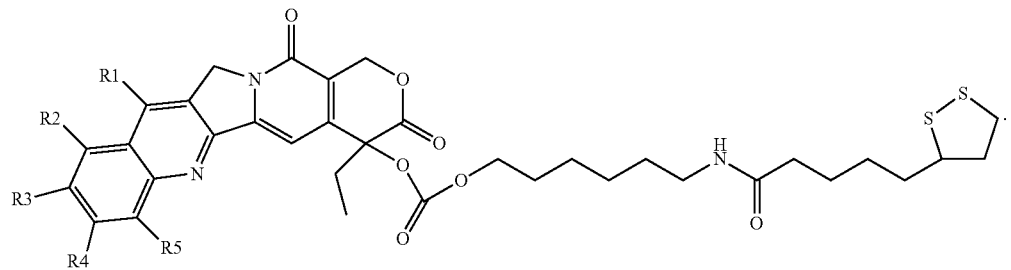
8. A compound selected from the group consisting of:
Formula XXV
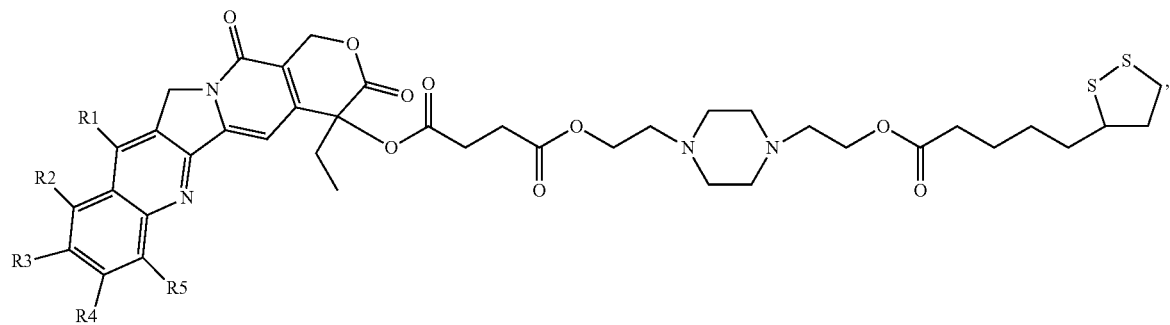
, Formula XXVI
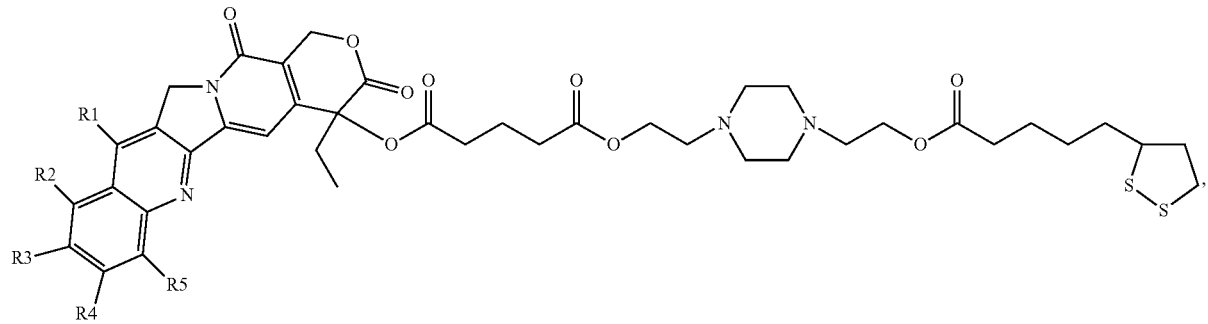
Formula XXVII
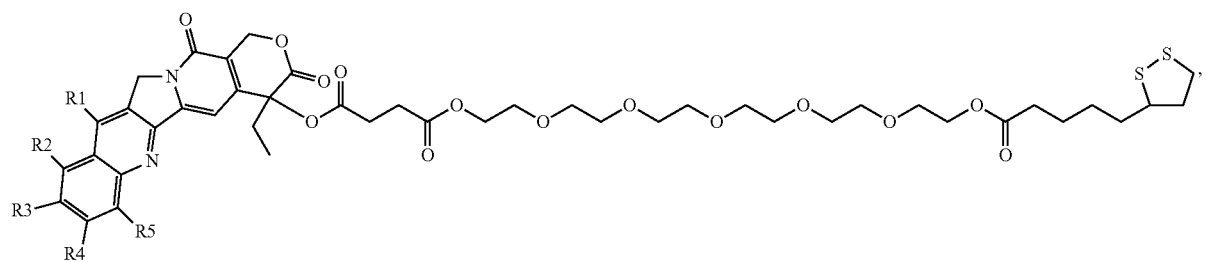
Formula XXVIII
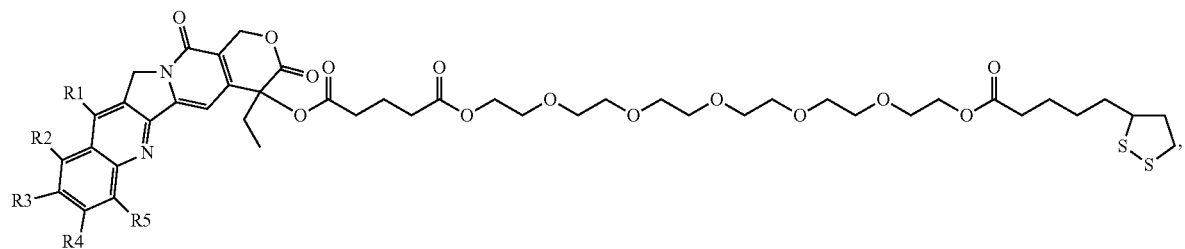
Formula XXIX
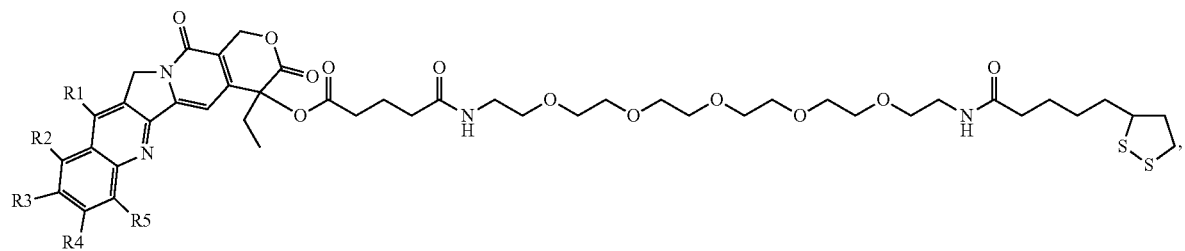
Formula XXX
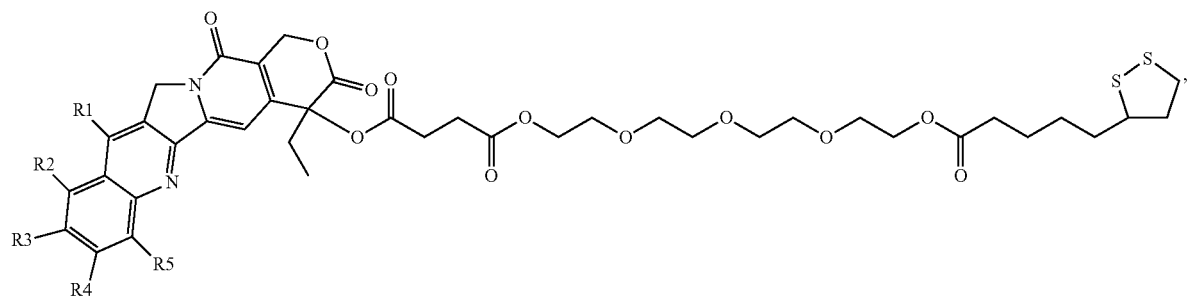

-continued
Formula XXXI
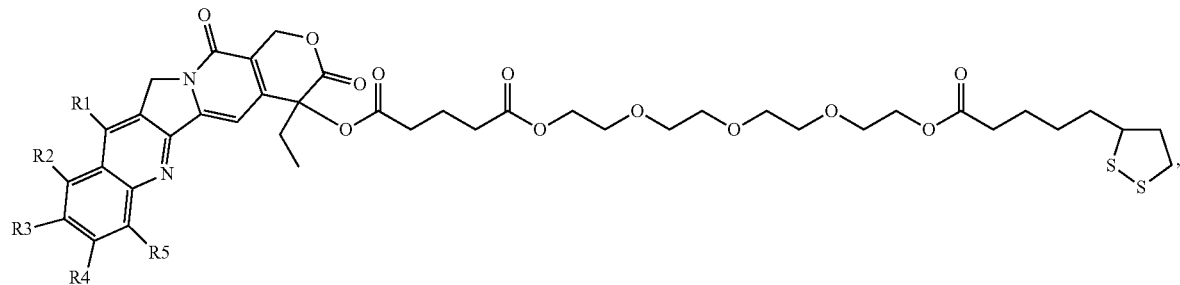
Formula XXXII
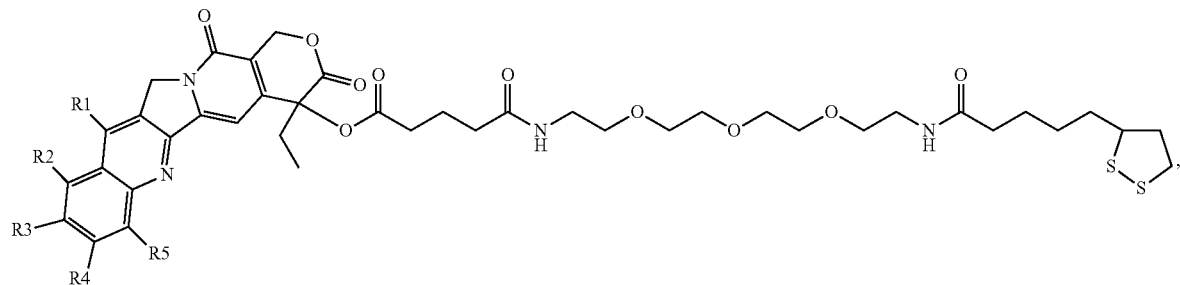
Formula XXXIII
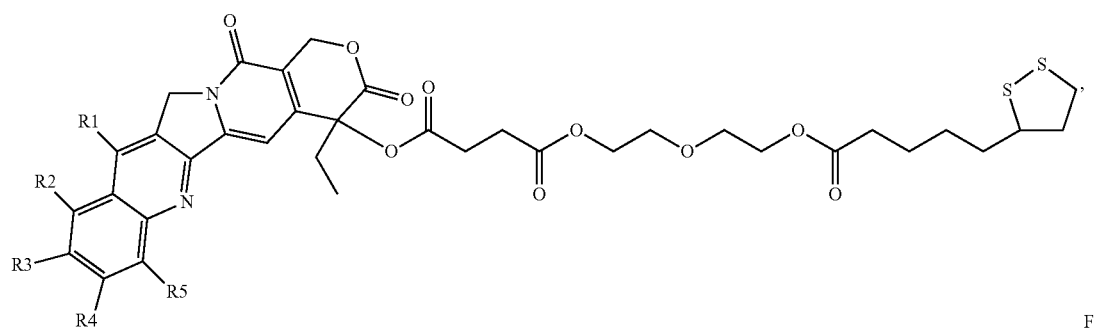
Formula XXXIV
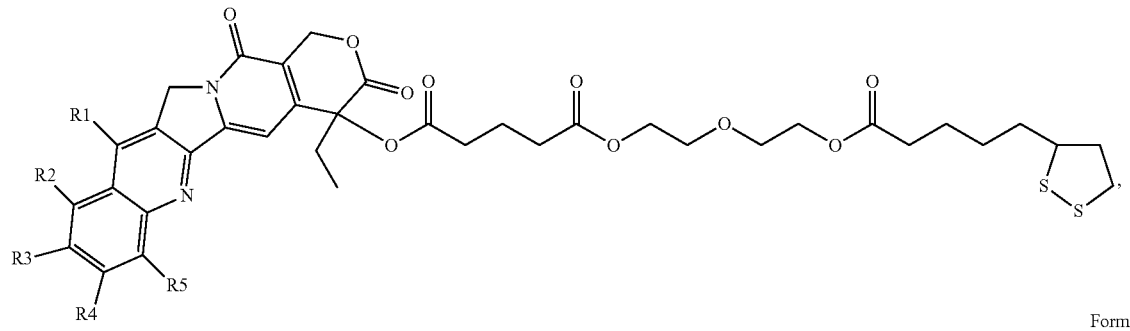
Formula XXXV
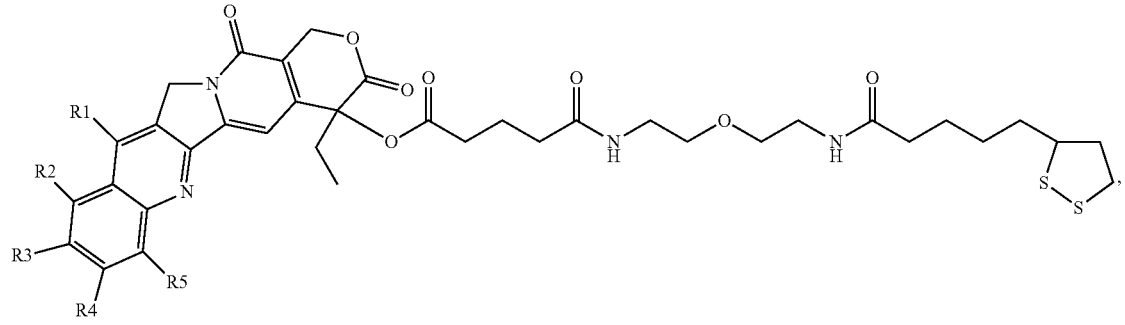

Formula XXVI
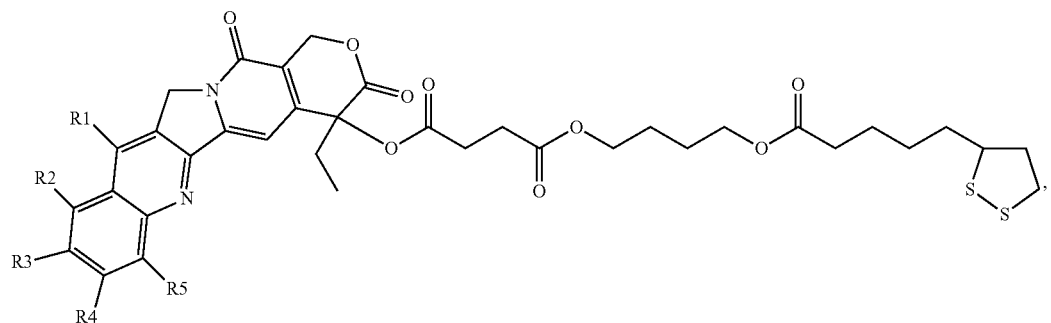
Formula XXXVII
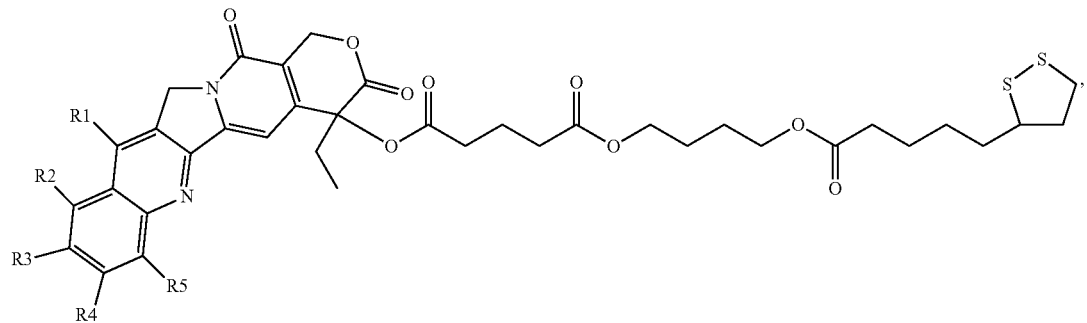
Formula XXXVIII
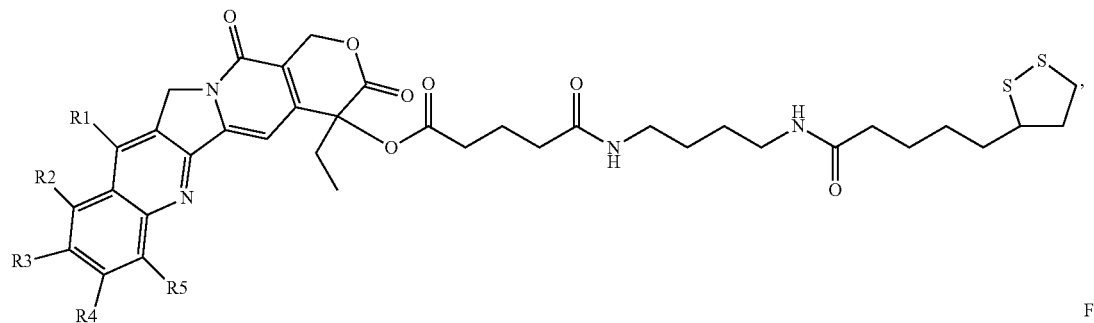
Formula XXXIX
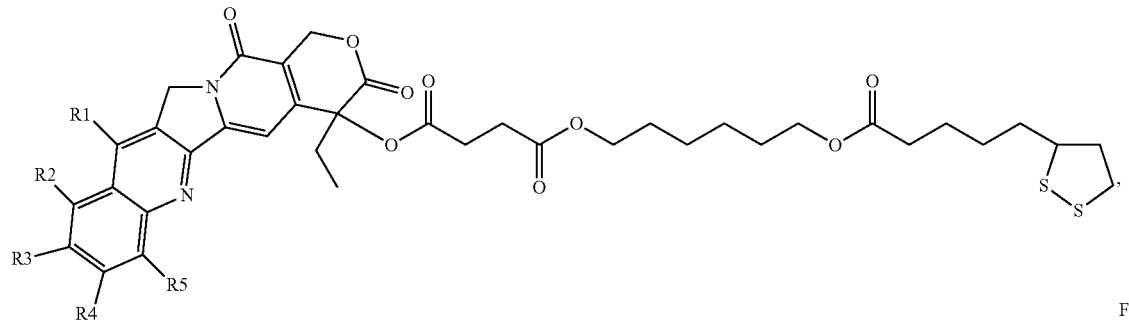
Formula XL
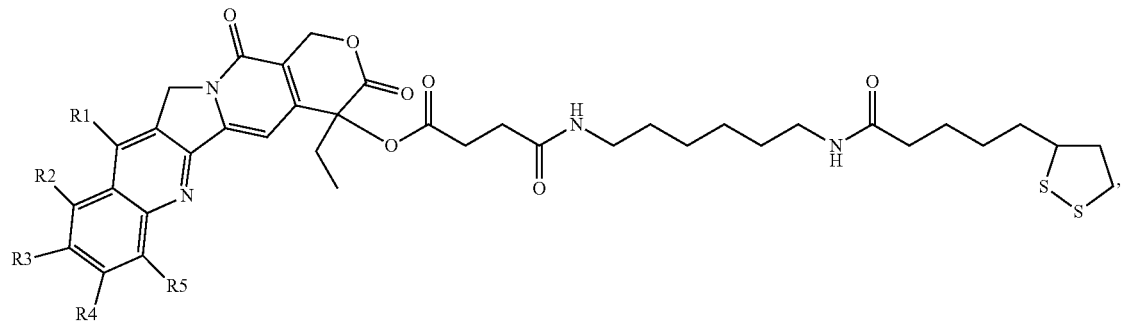

-continued
Formula XLI
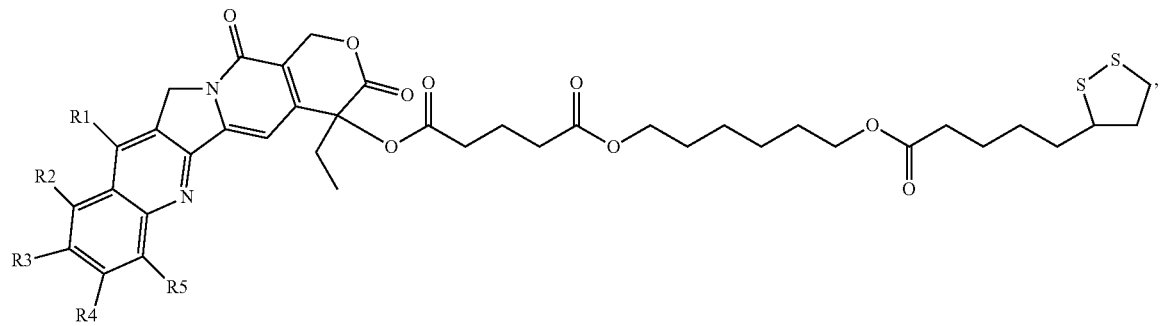
Formula XLII
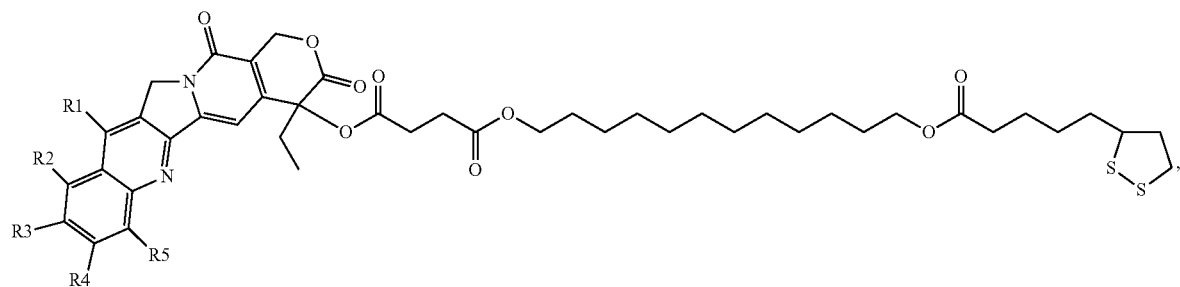
Formula XLIII
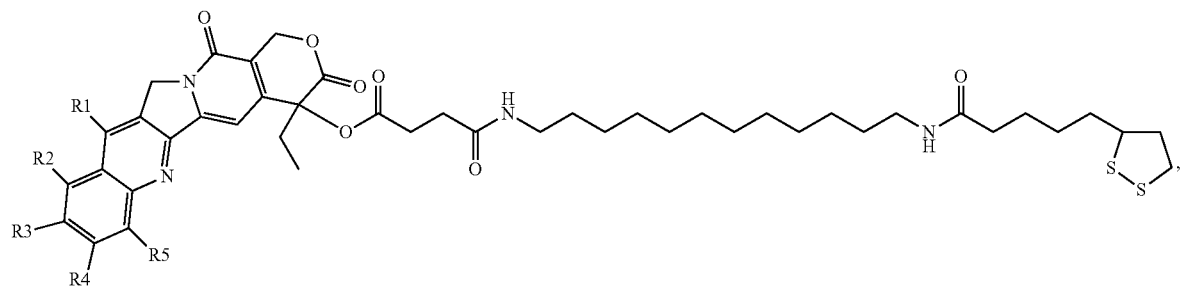
Formula XLIV
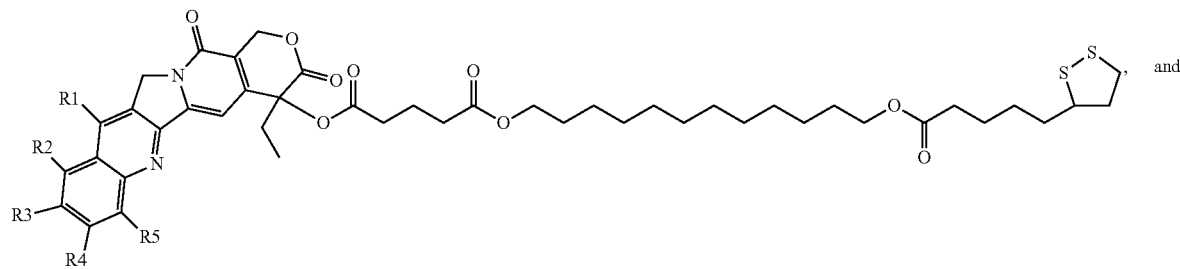
and
Formula XLV
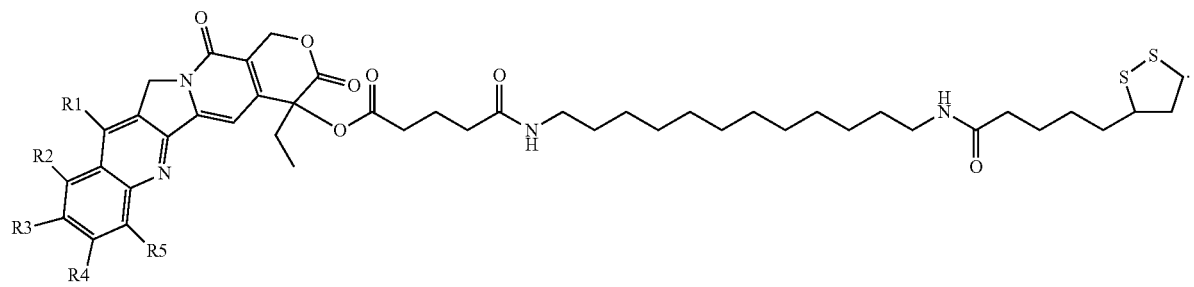

wherein R1, R2, R3, R4, and R5 are each independently selected from the group consisting of hydrogen and alkyl.
9. A compound selected from the group consisting of:
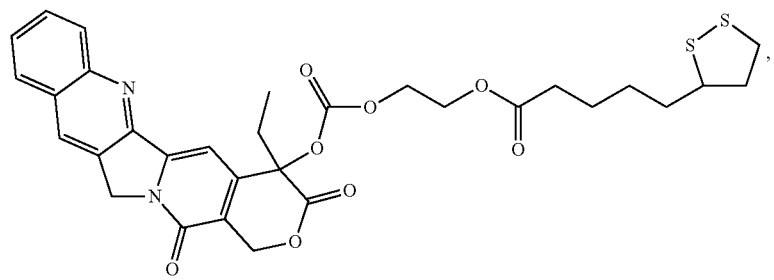
Compound 23
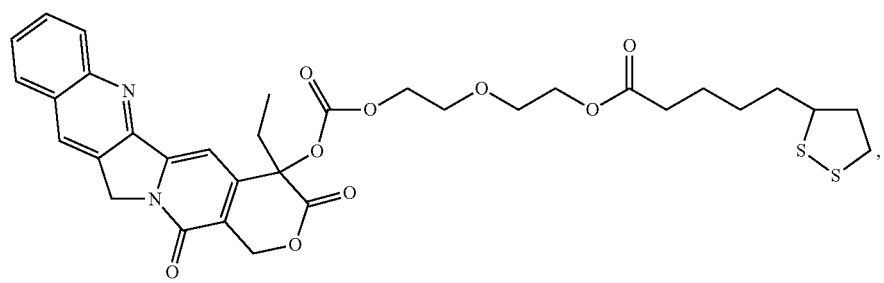
Compound 1
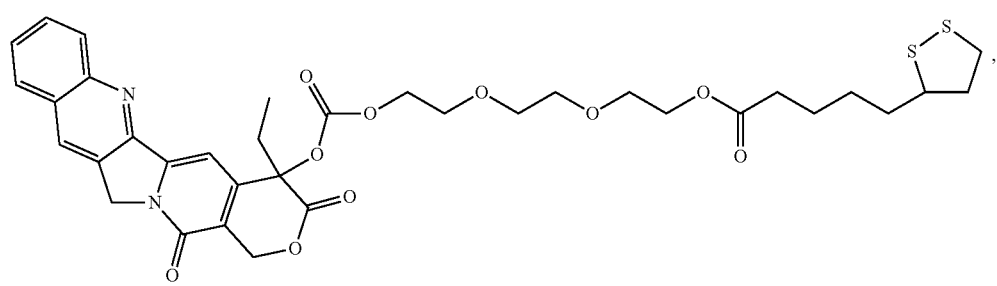
Compound 2
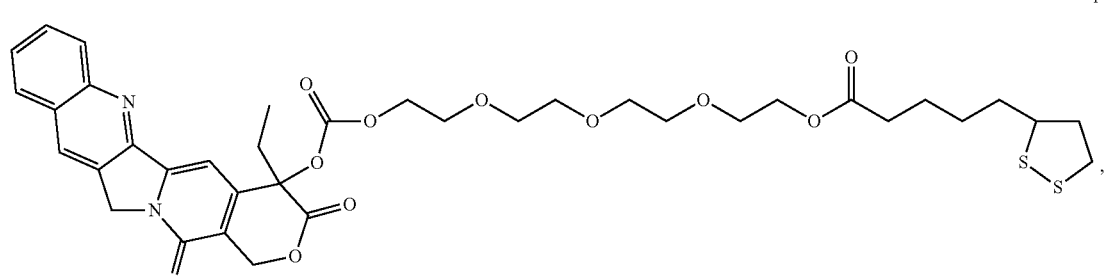
Compound 10
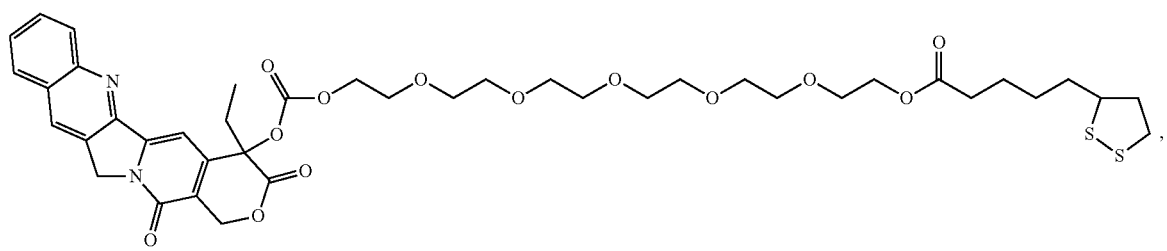
Compound 3

-continued
Compound 4
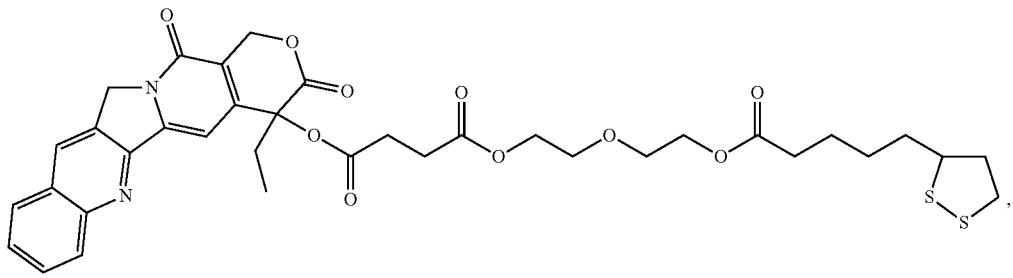
Compound 5
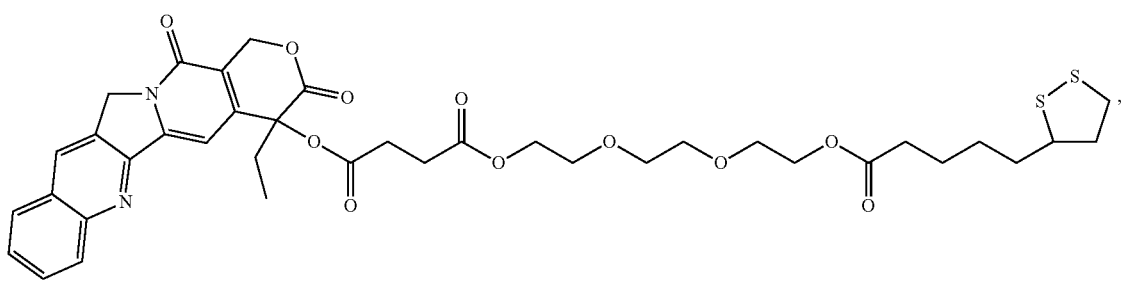
Compound 11
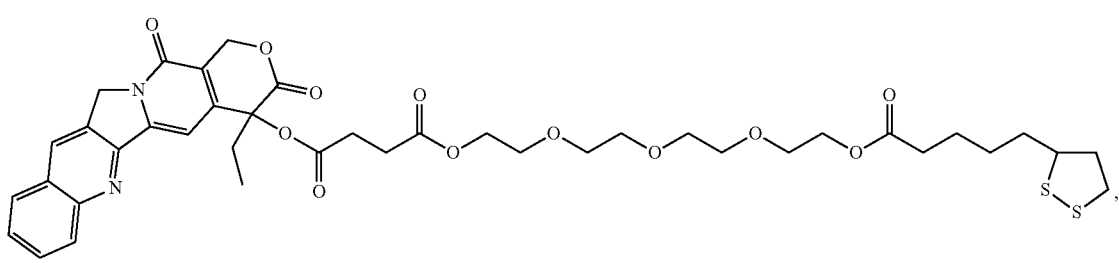
Compound 6
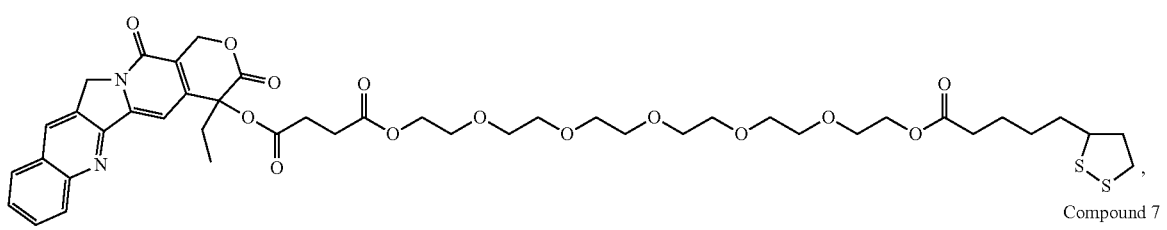
Compound 7
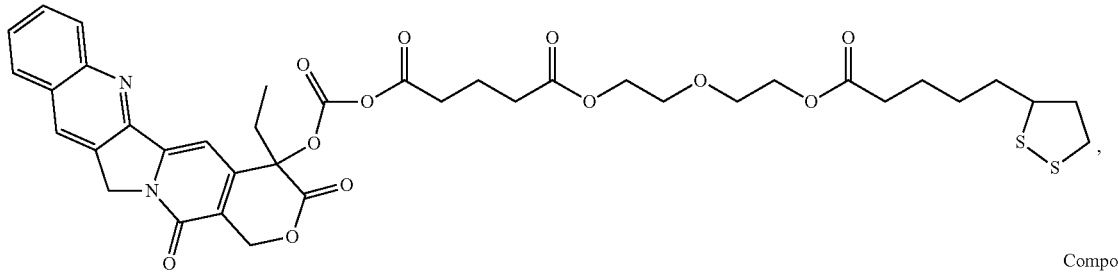
Compound 8
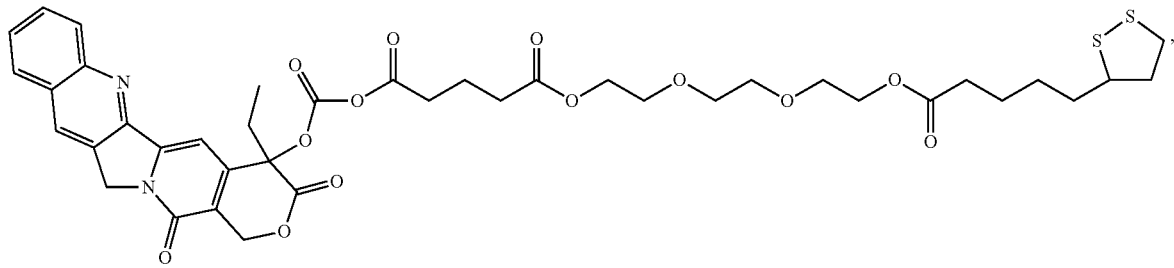

Compound 12
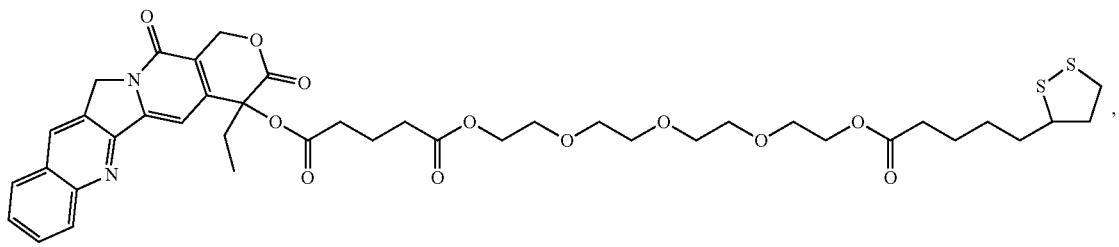
Compound 9
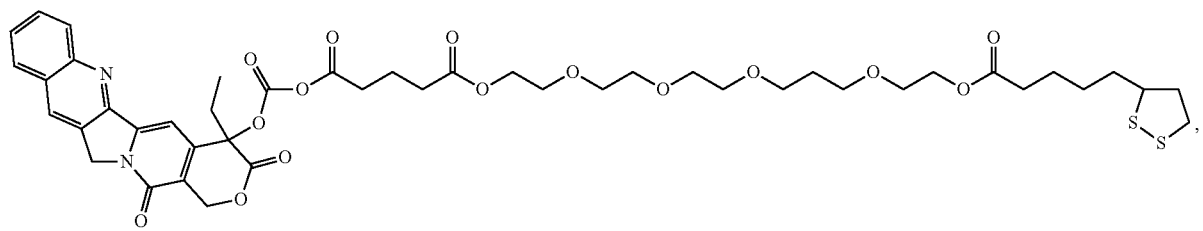
Compound 13
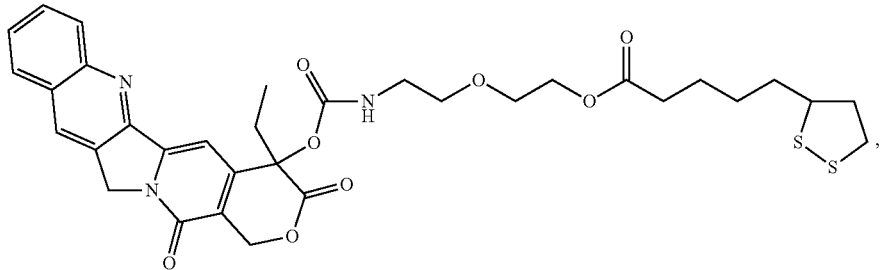
Compound 14
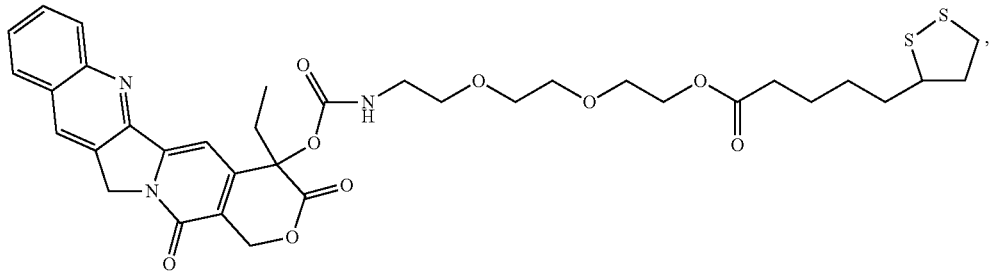
Compound 15
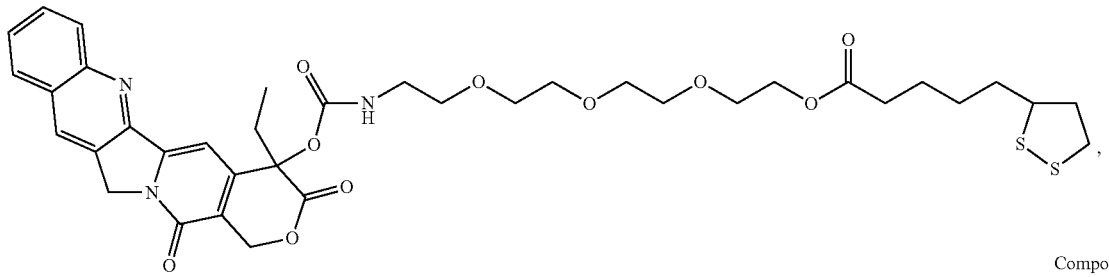
Compound 16
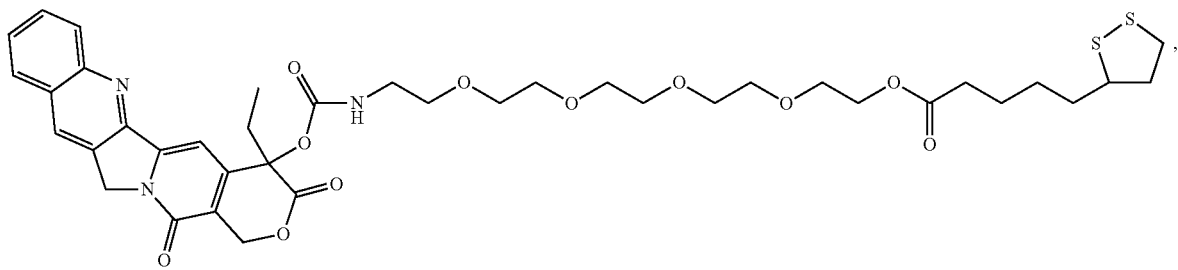

Compound 17
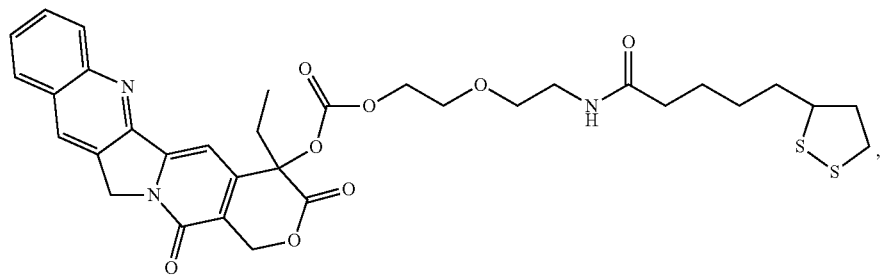
Compound 18
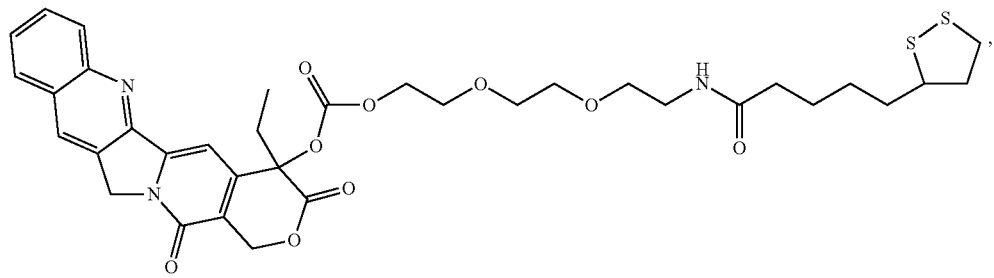
Compound 19
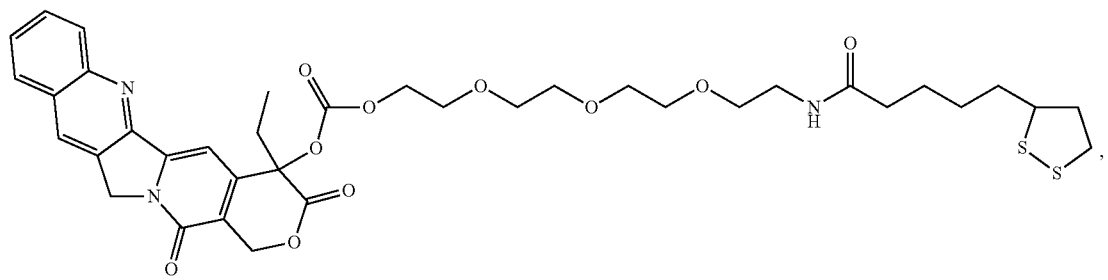
Compound 20
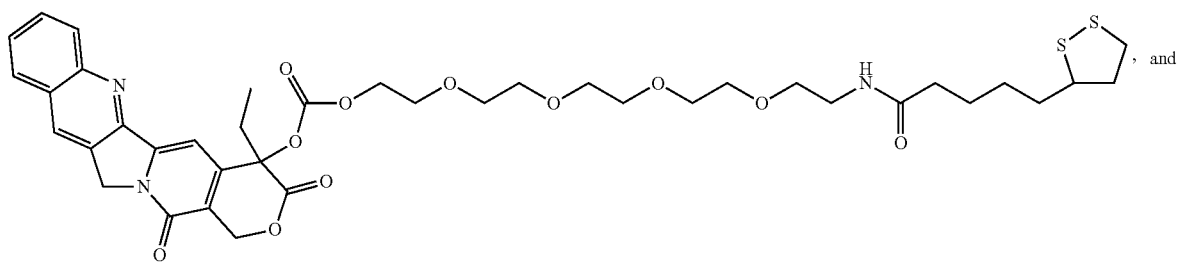
Compound 21
, and

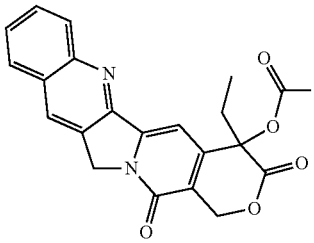
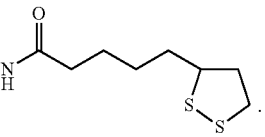

Compound 22

10. A nanosphere, comprising:
a compound of claim 1.

11. The nanosphere of claim 10, further comprising:
a compound selected from the group consisting of: a multiple α-lipoic acid-containing hydrophobic compound, α-tocopherol, a nonsteroidal anti-inflammatory drug (NSAID) derivative and combinations thereof.

12. A nanosphere, comprising:
a compound of claim 2.

13. The nanosphere of claim 10, further comprising:
a compound selected from the group consisting of: a multiple α-lipoic acid-containing hydrophobic compound, α-tocopherol, a nonsteroidal anti-inflammatory drug (NSAID) derivative, and combinations thereof.

14. A nanosphere, comprising:
a compound of claim 8.

15. The nanosphere of claim 14, further comprising:
a compound selected from the group consisting of: a multiple α-lipoic acid-containing hydrophobic compound, α-tocopherol, a nonsteroidal anti-inflammatory drug (NSAID) derivative, and combinations thereof.

16. A pharmaceutical composition, comprising:
a pharmaceutically acceptable carrier or excipient; and
a compound as defined in claim 5.

17. A pharmaceutical composition, comprising:
a pharmaceutically acceptable carrier or excipient; and
a compound as defined in claim 6.

18. A pharmaceutical composition, comprising:
a pharmaceutically acceptable carrier or excipient; and
a compound as defined in claim 7.

19. A pharmaceutical composition, comprising:
a pharmaceutically acceptable carrier or excipient; and
a compound as defined in claim 8.

20. A pharmaceutical composition, comprising:
a pharmaceutically acceptable carrier or excipient; and
a compound as defined in claim 9.

21. A pharmaceutical composition, comprising:
a pharmaceutically acceptable carrier or excipient; and
a compound as defined in claim 1.

22. A pharmaceutical composition, comprising:
a pharmaceutically acceptable carrier or excipient; and
a compound as defined in claim 2.

23. A pharmaceutical composition, comprising:
a pharmaceutically acceptable carrier or excipient; and
a compound as defined in claim 3.

24. A pharmaceutical composition, comprising:
a pharmaceutically acceptable carrier or excipient; and
a compound as defined in claim 4.

25. A method of treating cancer in a subject in need thereof, comprising:
providing a composition comprising a compound of claim 1; and
administering a therapeutically effective amount of the composition to the subject to treat the cancer.

26. A method of treating cancer in a subject in need thereof, comprising:
providing a composition comprising a compound of claim 2; and
administering a therapeutically effective amount of the composition to the subject to treat the cancer.

27. A method of treating cancer in a subject in need thereof, comprising:
providing a composition comprising a compound of claim 8; and
administering a therapeutically effective amount of the composition to the subject to treat the cancer.

28. A method of treating cancer in a subject in need thereof, comprising:
providing the nanosphere of claim 10; and
administering a therapeutically effective amount of the nanosphere to the subject to treat the cancer.

29. A method of treating cancer in a subject in need thereof, comprising:
providing the nanosphere of claim 12; and
administering a therapeutically effective amount of the nanosphere to the subject to treat the cancer.

30. A method of treating cancer in a subject in need thereof, comprising:
providing the nanosphere of claim 14; and
administering a therapeutically effective amount of the nanosphere to the subject to treat the cancer.

* * * * *